United States Patent
Kobayashi et al.

(10) Patent No.: US 6,204,264 B1
(45) Date of Patent: Mar. 20, 2001

(54) BENZIMIDAZOLE DERIVATIVE, HAIR GROWTH PROMOTER AND EXTERNAL COMPOSITION FOR SKIN USING THE SAME

(75) Inventors: Koji Kobayashi; Hirotada Fukunishi; Kenichi Umishio; Masahiro Tajima, all of Kanagawa (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/398,200

(22) Filed: Sep. 17, 1999

(30) Foreign Application Priority Data

Sep. 21, 1998 (JP) ................................. 10-266709

(51) Int. Cl.$^7$ .................... A61R 31/535; A61R 31/4184; C07D 403/06; C07D 235/04; C07D 235/06

(52) U.S. Cl. ..................... 514/235.8; 514/235.8; 514/254.05; 514/394; 514/395; 544/139; 544/370; 548/304.7; 548/306.1; 548/307.4; 548/308.1; 548/309.4; 548/309.7

(58) Field of Search ............... 514/235.8, 254.05, 514/394, 395; 544/139, 370; 548/304.7, 306.1, 307.4, 308.1, 309.4, 309.7

(56) References Cited

FOREIGN PATENT DOCUMENTS

| 10 78 132 | 3/1960 | (DE) . |
|---|---|---|
| 1078132 | * 3/1960 | (DE) . |
| 22 50 345 | 4/1973 | (DE) . |
| 59-181262 | * 10/1984 | (JP) . |
| 61-072763 | * 4/1986 | (JP) . |
| 07304736 | 11/1995 | (JP) . |
| 07316022 | 12/1995 | (JP) . |
| 07316023 | 12/1995 | (JP) . |
| 08020521 | 1/1996 | (JP) . |
| 08026942 | 1/1996 | (JP) . |
| WO 97/35540 | 10/1997 | (WO) . |

OTHER PUBLICATIONS

Iemura, Synthesis of 2-(4-substituted-1piperazinyl)benzimidazoles as H1-Antihistaminic Agents, J. Med. Chem., 29(7), pp. 1178–1183, 1986.*
Garnovski, Competitive Coordination of 2–aminoazoles and 2–aminoazines, Koord. Khim., 14(3), pp. 299–306, 1988.*
Iemura, R. et al., "Synthesis of 2-(4-Substituted-1 piperazinyl) benzimidazoles as H$_1$ Antihistaminic Agents", J. Med Chem. vol. 29, No. 7, pp. 1178–1183.

Pozharskii AF et al., "Benzimidazole derivatives. XXVII. Synthesis and reaction of some N–derivative so benzimidazole, containing branched and high–molecular–weight substituents in position 1, with nucleophilic reagents", p. 486, Chemical Abstracts vol. 076, No. 21, Abstract No. 126865y, 1972.
Garnovskii DA et al., Competitive coordination of 2–aminoazoles and 2–aminoazines, p. 808, col. 2, Chemical Abstracts vol. 109, No. 10, 1988.
American Chemical Society, Abstract, CA61:3091f, with STN International Registry File Search Results, RN 94297–44–6, 88637–07–4 and RN 61981–81–5 (Mar. 31, 1997). Total of 7 pages filed.

* cited by examiner

Primary Examiner—Mukund J. Shah
Assistant Examiner—Ben Schroeder
(74) Attorney, Agent, or Firm—Ronald R. Snider; Snider & Associates

(57) ABSTRACT

A benzimidazole derivative or a salt thereof expressed by the following Formula (I):

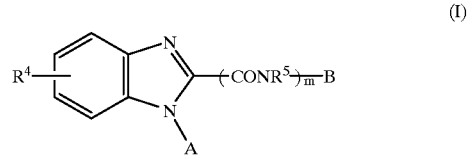

(I)

wherein one of A and B is a hydrocarbon group of $C_{10-30}$ expressed by $R^1$ and the other is $-(CH_2)_n-NR^2R^3$; $R^2$ and $R^3$ individually represent H, lower alkyl, phenyl or benzyl, or $-NR^2R^3$ may be a heterocycle having 3–7 members, or $-CONR^5-(CH_2)_n-NR^2R^3$ may be the following Group (W):

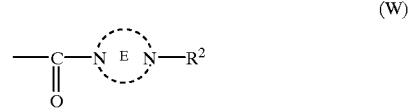

(W)

wherein $R^2$ is H, lower alkyl, phenyl or benzyl and ring E is a heterocycle of 6 or 7 members; $R^4$ is selected from the group consisting of H, halogen, cyano, trifluoromethyl, lower alkyl and etc.; $R^5$ is H, lower alkyl, lower acyl or lower alkylcarbamoyl; m is 0 or 1; and n is an integer of 0–5. The benzimidazole derivative or the salt thereof has excellent hair growth and regrowth promoting effects, which are useful for care, improvement or prevention of hair loss in mammals and, in particular, in human.

16 Claims, 13 Drawing Sheets

Fig. 1 Reaction Formula AA

Fig. 2 Reaction Formula AB

Reaction Formula AC

Reaction Formula AD

Reaction Formula BA

Fig. 6 Reaction Formula BB
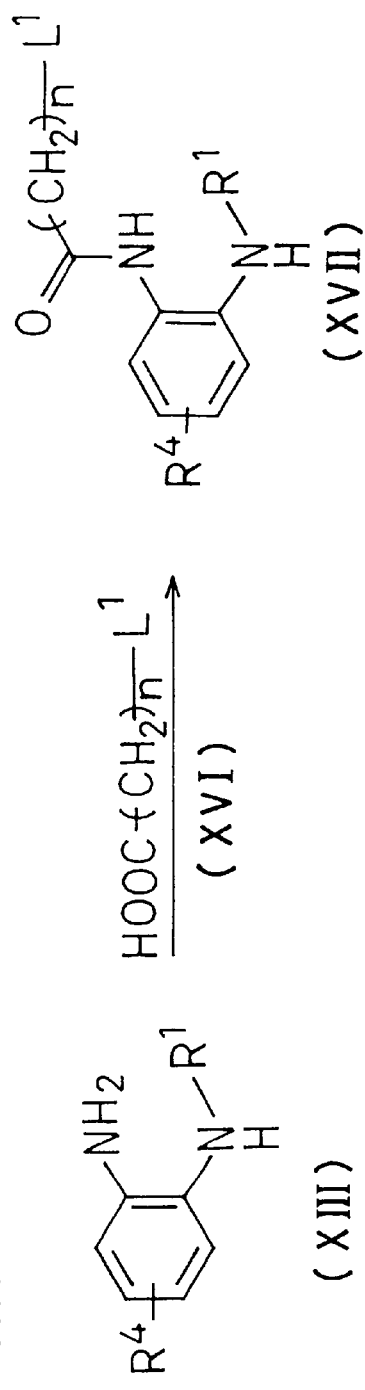
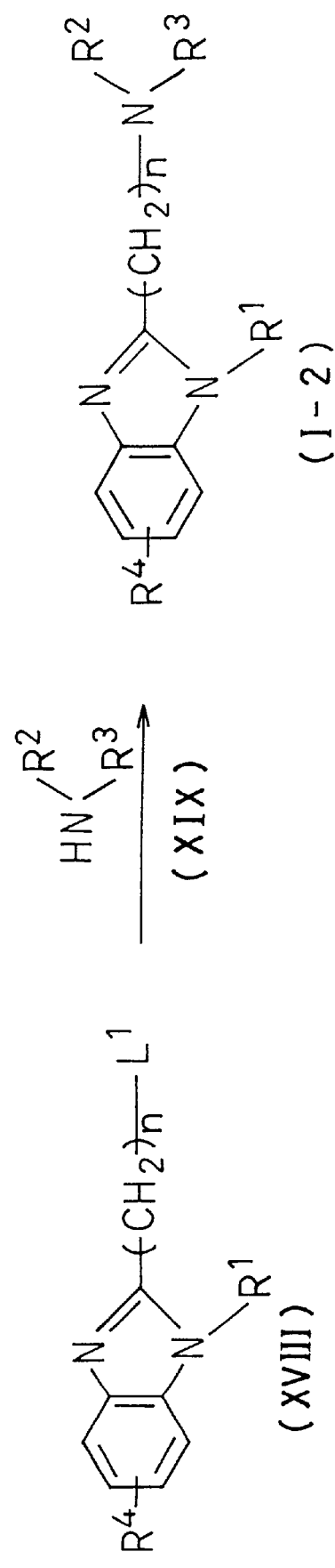

Reaction Formula BC

Fig. 8 Reaction Formula CA

Reaction Formula CB

Fig. 10
Reaction Formula DA
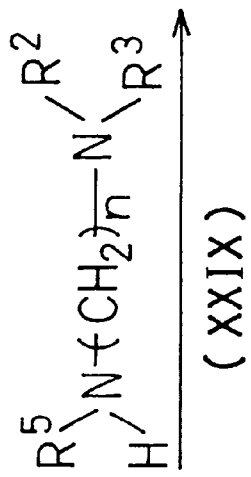 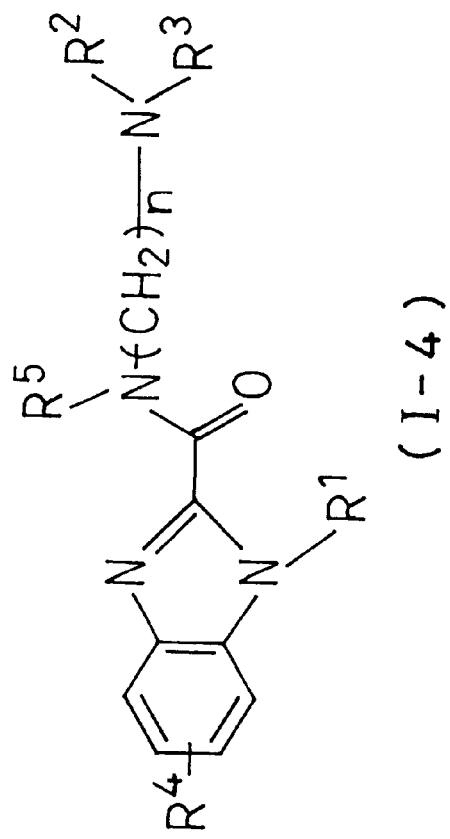 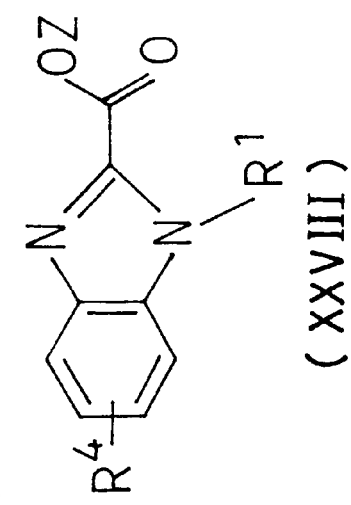

Reaction Formula DB

Reaction Formula DC

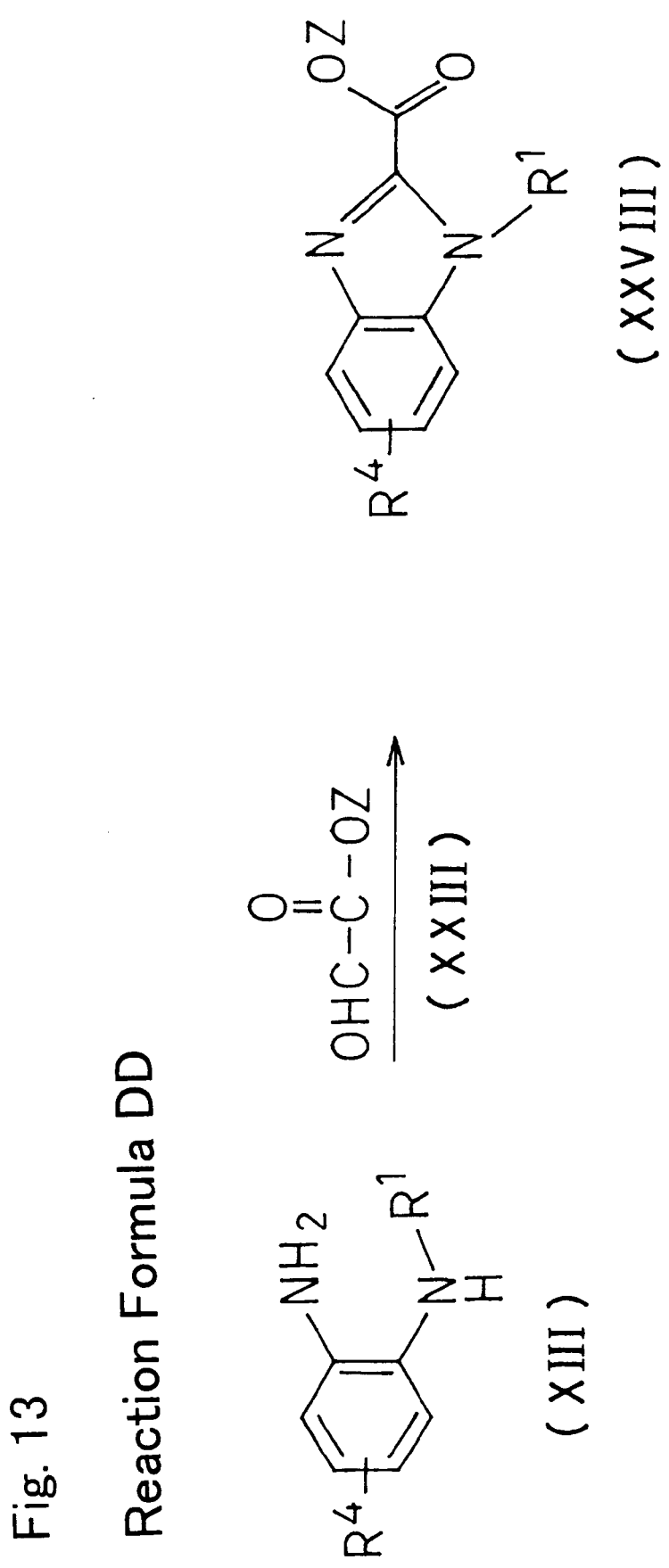
Fig. 13 Reaction Formula DD

BENZIMIDAZOLE DERIVATIVE, HAIR GROWTH PROMOTER AND EXTERNAL COMPOSITION FOR SKIN USING THE SAME

RELATED APPLICATIONS

This application claims the priority of Japanese Patent Application No. 10-266709 filed on Sep. 21, 1998, which is incorporated herein by reference.

FIELD OF THE INVENTION

The present invention relates to a benzimidazole derivative and, in particular, to a benzimidazole derivative that has excellent hair growth effect.

BACKGROUND OF THE INVENTION

At the present time, scalp abnormality due to activation of androgen in an organ such as hair root or sebaceous gland, lowering of blood stream toward hair follicle, excess secretion of sebum, generation of peroxide and the like has been considered as a cause of baldness or hair loss. Accordingly, a compound or composition that can remove or reduce the above-mentioned problems has been generally included into a hair growth promoting composition to promote hair growth and regrowth and to prevent hair loss, for a long time (in the present invention, "hair growth promoting composition" includes hair regrowth promoting composition, and the like).

At present, compounds or crude drug extracts having various functions have been compounded to the hair growth promoting composition. These functions include blood flow promoting action, topical stimulation, hair follicle activating action, antiandrogen action, antiseborrheic action and the like have been known. Examples of drugs having blood flow promoting action include swertia herb extract, vitamin E and its derivative, and benzyl nicotinate. Examples of drugs which promote blood circulation by topical stimulation include capsicum tincture, cantharides tincture, camphor and vanillic acid nonylamide. Examples of drugs having hair follicle activating action include hinokitiol, placental extract, photosensitizing dye, pantothenic acid and derivative thereof. Examples of drugs having antiandrogen action include estradiol and estrone. Examples of drugs having antiseborrheic action include sulfur, thioxolone and vitamin $B_6$.

In addition to these drugs, salicylic acid, resorcine and the like that have corneocyte desquamating action and antibacterial action can be compounded to hair growth promoting composition for the purpose of preventing dandruff. Further, glycyrrhizic acid, menthol and the like can be compounded in order to prevent inflammation of scalp. Furthermore, amino acids, vitamins, extracts of crude drugs and the like can be compounded so as to aliment to hair follicle and activate enzyme activity.

Meanwhile, for example, D(L)-pantolactone (Unexamined Japanese Patent Publication No. Hei 8-26942), 2(1H)-pyridone derivative (Unexamined Japanese Patent Publication No. Hei 8-20521), $N^G$-nitro-L-arginine (Unexamined Japanese Patent Publication No. Hei 7-316023), 3-methyleneisoindolin-1-one derivative (Unexamined Japanese Patent Publication No. Hei 7-316022), indole derivative (Unexamined Japanese Patent Publication No. Hei 7-304736) are disclosed in recent patents as drugs having hair regrowth effect, hair growth effect, and hair loss protecting effect.

However, although the drugs described above are compounded to the conventional hair growth promoting compositions, they do not always exhibit sufficient hair regrowth and growth promoting effect.

SUMMARY OF THE INVENTION

In view of the foregoing problem in the prior art, an object of the present invention is to provide a compound, which is excellent in hair growth and regrowth promoting effect on human hair, and a hair growth promoting composition comprising the same as an active ingredient.

As a result of diligent studies of the inventors for attaining the above mentioned objects, it has been found that certain benzimidazole derivative and its salt have excellent hair growth and regrowth promoting effect, thereby accomplishing the present invention.

Namely, a benzimidazole derivative or a salt thereof in accordance with the present invention is expressed by the following Formula (I):

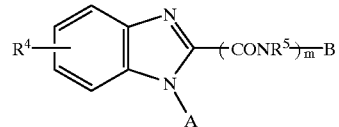

wherein each of A and B is $R^1$ or $-(CH_2)_n-NR^2R^3$, wherein when A is $R^1$, B is $-(CH_2)_n-NR^2R^3$ and when A is $-(CH_2)_n-NR^2R^3$, B is $R^1$;

$R^1$ is a hydrocarbon group of $C_{10-30}$;

$R^2$ and $R^3$ individually represent a hydrogen atom, a lower alkyl group, a phenyl group or a benzyl group, or $-NR^2R^3$ may be a heterocycle having 3–7 members; wherein when B is $-(CH_2)_n-NR^2R^3$ and m=1, $-(CONR^5)_m-B$ may be the following Group (W):

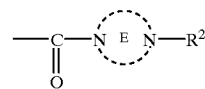

wherein $R^2$ is a hydrogen atom, a lower alkyl group, a phenyl group or a benzyl group and ring E is a heterocycle of 6 or 7 members;

$R^4$ is selected from the group consisting of a hydrogen atom, a halogen atom, a cyano group, a trifluoromethyl group, a lower alkyl group, a lower acyl group, a carboxyl group, a lower alkoxycarbonyl group, a carbamoyl group, a lower alkylcarbamoyl group, an amino group, a lower alkylamino group, a lower acylamino group, a hydroxy group, a lower alkoxy group and a lower acyloxy group;

$R^5$ is a hydrogen atom, a lower alkyl group, a lower acyl group or a lower alkylcarbamoyl group; wherein when B is $-(CH_2)_n-NR^2R^3$ and m=1, $-(CONR^5)_m-B$ may be said Group (W);

m is 0 or 1; and n is an integer of 0–5.

A hair growth promoting composition in accordance with the present invention is characterized by comprising said benzimidazole derivative or the pharmacologically acceptable salt thereof as an effective ingredient.

An external preparation for skin in accordance with the present invention is characterized by comprising said benzimidazole derivative or the pharmacologically acceptable salt thereof.

A method for promoting hair growth in accordance with the present invention is characterized by applying an effective amount of said benzimidazole derivative or the pharmacologically acceptable salt thereof on the skin of mammals and, in particular, on human scalp.

BRIEF DESCRIPTION OF THE DRAWINGS

FIGS. 1–3 and 5–12 show examples of steps for manufacturing the benzimidazole derivative in accordance with the present invention; and FIGS. 4 and 13 show examples of steps for manufacturing the starting material of the benzimidazole derivative in accordance with the present invention.

BEST MODE FOR CARRYING OUT THE INVENTION

Figure 1:
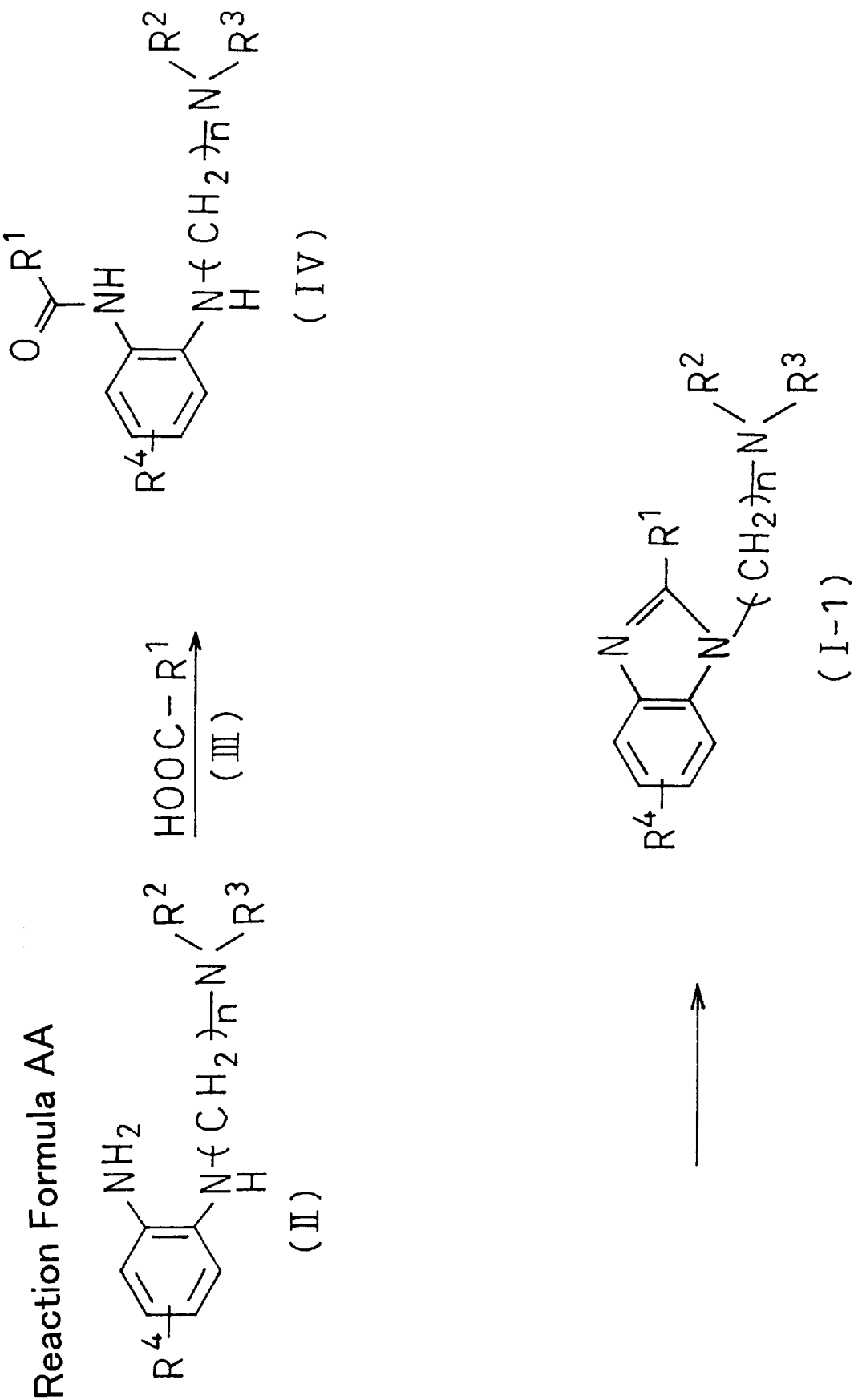

In the compound of the present invention, a hydrocarbon group of $C_{10-30}$ shown by $R^1$ refers to a straight or branched alkyl group having 10–30 carbon atoms, a straight or branched alkenyl group having 10–30 carbon atoms, a straight or branched alkynyl group having 10–30 carbon atoms, or an aromatic hydrocarbon group having 10–30 carbon atoms. Also, there may be one or two cycloalkyl rings having 3–8 carbon atoms at an optional position in $R^1$.

Examples of the above-mentioned straight alkyl group include decyl, undecyl, dodecyl, tridecyl, tetradecyl, pentadecyl, hexadecyl, heptadecyl, octadecyl, nonadecyl, icosyl, henicosyl, docosyl, tetracosyl, hexacosyl octacosyl and the like.

Examples of the above-mentioned branched alkyl group include 6-methyldecyl, 9-methyldecyl, 6-ethylnonyl, 5-propyloctyl, 11-methyldodecyl, 12-methyltridecyl, 4-methyltetradecyl, 13-methyltetradecyl, 14-ethylhexadecyl, 10-methyloctadecyl, 15-ethylheptadecyl, 10-methyldocosyl, 2-pentyloctadecyl, 22-methyltricosyl, 12-hexyloctadecyl, 6-methyltetracosyl, 24-methylheptacosyl, 2-decylhexadecyl, 2-nonyloctadecyl, 2-dodecyloctadecyl and the like.

Examples of the straight or branched alkenyl group having 10–30 carbon atoms and straight or branched alkynyl group having 10–30 carbon atoms include the alkenyl or alkynyl groups corresponding to the above-mentioned alkyl groups such as 4-decenyl, 7-dodecenyl, 9-octadodecenyl or 3-dodecynyl.

Examples of the aromatic hydrocarbon group having 10–30 carbon atoms include biphenylyl, 4-butylphenyl, naphtyl, and the like.

Also, examples of the hydrocarbon group having a cycloalkyl ring in $R^1$ include 12-cyclohexyldodecyl and the like.

Among these groups, $R^1$ is preferably a straight or branched alkyl group having 10–30 carbon atoms and, more preferably, a straight or branched alkyl group having 10–25 carbon atoms and, particularly preferably, a straight alkyl group having 13–21 carbon atoms. The hair growth effect tends to deteriorate in the case where the carbon number of $R^1$ is too small.

Each of $R^2$ and $R^3$, which may be identical or different from each other, can be a hydrogen, a lower alkyl, a phenyl or a benzyl group. Also, —$NR^2R^3$ may be a heterocycle having 3–7 members. Further, when B is —$(CH_2)_n$—$NR^2R^3$ and m=1, —$(CONR^5)_m$—B may be said Group (W).

In $R^2$ and $R^3$, the lower alkyl group refers to a straight or branched alkyl group having 1–6 carbon atoms. Examples of the lower alkyl group include methyl, ethyl, propyl, butyl, isopropyl, isobutyl, 1-methylpropyl, tert-butyl, pentyl, 1-ethylpropyl, isoamyl, hexyl and the like. For the lower alkyl group in $R^2$ and $R^3$, methyl or ethyl group is preferable. In the present invention, the definition of lower alkyl group is the same as mentioned above if there is no further description.

Also, the lower alkyl group in $R^2$ and $R^3$ may be substituted by one or two hydroxyl groups. Examples of such a hydroxy lower alkyl group include 2-hydroxyethyl group.

In $R^2$ and $R^3$, a phenyl and a benzyl group may be substituted by one or two of the same or different substituents, which can be selected from the group consisting of a halogen, a lower alkyl, a lower acyl, a nitro, a cyano, a lower alkoxycarbonyl, a lower alkylamino, a lower alkoxy and a lower acyloxy group. The definition of each substituent referred in here is explained as follows:

The halogen atom represents chlorine, bromine, iodine or fluorine.

The lower alkyl group is as mentioned above and, preferably, methyl or ethyl group.

The lower acyl group is a straight or branched acyl group having 2–7 carbon atoms. Examples of the lower acyl group include acetyl, propionyl, butyryl, isobutyryl, pivaloyl, benzoyl group and the like.

The lower alkoxycarbonyl group represents a carboxyl group whose hydrogen atom is substituted by a lower alkyl group. A preferable example of the lower alkoxycarbonyl group is methoxycarbonyl or ethoxycarbonyl group.

The lower alkylamino group represents an amino group whose hydrogen atom is substituted by one or two of the same or different lower alkyl groups. A preferable example of the lower alkylamino group is methylamino or dimethylamino group.

The lower alkoxy group represents a hydroxyl group whose hydrogen atom is substituted by a lower alkyl group. A preferable example of the lower alkoxy group is methoxy or ethoxy group.

The lower acyloxy group represents a hydroxyl group whose hydrogen atom is substituted by a lower acyl group, wherein said lower acyl group is as above-mentioned. A preferable example of the lower acyloxy group is acetoxy or propionyloxy group.

The heterocycle having 3–7 members of —$NR^2R^3$ represents a saturated or unsaturated heterocycle containing nitrogen atom to which $R^2$ and $R^3$ are bonded. In addition to the nitrogen atom, a hetero atom such as nitrogen, oxygen, or sulfur atom may be contained in the heterocycle. Examples of the heterocycle include aziridine, azetidine, pyrrolidine, piperidine, homopiperidine, piperazine, morpholine, pyrrole, pyrazole, imidazole, thiomorpholine, thiazole, and thiazolidine ring. Among these heterocycles, pyrrolidine, piperidine, piperazine, morpholine, imidazole, thiomorpholine, thiazole, or thiazolidine ring is preferable. The heterocycle may be substituted by one or two of the same or different substituent, which can be selected from the group consisting of a lower alkyl, a lower alkoxy, a lower acyl and a nitro group. The lower alkyl group is preferably methyl or ethyl group. The lower alkoxy group is preferably methoxy or ethoxy group. The lower acyl group is preferably acetyl or propionyl group.

In said Group (W), the ring E is a saturated or unsaturated heterocycle having 6 or 7 members containing two nitrogen atoms and, preferably, a saturated heterocycle. Preferable examples of Group (W) include the following Group (a) and (b):

(a)
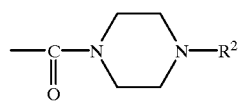

(b)
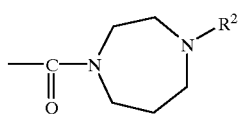

wherein $R^2$ is a hydrogen atom, a lower alkyl group, a phenyl group, or a benzyl group. Group (a) is more preferable for Group (W). $R^2$ of Group (W), (a) and (b) is preferably lower alkyl group and, more preferably, methyl group.

In the present invention, when A is —$(CH_2)_n$—$NR^2R^3$, it is preferable that $R^2$ and $R^3$ are lower alkyl groups, or —$NR^2R^3$ is a heterocycle having 3–7 members. When B is —$(CH_2)_n$—$NR^2R^3$, it is preferable that: $R^2$ and $R^3$ are lower alkyl groups; —$NR^2R^3$ is a heterocycle having 3–7 members; or $R^2$ and $R^3$ form a part of said Group (W).

$R^4$ can be a hydrogen atom, a halogen atom, a cyano group, a trifluoromethyl group, a lower alkyl group, a lower acyl group, a carboxyl group, a lower alkoxycarbonyl group, a carbamoyl group, a lower alkylcarbamoyl group, an amino group, a lower alkylamino group, a lower acylamino group, a hydroxy group, a lower alkoxy group or a lower acyloxy group.

As for $R^4$, the definitions for halogen, lower alkyl, lower acyl, lower alkoxycarbonyl, lower alkylamino, lower alkoxy and lower acyloxy groups are identical to those in $R^2$ and $R^3$.

The lower alkylcarbamoyl group in $R^4$ represents a carbamoyl group whose hydrogen atom is substituted by one or two of the same or different lower alkyl groups.

The lower acylamino group in $R^4$ represents an amino group whose hydrogen atom is substituted by one or two of the same or different lower acyl groups. The lower acyl group is as mentioned above.

Among them, $R^4$ is preferably a hydrogen atom, a halogen atom, an amino group, a lower alkyl group, a lower alkylcarbamoyl group or a lower alkoxycarbonyl. More preferably, it is a hydrogen, chlorine, amino, methyl, dimethylcarbamoyl, methylcarbamoyl, ethoxycarbamoyl.

$R^5$ can be a hydrogen atom, a lower alkyl group, a lower acyl group or a lower alkylcarbamoyl group. Also, when B is —$(CH_2)_n$—$NR^2R^3$ and m=1, —$(CONR^5)_m$—B may be said Group (W). Preferably, $R^5$ is a hydrogen atom or forms a part of Group (W).

As for $R^5$, the definitions for lower alkyl and lower acyl groups are identical to those in $R^2$ and $R^3$ and the definition for lower alkylcarbamoyl group is identical to that in $R^4$.

In the present invention, m can be 0 or 1. When A is —$(CH_2)_n$—$NR^2R^3$ and B is $R^1$, m is preferably 0.

On the other hand, when A is $R^1$ and B is —$(CH_2)_n$—$NR^2R^3$, m is preferably 1. In this case, it is preferable that $R^5$ is a hydrogen atom, or —$CONR^5$—$(CH_2)_n$—$NR^2R^3$ is said Group (W).

n is an integer of 0–5 and, preferably, an integer of 2–5.

The Compound (I) of the present invention may have a asymmetric carbon therein. In addition to optical isomers based on the asymmetric carbon, the present invention can include the other isomers such as geometrical isomers or conformational isomers, and also can comprise the mixture thereof.

The Compound (I) provided in the present invention can be manufactured by using well-known reactions. The representative synthetic examples will be shown in the following. Also, in the following manufacturing methods, $R^1$, $R^2$, $R^3$, $R^4$, $R^5$ and n are the same as shown in the definitions of Formula (I), unless otherwise indicated.

COMPOUND (I-1) (A=—$(CH_2)_n$—$NR^2R^3$, B=$R^1$, m=0)

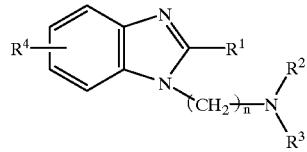

(I-1)

Figure 2:
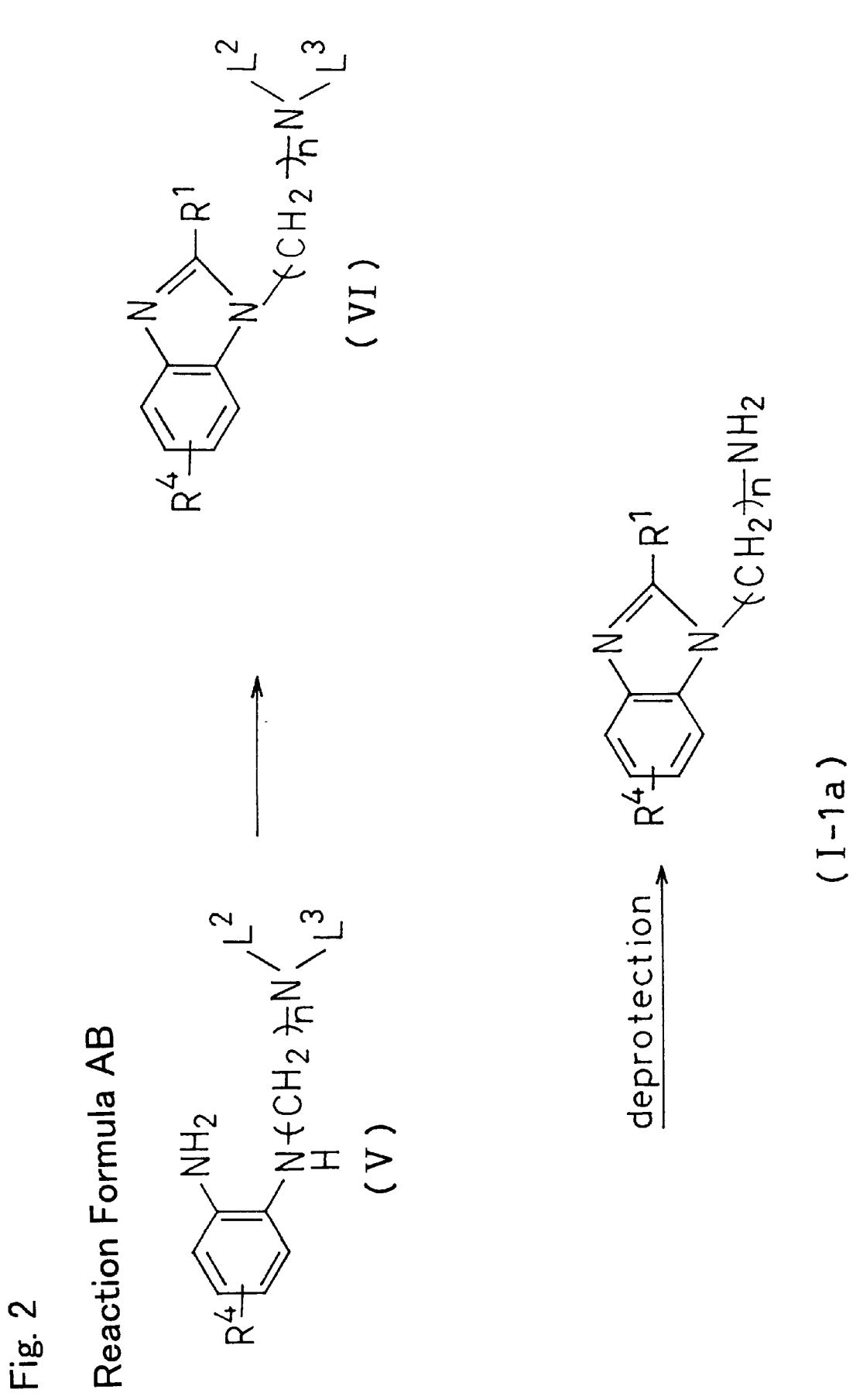
Figure 3:
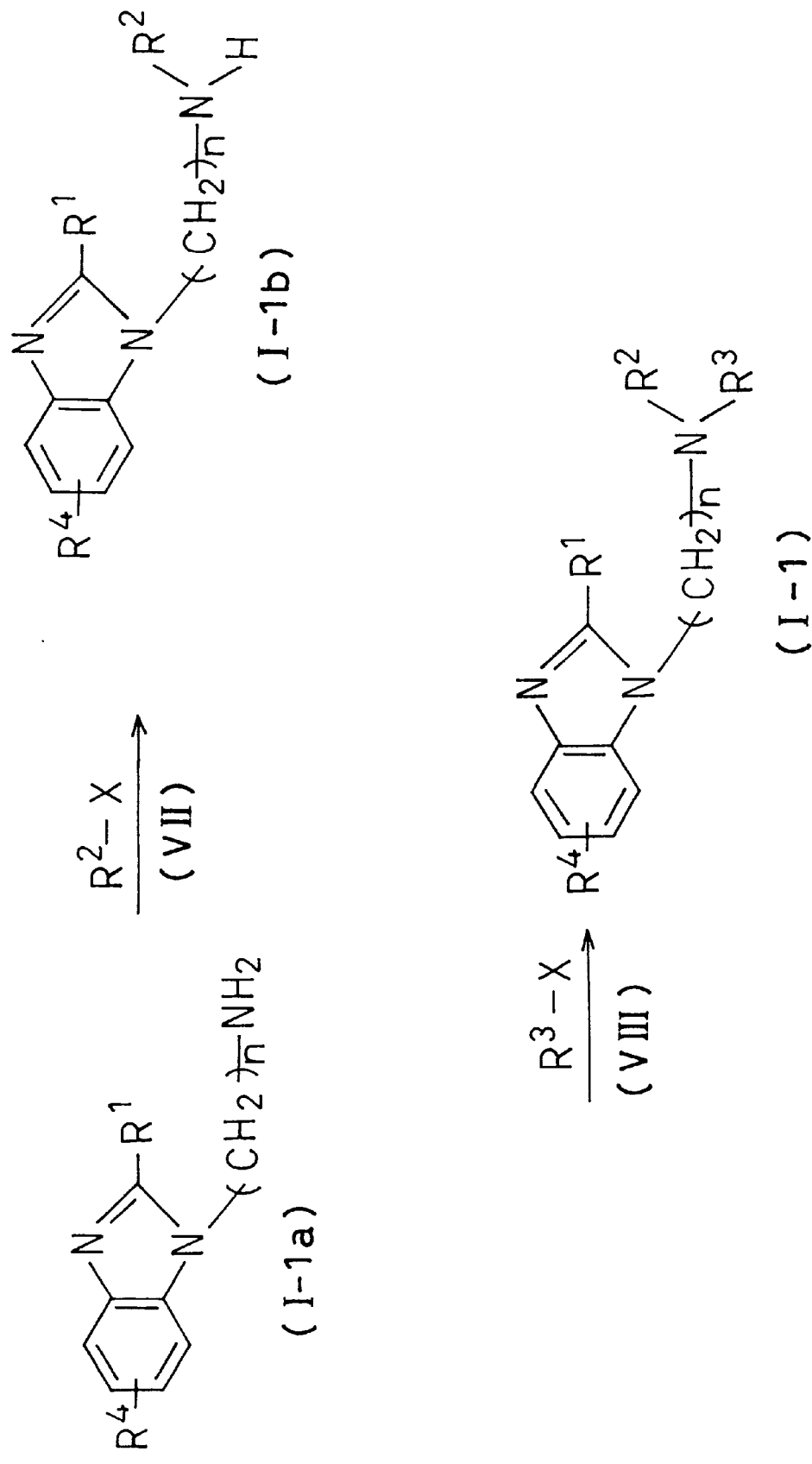
Figure 4:
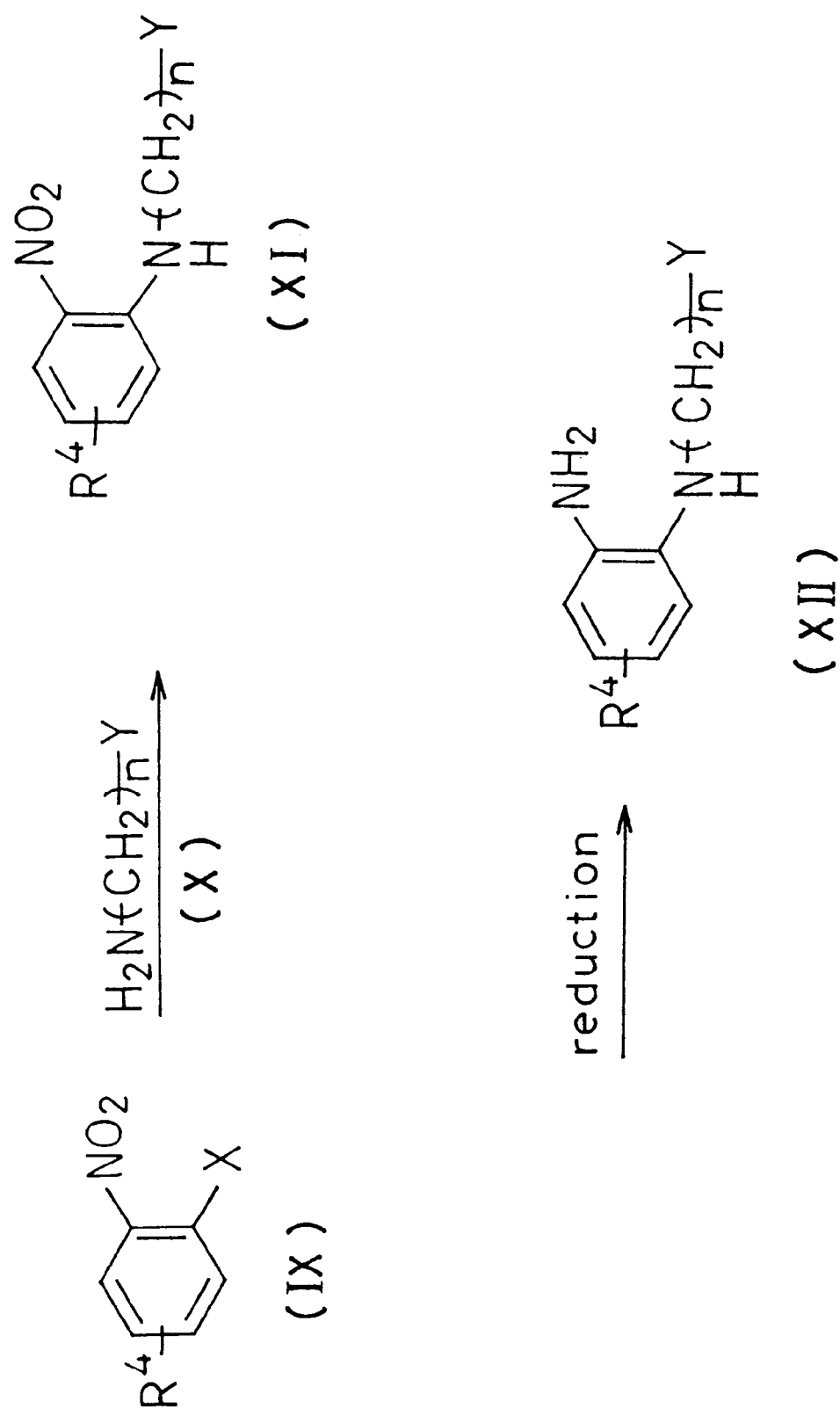

Compounds (I-1) of the present invention can be synthesized as shown in Reaction Formulae AA to AC of FIGS. 1 to 3.

In Reaction Formula AA, an amide (IV) is synthesized from an amine (II) and a carboxylic acid (III), and then the amide (IV) is intramolecular condensed to give Compound (I-1).

At the first step of Reaction Formula AA, known amide-bond forming reactions such as a mixed anhydride method, an acid chloride method, DCC method, CDI method, an azide method, and the like can be used.

In the mixed anhydride method, an activator such as ethyl chloroformate, isobutyl chloroformate, pivaloyl chloride, diphenylphosphinic chloride, or phosphorus oxychloride is used to convert the carboxylic acid (III) into its corresponding acid anhydride, and then the latter and the amine (II) are reacted. As an additive, for example, an organic base such as triethylamine, pyridine, or N-methylmorpholine can be used. As a solvent, for example, a halogenated hydrocarbon such as dichloromethane or chloroform; an aromatic compound such as benzene, toluene, xylene, or pyridine; an ether such as tetrahydrofuran or 1,4-dioxane; an amide such as N,N-dimethylformamide or N,N-dimethylacetamide; or dimethylsulfoxide can be used. While the reaction temperature and reaction time may be changed according to the starting materials used, the reaction is usually effected at a temperature within the range of −15° C. to the reflux temperature of the solvent.

In the acid chloride method, for example, phosphorus pentachloride, phosphorus trichloride, or thionyl chloride is used to convert the carboxylic acid (III) into its corresponding acid chloride, and then the latter and the amine (II) are reacted. As an additive, for example, an organic base such as triethylamine, pyridine, or N-methylmorpholine can be used. As a solvent, for example, a halogenated hydrocarbon such as dichloromethane or chloroform; an aromatic compound such as benzene, toluene, xylene, or pyridine; an ether such as diethyl ether, tetrahydrofuran, or 1,4-dioxane; an amide such as N,N-dimethylformamide or N,N-dimethylacetamide; a sulfoxide such as dimethylsulfoxide; or the mixture thereof can be used. While the reaction temperature and reaction time may be changed according to the starting materials used, the reaction is usually effected at a temperature within the range of 0° C. to the reflux temperature of the solvent.

In the DCC method, as a condensing agent, N,N'-dicyclohexylcarbodiimide (DCC), 1-ethyl-3-(3-dimethylaminopropyl)carbodiimide hydrochloride (WSCI) and the like can be used. As a solvent, for example, a halogenated hydrocarbon such as dichloromethane or chloroform; an aromatic hydrocarbon such as benzene, toluene, or xylene; an ether such as tetrahydrofuran or 1,4-dioxane; or an amide such as N,N-dimethylformamide or N,N- dimethylacetamide can be used. If necessary, this reaction may be effected while 1-hydroxy benzotriazole (HOBt) or N-hydroxysuccinimide (HOSu) is added thereto. While the reaction temperature and reaction time may be changed according to the starting materials used, the reaction is usually effected at a temperature within the range of 0° C. to the reflux temperature of the solvent.

In the CDI method, for example, an activator such as N,N'-carbonyldiimidazole is used to convert the carboxylic acid (III) into its N-acyl derivative, and then the latter and the amine (II) are reacted. As an additive, for example, an organic base such as triethylamine, pyridine or N-methylmorpholine, or an inorganic base such as sodium hydride or potassium hydride can be used. As a solvent, for example, a halogenated hydrocarbon such as dichloromethane or chloroform; an aromatic hydrocarbon such as benzene, toluene, or xylene; an ether such as tetrahydrofuran or 1,4-dioxane; or an amide such as N,N-dimethylformamide or N,N-dimethylacetamide can be used. While the reaction temperature and reaction time may be changed according to the starting materials used, the reaction is usually effected at a temperature within the range of 0° C. to the reflux temperature of the solvent.

In the azide method, for example, an activator such as diphenylphosphorylazide is used to convert the carboxylic acid (III) into its corresponding azide, and then the latter and the amine (II) are reacted. As an additive, for example, an organic base such as triethylamine, pyridine, or N-methylmorpholine can be used. As a solvent, for example, a halogenated hydrocarbon such as dichloromethane or chloroform; an aromatic hydrocarbon such as benzene, toluene or xylene; an ether such as tetrahydrofuran or 1,4-dioxane; or an amide such as N,N-dimethylformamide or N,N-dimethylacetamide can be used. While the reaction temperature and reaction time may be changed according to the starting materials used, the reaction is usually effected at a temperature within the range of 0° C. to the reflux temperature of the solvent.

In the intramolecular condensation at the second step of Reaction Formula AA, an acidic catalyst is usually used. For example, concentrated hydrochloric acid, nitric acid, hydrobromic acid, or the like can be used therefor. As a solvent, for example, an alcohol such as methanol or ethanol can be used. While the reaction temperature and reaction time may be changed according to the starting materials used, the reaction is usually effected at a temperature within the range of room temperature to the reflux temperature of the solvent.

In Reaction Formula AB, Compound (VI) is synthesized from an amine (VI), and then Compound (VI) is deprotected to give Compound (I-1a) wherein $R^2$ and $R^3$ of Compound (I-1) are hydrogen atoms. In Reaction Formula AB, either $L^2$ or $L^3$ is an amino protecting group i.e., an urethane type protecting group such as tert-butyloxycarbonyl group, benzyloxycarbonyl group or 9-fluorenylmethyloxycarbonyl group; a sulfonyl type protecting group such as 2-(trimethylsilyl)ethanesulfonyl group; a sulfenyl type protecting group such as 2,2,2-trifluoro-1,1-diphenylethanesulfenyl group; or an alkyl type protecting group such as benzyl group, trityl group or 9-phenylfluorenyl group, while the other is a hydrogen atom. Also, $L^2$ and $L^3$ together form a phthalimide type amino protecting group. Further, the other amino protecting groups can be used as long as the protecting group is not opposed to the object of the present Reaction Formula. The definitions of $L^2$ and $L^3$ are the same in the following.

The reaction at the first step of Reaction Formula AB can be effected by a method according to Reaction Formula AA.

In the deprotection reaction at the second step, various known methods can be used according to the kinds of amino protecting groups $L^2$ and $L^3$. Specifically, for example, when $L^2$ is tert-butoxycarbonyl group and $L^3$ is a hydrogen atom, by using hydrogen fluoride in a solvent such as glacial acetic acid, the reaction is effected at the temperature within a range of room temperature to the reflux temperature of the solvent, thereby attaining the aimed object. Also, when a phthalimide amino protecting group that is formed by $L^2$ and $L^3$ together is used, by using hydrazine as a deprotecting agent, the reaction is effected in ethanol at a temperature within the range of room temperature to the reflux temperature of the solvent, thereby attaining the aimed object.

In Reaction Formula AC, Compound (I-1a) and approximately one-equivalent amount of halide (VII) are reacted in the presence of a base to give Compound (I-b). Similarly, Compound (I-1b) and halide (VIII) are reacted to give Compound (I-1). X represents a halogen atom and the definition of X is the same in the following.

In this reaction, when $R^2$ or $R^3$ is a lower alkyl, phenyl or benzyl group, an inorganic base such as potassium carbonate, potassium hydroxide, sodium hydroxide or sodium hydride, or an organic base such as triethylamine or pyridine can be used as a base. Specifically, for example, by using potassium carbonate as a base, the reaction is effected in a solvent such as acetone or N,N-dimethylformamide at the temperature within a range of room temperature to the reflux temperature of the solvent, thereby attaining the aimed object.

Also, in a similar manner to this Reaction Formula AC, Compound (I-1a) and two-equivalent amount of halide (VII) are reacted in the presence of a base to give the compound wherein $R^2$ and $R^3$ of Compound (I-1) are the same. Also, Compound (I-1a) and the corresponding dihalogenated compound are reacted to give the compound wherein $-NR^2R^3$ of Compound (I-1) is a heterocyclic having 3–7 members.

The amine (II) and (V) which are starting materials of Reaction Formulae AA and AB respectively can be synthesized as shown in Reaction Formula AD. Namely, Compound (XI) is synthesized from Compound (IX) and an amine (X), and then a nitro group of Compound (XI) is reduced to give the materials. In Reaction Formula AD, Y represents $-NR^2R^3$ or $-NL^2L^3$.

Although the reaction at the first step of Reaction Formula AD is usually effected in the presence of a base, excess amount of the amine (X) may be used in place of addition of the base. As a base, for example, an inorganic base such as potassium carbonate, potassium hydroxide, sodium hydroxide or sodium hydride, or an organic base such as triethylamine or pyridine can be used. As a solvent, toluene, ether, tetrahydrofuran, chloroform, dichloromethane, acetone, N,N-dimethylformamide or the like can be used. Also, the reaction can be effected without the solvent. While the reaction temperature and reaction time may be changed according to the starting materials used, the reaction is usually effected at a temperature within the range of room temperature to the reflux temperature of the solvent. Specifically, for example, the amine (X) is added to a solution containing Compound (IX) in pyridine and the mixture is reacted at a temperature within the range of room temperature to 150° C., thereby attaining the aimed object.

The reduction reaction at the second step of Reaction Formula AD, for example, can be effected by catalytic reduction using palladium-carbon as a catalyst, or a reduction using a tin compound such as metallic tin or tin chloride. The catalytic reduction is usually effected in a solvent such as methanol, ethanol or ethyl acetate under a normal pressure or more. The reduction using a tin compound is usually effected in a acidic condition with hydrochloric acid or the like. In each case, while the reaction temperature and reaction time may be changed according to the starting materials used, the reaction is usually effected at a temperature within the range of 0° C. to the reflux temperature of the solvent.

(2) COMPOUND (I-2) (A=$R^1$, B=—$(CH_2)_n$—$NR^2R^3$, m=0)

(I-2)

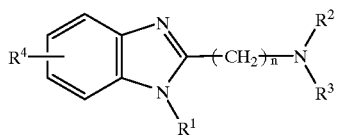

Figure 5:
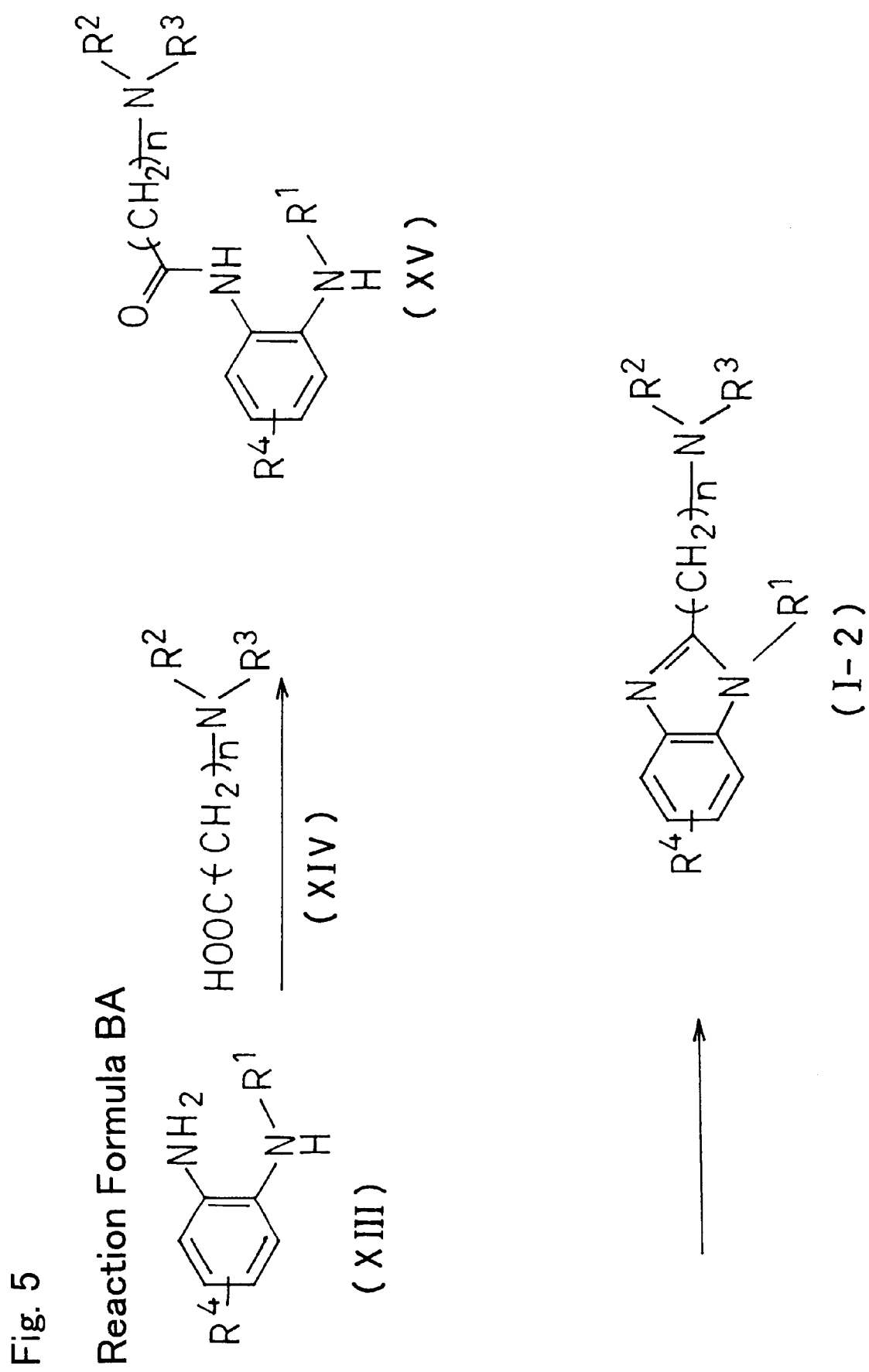
Figure 7:
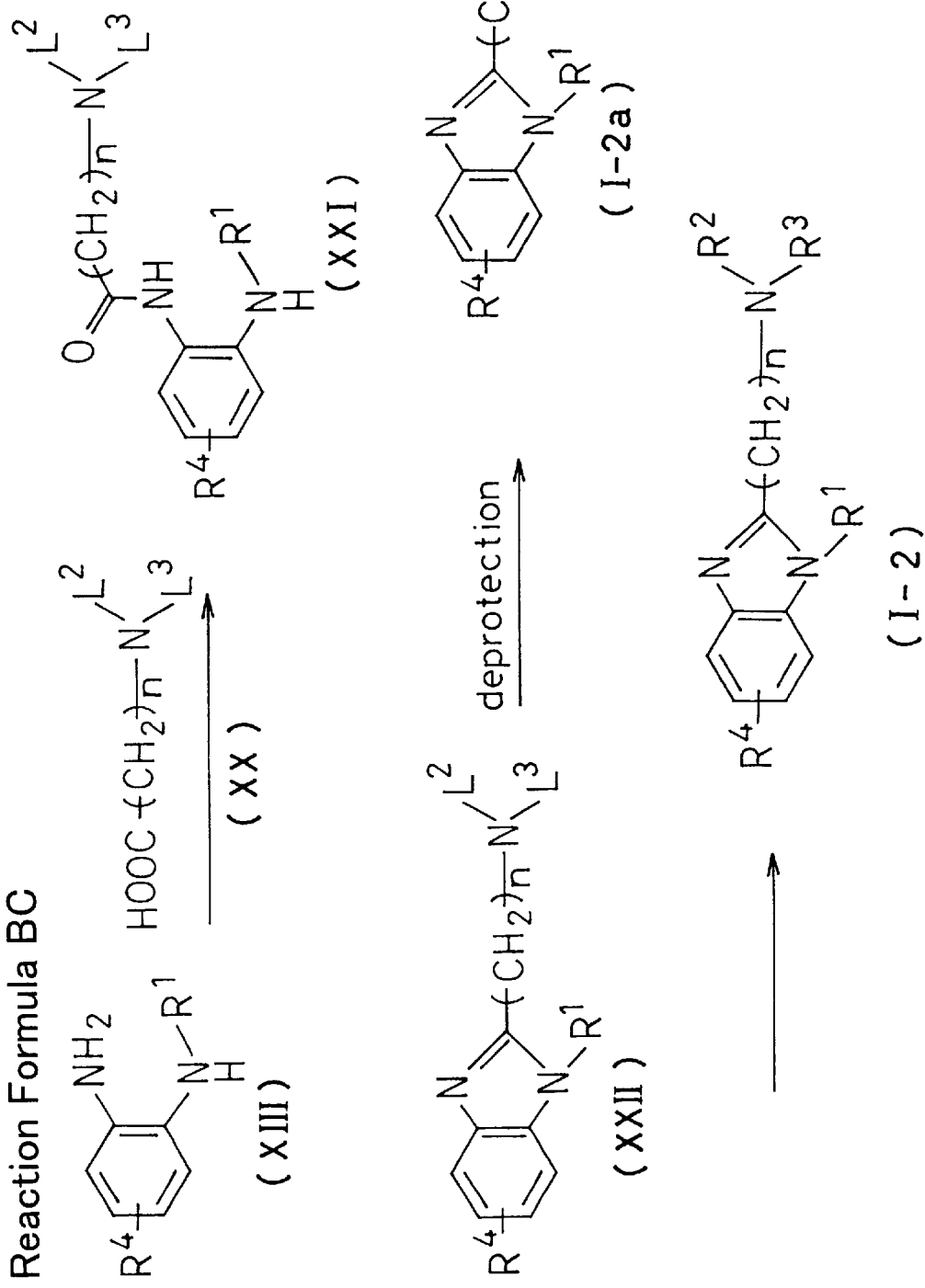

Compound (I-2) of the present invention can be synthesized as shown in Reaction Formulae BA to BC of FIGS. 5 to 7.

In Reaction Formula BA, an amide (XV) is synthesized from an amine (XIII) and a carboxylic acid (XIV), and then the amide (XV) is intramolecular condensed to give Compound (I-2). This reaction can be effected by a method according to Reaction Formula AA.

In Reaction Formula BB, Compound (I-2) can be synthesized as follows: first, an amide (XVII) is synthesized from the amine (XIII) and a carboxylic acid (XVI); second, the amide (XVII) is intramolecular condensed to produce Compound (XVIII); and finally, Compound (XVIII) and a amine (XIX) are reacted to give Compound (I-2). In Reaction Formula BB, $L^1$ means a group that can be easily substituted with nitrogen. For example, a halogen atom, tosyloxy group, mesyloxy group or the like can be used therefor. The definition of $L^1$ is the same in the following.

The first and second steps of Reaction Formula BB can be effected by a method according to Reaction Formula AA. The reaction of the third step can be effected by a method according to Reaction Formula AD.

Also, Compound (I-2a) wherein $R^2$ and $R^3$ of Compound (I-2) are hydrogen atoms can be synthesized as shown in Reaction Formula BC. Namely, first, an amide (XXI) is synthesized from the amine (XIII) and a carboxylic acid (XX); second, the amide (XXI) is intramolecular condensed to produce Compound (XXII); and finally, Compound (XXII) is deprotected to give Compound (I-2a). Further, Compound (I-2a) can be introduced into Compound (I-2) by a method according to Reaction Formula AC. The reactions at the first and second steps of Reaction Formula BC can be effected by a method according to Reaction Formula AA. The deprotection reaction at the third step can be effected by a method according to the second step of Reaction Formula AB.

Compound (XIII) which is a starting material in Reaction Formulae BA to BC can be synthesized by a reaction in a similar manner to Reaction Formula AD except for using an amine $H_2N$—$R^1$ in place of the amine (X).

(3) COMPOUND (I-3) (A=—$(CH_2)_n$—$NR^2R^3$, B=$R^1$, m=1)

(I-3)

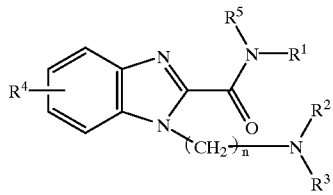

Figure 8:
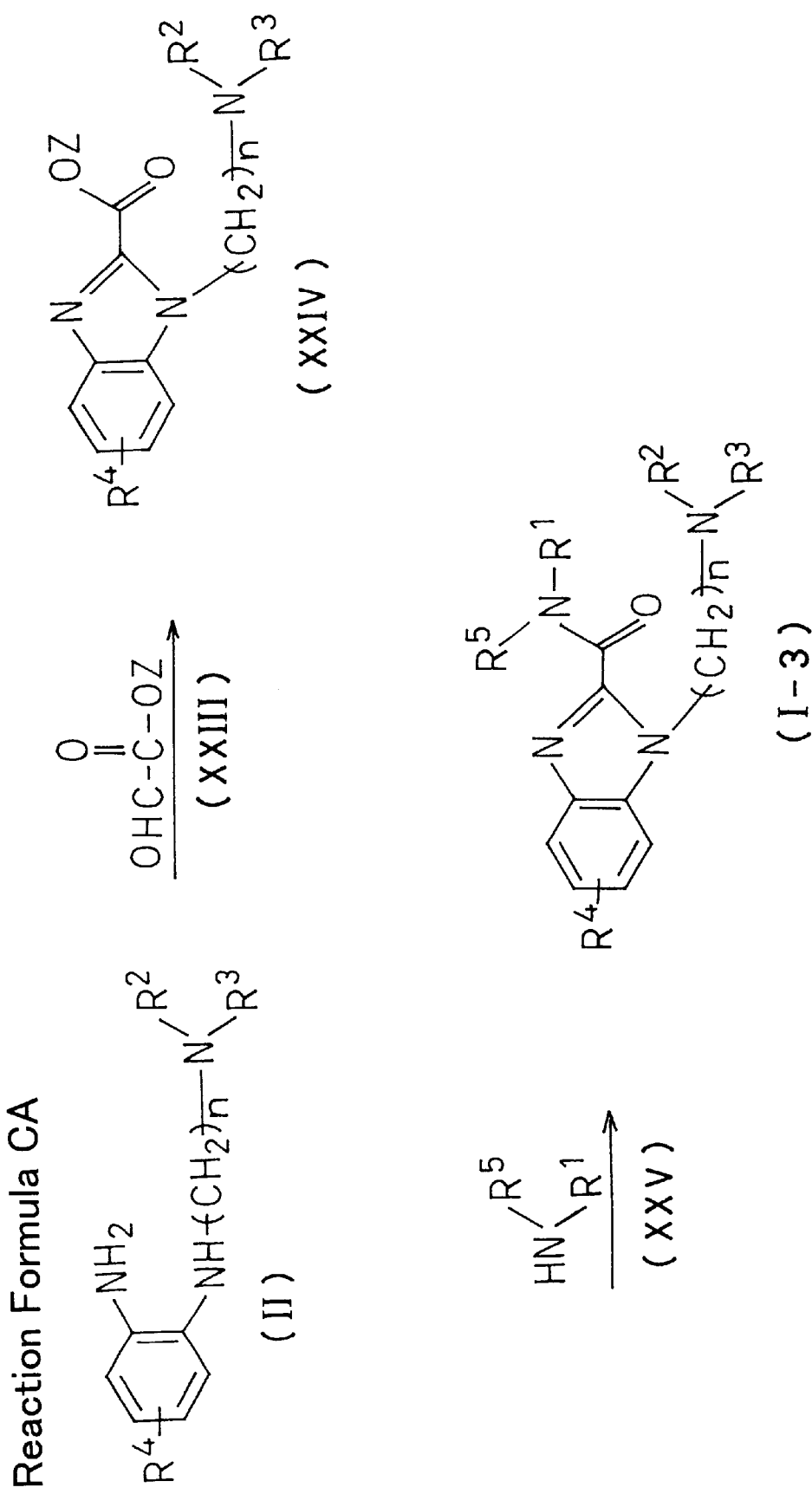
Figure 9:
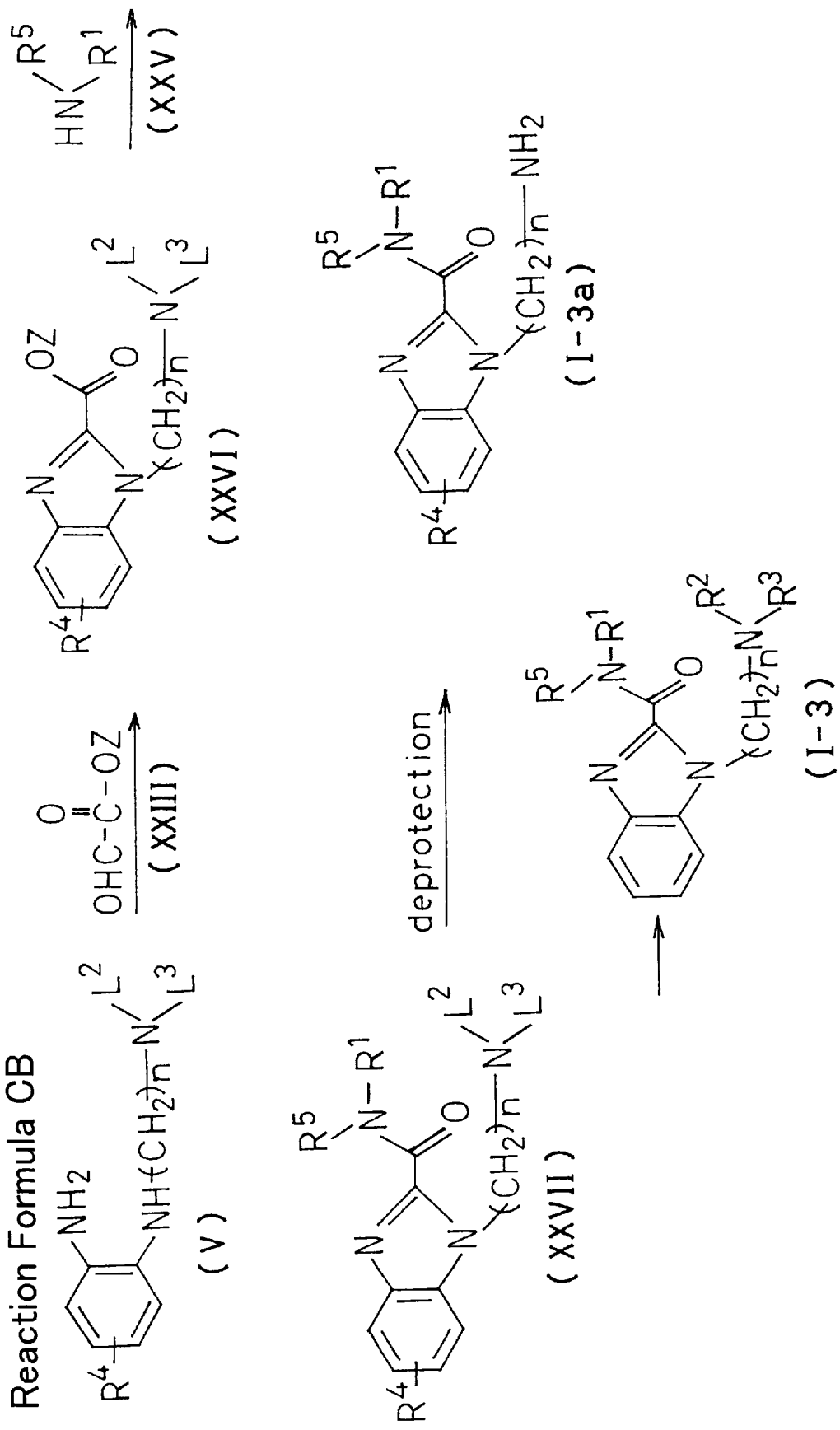

Compound (I-3) of the present invention can be synthesized as shown in Reaction Formulae CA and CB of FIGS. 8 and 9. In these Reaction Formulae, Z means a alkyl group such as methyl or ethyl. The definition of Z is the same in the following.

In Reaction Formula CA, Compound (XXIV) is synthesized from the amine (II), and then Compound (XXIV) and an amine (XXV) are reacted to give Compound (I-3).

The reaction at the first step of Reaction Formula CA can be effected by a reaction of the amine (II) with a glyoxalate (XXIII) in the presence of iodide or the like. As a solvent, for example, an alcohol such as methanol or ethanol can be used. While the reaction temperature and reaction time may be changed according to the starting materials used, the reaction is usually effected at a temperature within the range of room temperature to the reflux temperature of the solvent.

The reaction at the second step of Reaction Formula CA can be effected in the absence or presence of a solvent such as chloroform or dichloromethane at a temperature within the range of room temperature to 200° C. Preferably, it is effected in the absence of the solvent at 70 to 200° C.

In Reaction Formula CB, Compound (XXVI) is synthesized from the amine (V), and then Compound (XXVI) and the amine (XXV) are reacted to produce Compound (XXVII). Compound (XXVII) is deprotected to give Compound (I-3a) wherein $R^2$ and $R^3$ of Compound (I-3) are hydrogen atoms. Further, Compound (I-3a) can be introduced into Compound (I-3) by a method according to Reaction Formula AC.

The reactions at the first and second steps of Reaction Formula CB can be effected by a method according to Reaction Formula CA. The deprotection reaction at the third step can be effected by a method according to the second step of Reaction Formula AB.

(4) COMPOUND (I-4) (A=$R^1$, B=—$(CH_2)_n$—$NR^2R^3$, m=1)

(I-4)

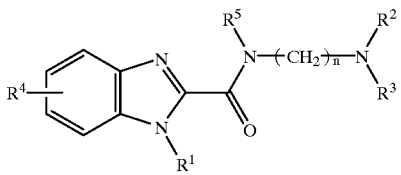

Figure 11:
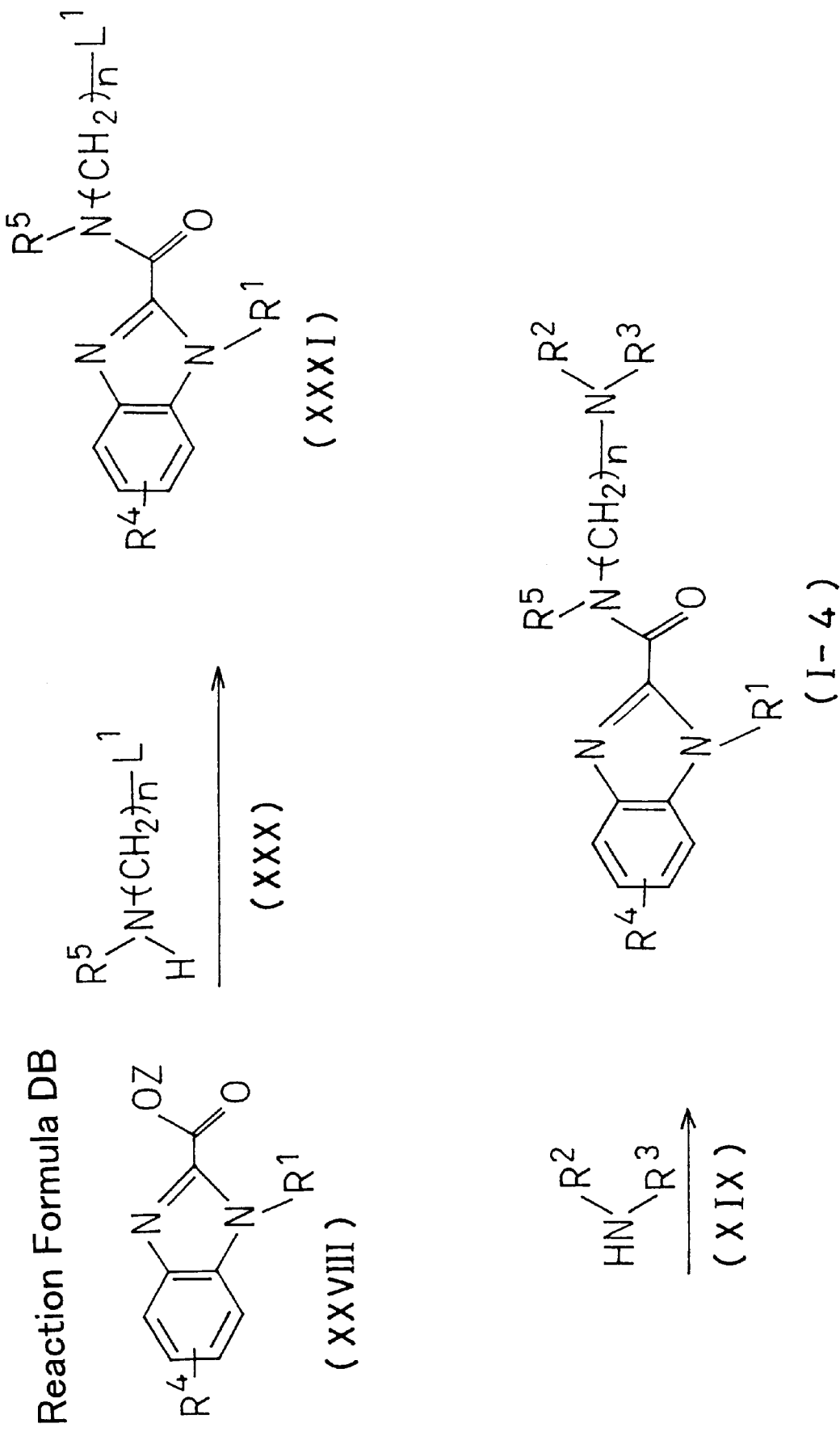
Figure 12:
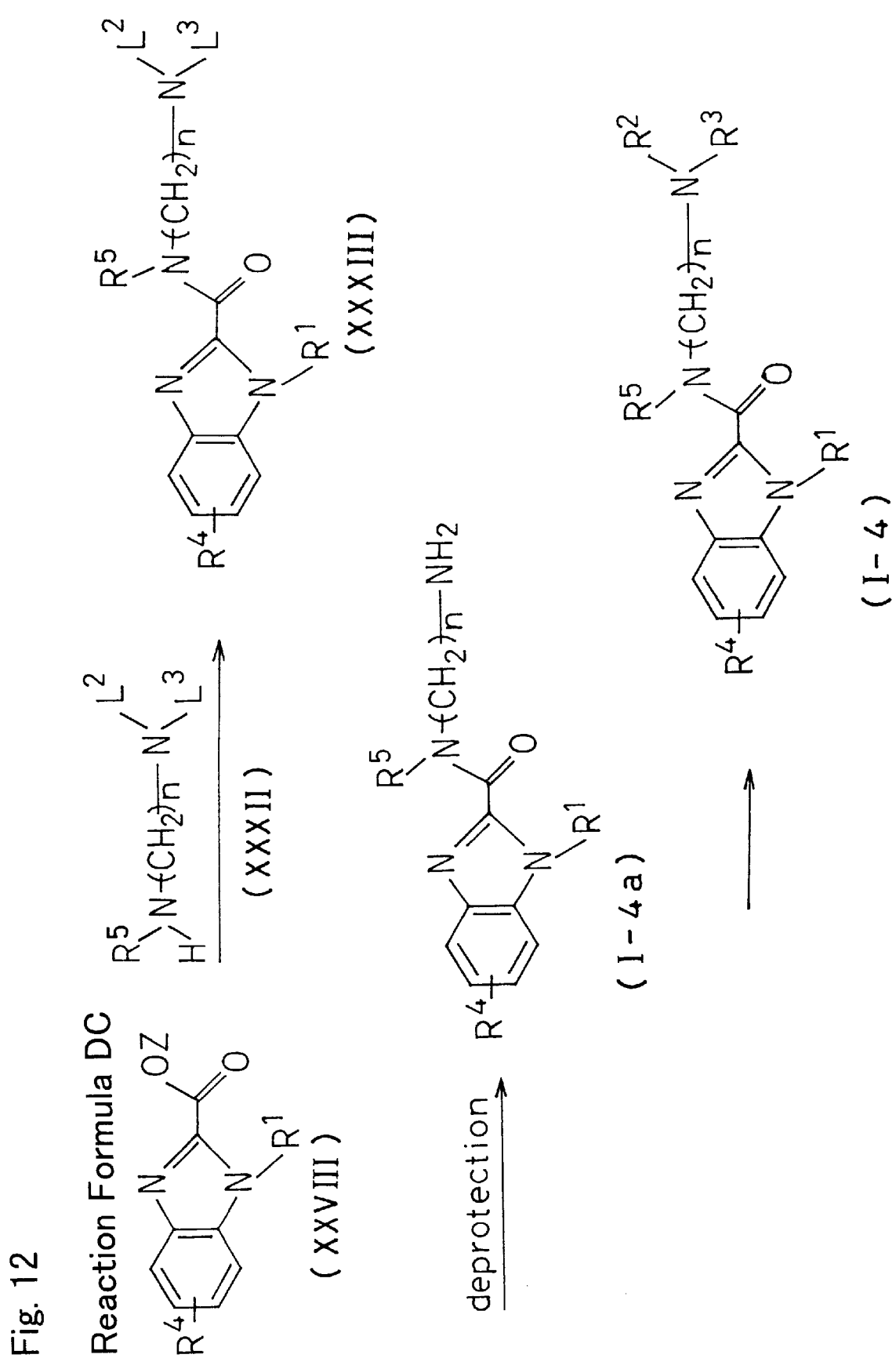

Compound (I-4) of the present invention can be synthesized as shown in Reaction Formulae DA to DC of FIGS. 10 to 12.

In Reaction Formula DA, Compound (I-4) can be obtained from Compound (XXVIII) and an amine (XXIX). This reaction can be effected by a method according to the second step of Reaction Formula CA.

In Reaction Formula DB, Compound (XXXI) is synthesized from Compound (XXVIII) and an amine (XXX), and then Compound (XXXI) and the amine (XIX) are reacted to give Compound (I-4). The first step of Reaction Formula DB can be effected by a method according to the second step of Reaction Formula CA. The second step of Reaction Formula DB can be effected by a method according to the third step of Reaction Formula BB.

In Reaction Formula DC, Compound (XXXIII) is synthesized from Compound (XXVIII) and an amine (XXXII), and then Compound (XXXIII) is deprotected to give Compound (I-4a) wherein $R^2$ and $R^3$ of Compound (I-4) are hydrogen atoms. Further, Compound (I-4a) can be introduced into Compound (I-4) by a method according to Reaction Formula AC.

The reaction at the first step of Reaction Formula DC can be effected by a method according to the second step of Reaction Formula CA. The deprotection reaction at the second step can be effected by a method according to the second step of Reaction Formula AB.

The starting material (XXVIII) of Reaction Formulae DA to DC, for example, can be synthesized by a method according to the first step of Reaction Formula CA from Compound (XIII) as shown in Reaction Formula DD of FIG. 13.

Among the starting materials used in the foregoing Reaction Formulae, materials which are not described above are commercially available or can be easily synthesized from a suitable starting material by using known methods.

The benzimidazole derivative (I) provided in the present invention can be changed to an acid-added salt if necessary. Examples of the acid-added salt include salt with an inorganic acid such as hydrochloric acid, hydrobromic acid, sulfuric acid or phosphoric acid and salts with an organic acid such as acetic acid, propionic acid, citric acid, lactic acid, oxalic acid, maleic acid, fumaric acid, succinic acid, tartaric acid or methanesulfonic acid. These salts can be easily manufactured by common methods.

The benzimidazole derivatives in accordance with the present invention, which mechanism of action has not been made clear, have an excellent hair growth and regrowth promoting effect. Accordingly, by applying the compound on skin of mammals such as human scalp, care, improvement, or prevention of hair loss can be expected.

The benzimidazole derivative of the present invention can apply to pathological alopecia such as *alopecia areata, alopecia pityrodes* or *alopecia seborrheica* in addition to thin hair or hair loss what is called male pattern baldness or androgenic alopecia. The dosage of the benzimidazole derivative in accordance with the present invention must be determined suitably according to sex, age and degree of symptom in hair loss or thin hair. Usually 0.01–20 mg/cm$^2$ is applied on scalp per day for an adult in a single dose or several doses.

When the benzimidazole derivative of the present invention is used as a drug, quasi-drug or cosmetic for hair growth and regrowth promoting and prevention of hair loss, its pharmaceutical form can be selected voluntarily as long as the effects of the present invention can be exhibited. Examples of the pharmaceutical form include tonic, lotion, milky lotion, cream, ointment, gel, spray, mousse and the like. In addition to the benzimidazole derivative in accordance with the present invention, various pharmaceutically acceptable ingredients, which are generally compounded to hair growth promoting composition in the field of drug, quasi-drug and cosmetic, can be compounded to these preparations.

For example, as a drug having a blood flow promoting action, swertia herb extract, vitamin E and derivatives thereof, nicotinates such as benzyl nicotinate, and the like can be used. Examples of drugs which promote blood circulation by topical stimulation include capsicum tincture, cantharides tincture, camphor and vanillic acid nonylamide. Examples of drugs having hair follicle activating action include hinokitiol, placental extract, photosensitizing dye, pantothenic acid and derivatives thereof. Examples of drugs having antiandrogen action include a hormone such as estradiol or estrone. Examples of drugs having antiseborrheic action include sulfur, thioxolone and vitamin $B_6$.

In addition, salicylic acid, resorcine and the like which has corneocycle desquamating and antibacterial action can be compounded therein so as to prevent the generation of dandruff. Also, glycyrrhizic acid and derivatives thereof, menthol, and the like can be compounded therein so as to prevent inflammation of scalp. Further, an amino acid such as serine, methionine or arginine, a vitamin such as biotin, extracts of crude drugs and the like can be compounded therein in order to supplement nutrition for hair follicle and activate enzyme activity.

Also, extracts from plants such as althea, coix, peppermint, leaf base, capsicum, aloe, lycium, mugwort, oryza, seashore vitex, *rosmarinus officinalis*, drynaria, *cytisus scoparius*, gentiana, *salviae miltiorrhizeae radix*, sponge gourd, platycodon, pinus, sophora root, Japanese angelica root, safflower, Japanese barberny, areca, eucalyptus, prunella spike, akebiai stem, achyranthes root, bupleurum root, tea, licorice, hop, Chrysanthemum, senega, sesame, *cnidium rhizome*, cashew, pueraria root, *rosae rugosae flos*, saffron, rosemary, rehmannia root, or mallow can be compounded.

Also, a vasodilator such as alkoxycarbonylpyridine N-oxide, carpronium chloride or acetylcholine derivative; a cutaneous hyperfunctioning agent such as cephalanthin; an antibacterial agent such as hexachlorophene, benzalkonium chloride, cetylpyridinium chloride, undecylenic acid, trichlorocarbanilide or bithionol; zinc and its derivatives; lactic acid and its alkyl ester; an organic acid such as citric acid; a protease inhibitor such as tranexamic acid; and the like can be compounded.

Further, an alcohol such as ethanol or isopropanol; a polyvalent alcohol such as glycerine, propylene glycol or polyethylene glycol; an oily ingredient such as higher fatty acids, higher alcohols, hydrocarbons, natural oils and fats, ester oils or silicone oils; surfactants; perfumes; chelating agents; humectants such as 1,3-butyleneglycol, hyaluronic acid and its derivatives, maltitol, soluble collagen or sodium lactate; thickening agents such as quince mucilage, carboxyvinylpolymer or xanthan gum; antioxidants; ultraviolet absorbers: coloring agents; water; stabilizers; and the like, which are generally compounded in hair growth composition, can be compounded within the range provided that the effects of the present invention are not spoiled.

EXAMPLES

In the following, the present invention will be explained by using specific examples. However, the present invention should not be restricted thereto.

HAIR REGROWTH TEST (1) Test Method

By using C3H/HeNCrj mice, whose hair cycle was in resting stage, the experiment was performed according to the method of Ogawa et. al. (Normal and Abnormal Epidermal Differentiation, Edited by M. Seiji and I. A. Bernstein, Pages 159–170, 1982, Todai Shuppan). 10 mice were used in a group and the mice's hair within the area of 3×4 cm of the regions of back was shaved by a clipper and a shaver. 0.1 ml of ethanol (negative contrast) or ethanol solution of the tested compound was applied on the shaved portion once a day. For hair regrowth effect of the tested compound, the hair regrowth area of mice's region of back was measured and ratio of the hair regrowth area with respect to the shaved area was evaluated as hair regrowth area rate (%).

(2) Result

The average of hair regrowth area rate after each of the following tested compound was applied is shown in TABLE 1.

Compound 1

N,N-Dimethyl-3-(2-undecyl-1H-benzimidazol-1-yl)-1-propanamine

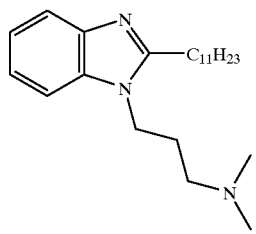

Compound 3

N,N-Dimethyl-3-(2-tridecyl-1H-benzimidazol-1-yl)-1-propanamine

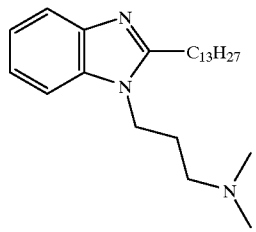

Compound 5

N,N-Dimethyl-3-(2-pentadecyl-1H-benzimidazol-1-yl)-1-propanamine

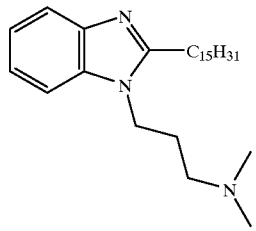

Compound 6

N,N-Dimethyl-3-(2-pentadecyl-1H-benzimidazol-1-yl)-1-propanamine monohydrochloride

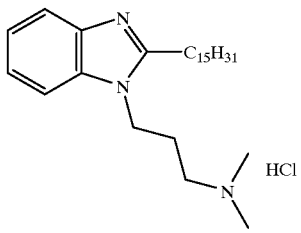

Compound 7

3-(2-Heptadecyl-1H-benzimidazol-1-yl)-N,N-dimethyl-1-propanamne

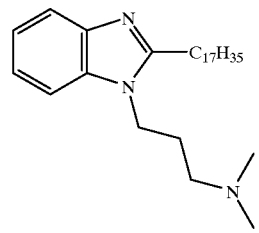

Compound 8

3-(2-Heptadecyl-1H-benzimidazol-1-yl)-N,N-dimethyl-1-propanamine monohydrochloride

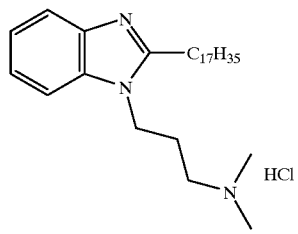

Compound 10

3-(2-Henicosyl-1H-benzimidazol-1-yl)-N,N-dimethyl-1-propanamine monohydrochloride

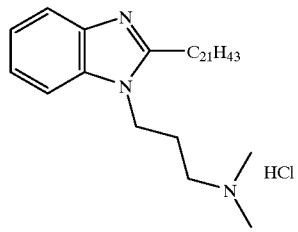

Compound 11

2-(2-Heptadecyl-1H-benzimidazol-1-yl)-N,N-dimethyl-1-ethanamine

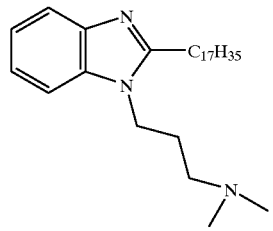

Compound 12

2-(2-Heptadecyl-1H-benzimidazol-1-yl)-N,N-dimethyl-1-ethanamine monohydrochloride

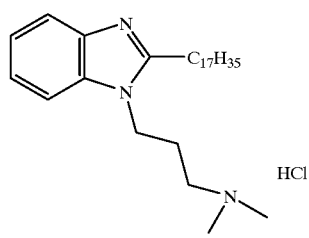

Compound 13

2-Heptadecyl-1-[3-(1H-imidazol-1-yl)propyl]-1H-benzimidazole

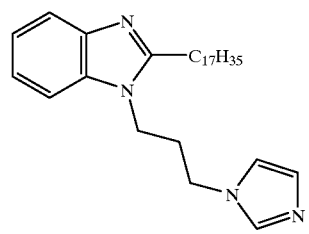

Compound 14

2-Heptadecyl-1-(3-morpholinopropyl)-1H-benzimidazole

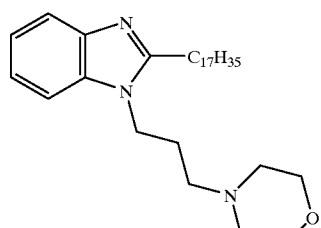

Compound 15

3-(5-Chloro-2-heptadecyl-1H-benzimidazol-1-yl)-N,N-dimethyl-1-propanamine

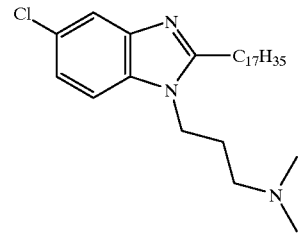

Compound 16

3-(5-Chloro-2-heptadecyl-1H-benzimidazol-1-yl)-N,N-dimethyl-1-propanamine monohydrochloride

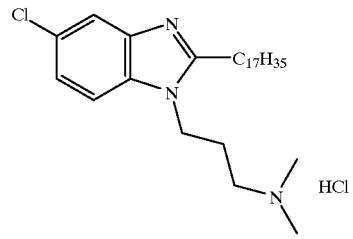

Compound 17

Ethyl 1-[3-(dimethylamino)propyl]-2-heptadecyl-1H-benzimidazole-5-carboxylate

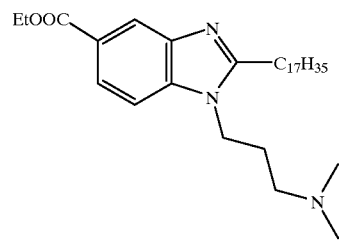

Compound 18

Ethyl 1-[3-(dimethylamino)propyl]-2-heptadecyl-1H-benzimidazole-5-carboxylate monohydrochloride

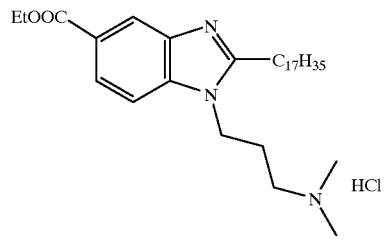

Compound 19

1-[3-(Dimethylamino)propyl]-2-heptadecyl-N-methyl-1H-benzimidazole-5-carboxamide

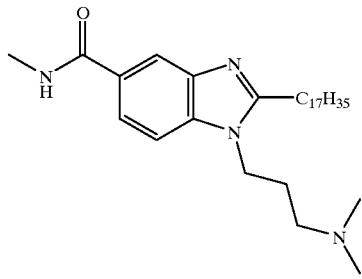

Compound 20

1-[3-(Dimethylamino)propyl]-2-heptadecyl-N-methyl-1H-benzimidazole-5-carboxamide monohydrochloride

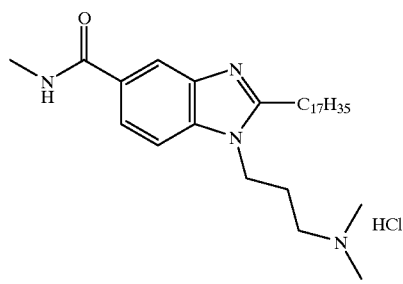

Compound 21

1-[3-(Dimethylamino)propyl]-2-heptadecyl-N,N-dimethyl-1H-benzimidazole-5-carboxamide

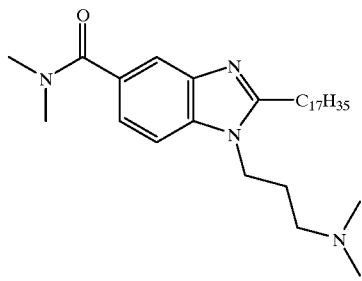

Compound 22

1-[3-(Dimethylamino)propyl]-2-heptadecyl-N,N-dimethyl-1H-benzimidazole-5-carboxamide monohydrochloxide

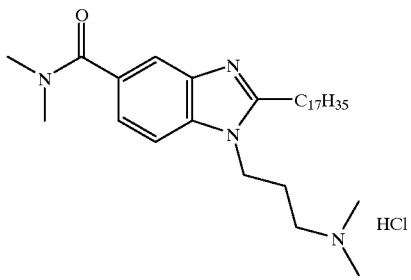

Compound 23

3-(2-Heptadecyl-5-methyl-1H-benzimidazol-1-yl)-N,N-dimethyl-1-propanamine

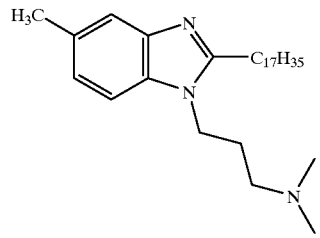

Compound 24

3-(2-Heptadecyl-5-methyl-1H-benzimidazol-1-yl)-N,N-dimethyl-1-propanamine monohydrochloride

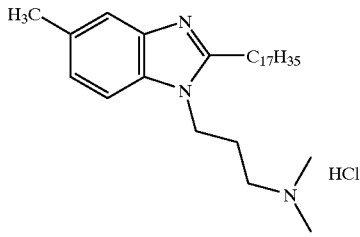

Compound 25

3-(7-Chloro-2-heptadecyl-1H-benzimidazol-1-yl)-N,
N-dimethyl-1-propanamine

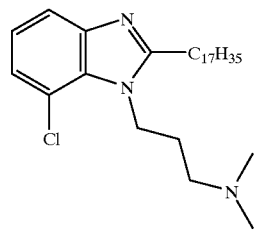

Compound 26

3-(7-Chloro-2-heptadecyl-1H-benzimidazol-1-yl)-N,
N-dimethyl-1-propanamine monohydrochloride

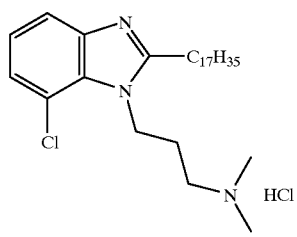

Compound 27

1-[3-(Dimethylamino)propyl]-2-heptadecyl-1H-
benzimidazol-5-amine

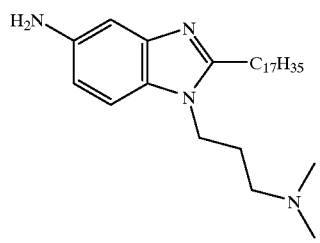

Compound 28

N-[3-(Dimethylamino)propyl]-1-octadecyl-1H-
benzimidazole-2-carboxamide

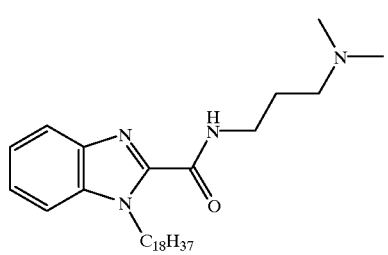

Compound 29

N-[3-(Dimethylamino)propyl]-1-octadecyl-1H-
benzimidazole-2-carboxamide monohydrochloride

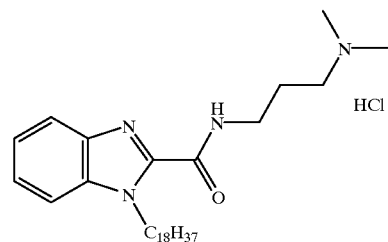

Compound 31

2-[(4-Methylpiperazinyl)carbonyl]-1-octadecyl-1H-
benzimidazole monohydrochloride

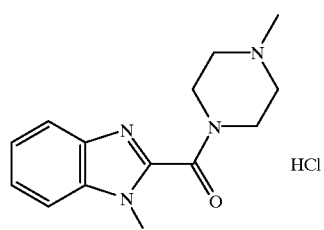

Compound 33

2-(2-Henicosyl-1H-benzimidazol-1-yl)-N,N-
dimethyl-1-ethanamine monohydrochloride

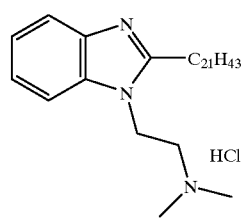

Compound 35

1-[3-(Dimethylamino)propyl]-2-henicosyl-N,N-dimethyl-1H-benzimidazole-5-carboxamide monohydrochloride

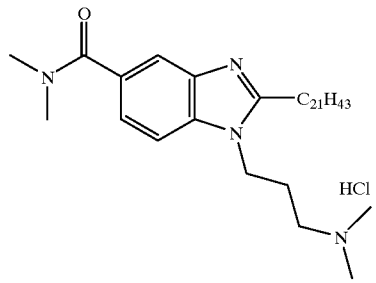

Compound 37

1-[3-(Dimethylamino)propyl]-2-henicosyl-N-methyl-1H-benzimidazole-5-carboxamide monohydrochloride

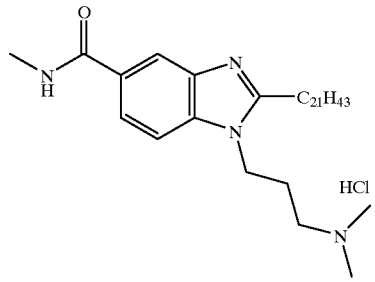

Compound 39

1-[2-(Dimethylamino)ethyl]-2-heptadecyl-N-methyl-1H-benzimidazole-5-carboxamide monohydrochloride

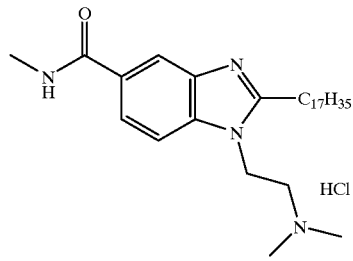

Compound 41

1-[2-(Dimethylamino)ethyl]-2-henicosyl-N-methyl-1H-benzimidazole-5-carboxamide monohydrochloride

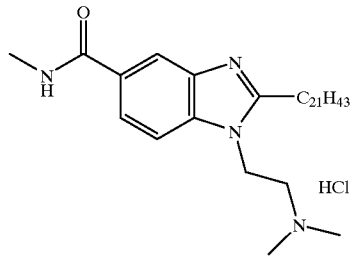

Compound 43

1-[2-(Dimethylamino)ethyl]-2-henicosyl-N,N-dimethyl-1H-benzimidazole-5-carboxamide monohydrochloride

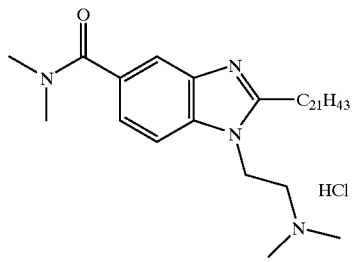

TABLE 1

| Compound | Conc. of Compd. (w/v%) | Days of Application (days) | Hair Regrowth Area Rate (%) |
|---|---|---|---|
| Ethanol (negative contrast) | — | 30 | 0 |
| Compound 1 | 0.2 | 23 | 24 |
| Compound 3 | 0.1 | 23 | 72 |
| Compound 5 | 0.1 | 23 | 100 |
| Compound 6 | 0.1 | 18 | 100 |
| Compound 7 | 0.1 | 24 | 100 |
| Compound 8 | 0.1 | 24 | 100 |
| Compound 10 | 0.2 | 24 | 82 |
| Compound 11 | 0.1 | 23 | 100 |
| Compound 12 | 0.1 | 23 | 100 |
| Compound 13 | 0.1 | 23 | 78 |
| Compound 14 | 0.2 | 23 | 50 |
| Compound 15 | 0.1 | 24 | 100 |
| Compound 16 | 0.1 | 24 | 100 |
| Compound 17 | 0.1 | 24 | 100 |
| Compound 18 | 0.1 | 23 | 100 |
| Compound 19 | 0.1 | 24 | 100 |
| Compound 20 | 0.1 | 24 | 100 |
| Compound 21 | 0.1 | 18 | 100 |
| Compound 22 | 0.1 | 23 | 100 |
| Compound 23 | 0.1 | 24 | 100 |
| Compound 24 | 0.1 | 23 | 97 |
| Compound 25 | 0.1 | 24 | 100 |
| Compound 26 | 0.1 | 24 | 100 |
| Compound 27 | 0.1 | 24 | 100 |
| Compound 28 | 0.1 | 18 | 100 |
| Compound 29 | 0.1 | 18 | 100 |
| Compound 31 | 0.2 | 24 | 100 |
| Compound 33 | 0.2 | 30 | 60 |

TABLE 1-continued

| Compound | Conc. of Compd. (w/v%) | Days of Application (days) | Hair Regrowth Area Rate (%) |
|---|---|---|---|
| Compound 35 | 0.2 | 23 | 95 |
| Compound 37 | 0.2 | 30 | 80 |
| Compound 39 | 2.0 | 30 | 39 |
| Compound 41 | 2.0 | 30 | 38 |
| Compound 43 | 0.2 | 23 | 88 |

As is clear from the TABLE 1, benzimidazole derivatives and their pharmacologically acceptable salts in accordance with the present invention show excellent hair regrowth and growth promoting effects.

In the following, examples of compounds and compositions in accordance with the present invention will be explained. However, the present invention should not be restricted thereto.

Example 1

N,N-Dimethyl-3-(2-undecyl-1H-benzimidazol-1-yl)-1-propanamine (Compound 1)

(1) $N^1,N^1$-Dimethyl-$N^3$-(2-nitrophenyl)-1,3-propanediamine

N,N-Dimethyl-1,3-propanediamine (3.24 g) was added to a solution containing 2-chloronitrobenzene (2.00 g) in pyridine (2.56 ml). After being stirred for 13 hours at 120–130° C., the reaction mixture was concentrated. The residue, with toluene added thereto, was washed with saturated sodium hydrogencarbonate aqueous solution and saturated brine successively, dried over sodium sulfate anhydride, and concentrated, thereby yielding the entitled compound (2.83 g) as orange oil.

$^1$H-NMR (CDCl$_3$) δ: 1.87 (2H, quintet, J=6.8 Hz), 2.26 (6H, s), 2.43 (2H, t, J=6.8 Hz), 3.38 (2H, td, J=6.8, 5.4 Hz), 6.61 (1H, ddd, J=8.3, 6.8, 1.5 Hz), 6.87 (1H, d, J=8.3 Hz), 7.41 (1H, m), 8.16 (1H, dd, J=8.3, 1.5 Hz), 8.41 (1H, brs).

(2) N-[3-(Dimethylamino)propyl]-1,2-benzenediamine

10% of palladium-carbon (0.18 g) was added to a solution containing $N^1,N^1$-dimethyl-$N^3$-(2-nitrophenyl)-1,3-propanediamine (0.90 g) in ethanol (9 ml) and stirred for 2.5 hours under a hydrogen gas atmosphere at room temperature. After the catalyst was removed out by filtration, the filtrate was concentrated, thereby yielding the entitled compound (0.78 g) as reddish brown oil.

$^1$H-NMR (CDCl$_3$) δ: 1.84 (2H, quintet, J=6.8 Hz), 2.26 (6H, s), 2.43 (2H, t, J=6.8 Hz), 3.18 (2H, t, J=6.8 Hz), 3.33 (2H, brs), 3.5–4.3 (1H, brs), 6.65 (2H, m), 6.70 (1H, m), 6.80 (1H, m).

(3) N,N-Dimethyl-3-(2-undecyl-1H-benzimidazol-1-yl)-1-propanamine

Triethylamine (0.85 ml) was added to a solution containing N-[3-(dimethylamino)propyl]-1,2-benzenediamine (1.06 g) in chloroform (11 ml) and then dodecanoyl chloride (1.28 ml) was added thereto while being cooled with ice. After being stirred for 3 hours at room temperature, the reaction mixture was diluted with chloroform, washed with saturated sodium hydrogencarbonate aqueous solution and water successively, dried over sodium sulfate anhydride, and concentrated. Concentrated hydrochloric acid (4.6 ml) was added to a solution containing the residue (2.23 g) in ethanol (23 ml). After being stirred for 1.5 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (2.14 g) was purified by silica gel column chromatography (silica gel 50 g, chloroform:methanol=60:1), thereby yielding the entitled compound (1.33 g) as pale brown wax.

$^1$H-NMR (CDCl$_3$) δ: 0.88 (3H, t, J=6.8 Hz), 1.2–1.4 (14H, m), 1.45 (2H, m), 1.85–1.98 (4H, m), 2.23 (6H, s), 2.27 (2H, t, J=6.8 Hz), 2.88 (2H, t, J=7.8 Hz), 4.19 (2H, t, J=7.1 Hz), 7.20–7.24 (2H, m), 7.34 (1H, m), 7.72 (1H, m).

Example 2

N,N-Dimethyl-3-(2-undecyl-1H-benzimidazol-1-yl)-1-propanamine monohydrochloride

Compound 2

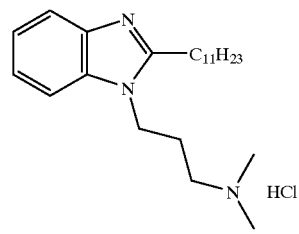

4N Hydrochloric acid/ethyl acetate solution (0.14 ml) was added to a solution containing N,N-dimethyl-3-(2-undecyl-1H-benzimidazol-1-yl)-1-propanamine (0.20 g) in ethyl acetate (2 ml). After being stirred for 20 minutes at room temperature, the reaction mixture was concentrated. The residue was recrystallized with the mixed solution of ethyl acetate-hexane, thereby yielding the entitled compound (0.21 g) as pale yellow solid.

$^1$H-NMR (CDCl$_3$) δ: 0.88 (3H, t, J=6.8 Hz), 1.2–1.4 (14H, m), 1.46 (2H, m), 1.91 (2H, quintet, J=7.8 Hz), 2.37 (2H, m), 2.65 (6H, s), 2.85 (2H, m), 2.88 (2H, t, J=7.8 Hz), 4.35 (2H, t, J=6.8 Hz), 7.23–7.28 (2H, m), 7.38 (1H, m), 7.74 (1H, m).

Example 3

N,N-Dimethyl-3-(2-tridecyl-1H-benzimidazol-1-yl)-1-propanamine (Compound 3)

Triethylamine (0.80 ml) was added to a solution containing N-[3-(dimethylamino)propyl]-1,2-benzenediamine (1.00 g) in chloroform (10 ml), and then tetradecanoyl chloride (1.42 ml) was added thereto while being cooled with ice. After being stirred for 3 hours at room temperature, the reaction mixture was diluted with chloroform, washed with saturated sodium hydrogencarbonate aqueous solution and water successively, dried over sodium sulfate anhydride, and concentrated. Concentrated hydrochloric acid (4.3 ml) was added to a solution containing the residue (2.29 g) in ethanol (23 ml). After being stirred for 1.5 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (2.18 g) was purified by silica gel column chromatography (silica gel 50 g, chloroform:methanol=50:1), thereby yielding the entitled compound (1.38 g) as pale brown wax.

$^1$H-NMR (CDCl$_3$) δ: 0.88 (3H, t, J=6.8 Hz), 1.2–1.4 (18H, m), 1.45 (2H, m), 1.87–1.96 (4H, m), 2.23 (6H, s), 2.27 (2H, t, J=6.6 Hz), 2.88 (2H, t, J=8.1 Hz), 4.19 (2H, t, J=7.3 Hz), 7.20–7.23 (2H, m), 7.34 (1H, m), 7.72 (1H, m).

Example 4

N,N-Dimethyl-3-(2-tridecyl-1H-benzimidazol-1-yl)-1-propanamine monohydrochloride Compound 4

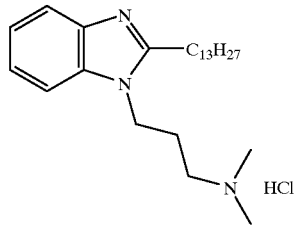

4N Hydrochloric acid/ethyl acetate solution (0.14 ml) was added to a solution containing N,N-dimethyl-3-(2-tridecyl-1H-benzimidazol-1-yl)-1-propanamine (0.20 g) in ethyl acetate (2 ml). After being stirred for 20 minutes at room temperature, the reaction mixture was concentrated. The residue was recrystallized with the mixed solution of ethyl acetate-hexane, thereby yielding the entitled compound (0.15 g) as white solid.

$^1$H-NMR (CDCl$_3$) δ: 0.88 (3H, t, J=6.8 Hz), 1.2–1.4 (18H, m), 1.45 (2H, m), 1.9 (2H, quintet, J=7.8 Hz), 2.45 (2H, m), 2.74 (6H, s), 2.95 (2H, t, J=7.8 Hz), 3.01 (2H, m), 4.42 (2H, t, J=6.8 Hz), 7.28–7.32 (2H, m), 7.47 (1H, m), 7.76 (1H, m).

Example 5

N,N-Dimethyl-3-(2-pentadecyl-1H-benzimidazol-1-yl)-1-propanamine (Compound 5)

Triethylamine (0.80 ml) was added to a solution containing N-[3-(dimethylamino)propyl]-1,2-benzenediamine (1.00 g) in chloroform (10 ml) and then palmitoyl chloride (1.58 ml) was added thereto while being cooled with ice. After being stirred for 2.5 hours at room temperature, the reaction mixture was diluted with chloroform, washed with saturated sodium bydrogencarbonate aqueous solution and water successively, dried over sodium sulfate anhydride, and concentrated. Concentrated hydrochloric acid (4.3 ml) was added to a solution containing the residue (2.25 g) in ethanol (23 ml). After being stirred for 1.5 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (2.21 g) was purified by silica gel column chromatography (silica gel 50 g, chloroform:methanol=30:1), thereby yielding the entitled compound (1.44 g) as yellow syrup.

$^1$H-NMR (CDCl$_3$) δ: 0.88 (3H, t, J=6.8 Hz), 1.2–1.4 (22H, m), 1.45 (2H, m), 1.86–1.98 (4H, m), 2.23 (6H, s), 2.27 (2H, t, J=6.6 Hz), 2.88 (2H, t, J=7.8 Hz), 4.19 (2H, t, J=7.1 Hz), 7.20–7.23 (2H, m), 7.34 (1H, m), 7.72 (1H, m).

Example 6

N,N-Dimethyl-3-(2-pentadecyl-1H-benzimidazol-1-yl)-1-propanamine monohydrochloride (Compound 6)

4N Hydrochloric acid/ethyl acetate solution (0.13 ml) was added to a solution containing N,N-dimethyl-3-(2-pentadecyl-1H-benzimidazol-1-yl)-1-propanamine (0.20 g) in ethyl acetate (2 ml). After being stirred for 20 minutes at room temperature, the reaction mixture was concentrated. The residue was recrystallized with the mixed solution of ethyl acetate-hexane, thereby yielding the entitled compound (0.13 g) as white solid.

$^1$H-NMR (CDCl$_3$) δ: 0.88 (3H, t, J=6.8 Hz), 1.2–1.4 (22H, m), 1.45 (2H, m), 1.91 (2H, quintet, J=7.8 Hz), 2.44 (2H, m), 2.73 (6H, s), 2.92 (2H, t, J=7.8 Hz), 2.98 (2H, m), 4.40 (2H, t, J=6.8 Hz), 7.26–7.31 (2H, m), 7.44 (1H, m), 7.76 (1H, m).

Example 7

3-(2-Heptadecyl-1H-benzimidazol-1-yl)-N,N-dimethyl-1-propanamine (Compound 7)

Triethylamine (0.62 ml) was added to a solution containing N-[3-(dimethylamino)propyl]-1,2-benzenediamine (0.78 g) in chloroform (4 ml) and then stearoyl chloride (1.22 g) was added thereto while being cooled with ice. After being stirred for 2 hours at room temperature, the reaction mixture was diluted with chloroform, washed with saturated sodium hydrogencarbonate aqueous solution and water successively, dried over sodium sulfate anhydride, and concentrated. Concentrated hydrochloric acid (3.33 ml) was added to a solution containing the residue (1.93 g) in n ethanol (20 ml). After being stirred for 5 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (1.73 g) was purified by silica gel column chromatography (silica gel 50 g, chloroform:methanol=50:1), thereby yielding the entitled compound (1.53 g) as pale brown wax.

$^1$H-NMR (CDCl$_3$) δ: 0.88 (3H, t, J=6.8 Hz), 1.2–1.4 (26H, m), 1.45 (2H, m), 1.85–1.98 (4H, m), 2.23 (6H, s), 2.27 (2H, t, J=6.8 Hz), 2.88 (2H, t, J=8.1 Hz), 4.19 (2H, t, J=7.1 Hz), 7.21 (2H, m), 7.34 (1H, m), 7.72 (1H, m).

Example 8

3-(2-Heptadecyl-1H-benzimidazol-1-yl)-N,N-dimethyl-1-propanamine monohydrochloride (Compound 8)

4N Hydrochloric acid/ethyl acetate solution (0.19 ml) was added to a solution containing 3-(2-heptadecyl-1H-benzimidazol-1-yl)-N,N-dimethyl-1-propanamine (0.33 g) in ethyl acetate (5 ml). After being stirred for 10 minutes at room temperature, the reaction mixture was concentrated. The residue was recrystallized with ethyl acetate, thereby yielding the entitled compound (0.32 g) as white solid.

$^1$H-NMR (CDCl$_3$) δ: 0.88 (3H, t, J=6.8 Hz), 1.2–1.4 (26H, m), 1.45 (2H, m), 1.91(2H, quintet, J=7.8 Hz), 2.45 (2H, m), 2.73 (6H, s), 2.93 (4H, m), 4.41 (2H, t, J=6.8 Hz), 7.29 (2H, m), 7.43 (1H, m), 7.76 (1H, m).

Example 9

3-(2-Henicosyl-1H-benzimidazol-1-yl)-N,N-dimethyl-1-propanamine

Compound 9

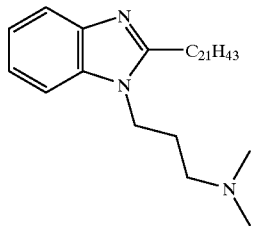

Triethylamine (0.73 ml) was added to a suspension containing n-docosanoic acid (1.59 g) in chloroform (16 ml), and then ethyl chlorocarbonate (0.50 ml) was added thereto while being cooled with ice. The mixture was stirred for 2 hours, and then a solution containing N-[3-(dimethylamino)propyl]-1,2-benzenediamine (0.91 g) in chloroform (5 ml) added thereto. After being stirred for 2.5 hours at room temperature, the reaction mixture was diluted with chloroform, washed with saturated sodium hydrogencarbonate aqueous solution and saturated brine successively, dried over sodium sulfate anhydride, and concentrated. Concentrated hydrochloric acid (3.9 ml) was added to a solution containing the residue (2.43 g) in ethanol (25 ml). After being stirred for 1.5 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (2.65 g) was purified by silica gel column chromatography (silica gel 63 g, chloroform:methanol=60:1), thereby yielding the entitled compound (0.88 g) as pale brown solid.

$^1$H-NMR (CDCl$_3$) δ: 0.88 (3H, t, J=6.8 Hz), 1.2–1.4 (34H, m), 1.45 (2H, m), 1.85–1.98 (4H, m), 2.23 (6H, s), 2.27 (2H, t, J=6.8 Hz), 2.88 (2H, t, J=8.1 Hz), 4.19 (2H, t, J=7.3 Hz), 7.19–7.24 (2H, m), 7.34 (1H, m), 7.72 (1H, m).

Example 10

3-(2-Henicosyl-1H-benzimidazol-1-yl)-N,N-dimethyl-1-propanamine monohydrochloride (Compound 10)

4N Hydrochloric acid/ethyl acetate solution (0.11 ml) was added to a solution containing 3-(2-henicosyl-1H-benzimidazol-1-yl)-N,N-dimethyl-1-propanamine (0.20 g) in ethyl acetate (2 ml). After being stirred for 20 minutes at room temperature, the reaction mixture was concentrated. The residue was recrystallized with the mixed solution of ethanol-ethyl acetate, thereby yielding the entitled compound (0.19 g) as white solid.

$^1$H-NMR (CDCl$_3$) δ: 0.88 (3H, t, J=6.8 Hz), 1.2–1.4 (34H, m), 1.45 (2H, m), 1.91 (2H, quintet, J=7.8 Hz), 2.44 (2H, m), 2.71 (6H, s), 2.91 (2H, m), 2.94 (2H, m), 4.39 (2H, t, J=6.8 Hz), 7.25–7.30 (2H, m), 7.41 (1H, m), 7.75 (1H, m).

Example 11

2-(2-Heptadecyl-1H-benzimidazol-1-yl)-N,N-dimethyl-1-ethanamine (Compound 11)
(1) N$^1$,N$^1$-Dimethyl-N$^3$-(2-nitrophenyl)-1,2-ethanediamine N,N-Dimethylethylenediamine (3.65 ml) was added to 2-chloronitrobenzene (2.614 g) and stirred for 14.5 hours at 100° C. The reaction mixture, with ethyl acetate added thereto, was washed with 1N sodium hydroxide aqueous solution, and extracted with 1N hydrochloric acid aqueous solution. The extract was alkalified with 1N sodium hydroxide aqueous solution and extracted with ethyl acetate. The extract was washed with saturated brine, dried over sodium sulfate anhydride, and concentrated, thereby yielding the entitled compound (3.170 g) as orange oil.

$^1$H-NMR (CDCl$_3$) δ: 2.31 (6H, s), 2.63 (2H, t, J=6.4 Hz), 3.35 (2H, td, J=6.4, 4.9 Hz), 6.63 (1H, ddd, J=8.3, 6.8, 1.5 Hz), 6.83 (1H, dd, J=7.8, 1.5 Hz), 7.43 (1H, ddd, J=7.8, 6.8, 1.5 Hz), 8.17 (1H, dd, J=8.3, 1.5 Hz), 8.31 (1H, brs).

(2) N-[2-(Dimethylamino)ethyl]-1,2-benzenediamine

10% of palladium-carbon (0.600 g) was added to a solution containing N$^1$,N$^1$-dimethyl-N$^3$-(2-nitrophenyl)-1,2-ethanediamine (2.986 g) in ethanol (30 ml) and stirred for 5 hours under a hydrogen gas atmosphere at room temperature. After the catalyst was removed out by filtration, the filtrate was concentrated, thereby yielding the entitled compound (2.526 g) as reddish brown solid.

$^1$H-NMR (CDCl$_3$) δ: 2.38 (6H, s), 2.75 (2H, t, J=5.9 Hz), 3.23 (2H, t, J=5.9 Hz), 3.82 (3H, brs), 6.63 (1H, dd, J=7.3, 1.5 Hz), 6.65–6.72 (2H, m), 6.78 (1H, m).

(3) 2-(2-Heptadecyl-1H-benzimidazol-1-yl)-N,N-dimethyl-1-ethanamine

Triethylamine (0.73 ml) was added to a solution containing N-[2-(dimethylamino)ethyl]-1,2-benzenediamine (0.851 g) in chloroform (4.5 ml), and then a solution containing stearoyl chloride (1.439 g) in chloroform (5.5 ml) was added thereto while being cooled with ice. After being stirred for 2 hours at room temperature, the reaction mixture was diluted with chloroform, washed with saturated sodium hydrogencarbonate aqueous solution and water successively, dried over sodium sulfate anhydride, and concentrated. Concentrated hydrochloric acid (3.95 ml) was added to a solution containing the residue (2.109 g) in ethanol (22 ml). After being stirred for 1.5 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (2.000 g) was purified by silica gel column chromatography (silica gel 50 g, chloroform:methanol=60:1), thereby yielding the entitled compound (1.366 g) as white solid.

$^1$H-NMR (CDCl$_3$) δ: 0.88 (3H, t, J=6.8 Hz), 1.2–1.4 (26H, m), 1.45 (2H, m), 1.90 (2H, quintet, J=7.8 Hz), 2.33 (6H, s), 2.63 (2H, t, J=7.6 Hz), 2.87 (2H, t, J=7.8 Hz), 4.20 (2H, t, J=7.6 Hz), 7.20–7.25 (2H, m), 7.31 (1H, m), 7.72 (1H, m).

Example 12

2-(2-Heptadecyl-1H-benzimidazol-1-yl)-N,N-dimethyl-1-ethanamine monohydrochloride (Compound 12)

4N Hydrochloric acid/ethyl acetate solution (0.12 ml) was added to a solution containing 2-(2-heptadecyl-1H-benzimidazol-1-yl)-N,N-dimethyl-1-ethanamine (0.200 g) in ethyl acetate (2 ml). After being stirred for 15 minutes at room temperature, the reaction mixture was concentrated. The residue was recrystallized with the mixed solution of ethanol-ethyl acetate, thereby yielding the entitled compound (0.182 g) as white solid.

$^1$H-NMR (CDCl$_3$) δ: 0.88 (3H, t, J=6.8 Hz), 1.2–1.4 (26H, m), 1.45 (2H, m), 1.92 (2H, quintet, J=7.8 Hz), 2.73 (6H, s), 3.06 (2H, t, J=7.8 Hz), 3.20 (2H, brt), 4.71 (2H, brt), 7.30–7.37 (2H, m), 7.58 (1H, m), 7.79 (1H, m).

Example 13

2-Heptadecyl-1-[3-(1H-imidazol-1-yl)propyl]-1H-benzimidazole (Compound 13)

(1) N-[3-(1H-imidazol-1-yl)propyl]-2-nitroaniline 1-(3-Aminopropyl)imidazole (4.55 ml) was added to 2-chloronitrobenzene (3.000 g) and stirred for 15 hours at 125° C. The reaction mixture, with ethyl acetate added thereto, was washed with 1N sodium hydroxide aqueous solution, and extracted with 1N hydrochloric acid aqueous solution. The extract was alkalified with 1N sodium hydroxide aqueous solution, and extracted with ethyl acetate. The extract was washed with saturated brine, dried over sodium sulfate anhydride, and concentrated, thereby yielding the entitled compound (4.442 g) as orange oil.

$^1$H-NMR (CDCl$_3$) δ: 2.22 (2H, quintet, J=6.8 Hz), 3.30 (2H, td, J=6.8, 5.4 Hz), 4.13 (2H, t, J=6.8 Hz), 6.70 (1H, ddd, J=8.8, 7.3, 1.5 Hz), 6.75 (1H, d, J=8.3 Hz), 6.94 (1H, t, J=1.5 Hz), 7.10 (1H, d, J=1.0 Hz), 7.44 (1H, ddd, J=8.3, 7.3, 1.5 Hz), 7.49 (1H, s), 8.01 (1H, brs), 8.19 (1H, dd, J=8.8, 1.5 Hz).

(2) N-[3-(1H-Imidazol-1-yl)propyl]-1,2-benzenediamine

10% of palladium-carbon (0.804 g) was added to a solution containing N-[3-(1H-imidazol-1-yl)propyl]-2-nitroaniline (4.000 g) in ethanol (40 ml) and stirred for 4.5 hours under a hydrogen gas atmosphere at room temperature. After the catalyst was removed out by filtration, the filtrate was concentrated, thereby yielding the entitled compound (3.503 g) as black solid.

$^1$H-NMR (CDCl$_3$) δ: 2.13 (2H, quintet, J=6.8 Hz), 3.09 (3H, brs), 3.14 (2H, t, J=6.8 Hz), 4.12 (2H, t, J=6.8 Hz), 6.60 (1H, dd, J=7.8, 1.5 Hz), 6.67–6.74 (2H, m), 6.81 (1H, m), 6.94(1H, t, J=1.5 Hz), 7.08 (1H, t, J=1.5 Hz), 7.54 (1H, s).

(3) 2-Heptadecyl-1-[3-(1H-imidazol-1-yl)propyl]-1H-benzimidazole

Triethylamine (0.72 ml) was added to a solution containing N-[3-(1H-imidazol-1-yl)propyl]-1,2-benzenediamine (1.000 g) in chloroform (10.0 ml), and then stearoyl chloride (1.58 ml) was added thereto while being cooled with ice. After being stirred for 4.5 hours at room temperature, the reaction mixture was diluted with chloroform, washed with saturated sodium hydrogencarbonate aqueous solution and water successively, dried over sodium sulfate anhydride, and concentrated. Concentrated hydrochloric acid (3.85 ml) was added to a solution containing the residue (2.149 g) in ethanol (22 ml). After being stirred for 1.5 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (2.273 g) was purified by silica gel column chromatography (silica gel 50 g, chloroform:methanol=60:1), thereby yielding the entitled compound (1.657 g) as yellow solid.

$^1$H-NMR (CDCl$_3$) δ: 0.88 (3H, t, J=6.8 Hz), 1.2–1.4 (26H, m), 1.42 (2H, m), 1.86 (2H, quintet, J=7.8 Hz), 2.32 (2H, m), 2.74 (2H, t, J=7.8 Hz), 4.02 (2H, t, J=6.8 Hz), 4.10 (2H, t, J=7.3 Hz), 6.94 (1H, s), 7.14 (1H, m), 7.15 (1H, s), 7.21–7.27 (2H, m), 7.50 (1H, s), 7.73 (1H, m).

Example 14

2-Heptadecyl-1-(3-morpholinopropyl)-1H-benzimidazole (Compound 14)

(1) N-(3-Morpholinopropyl)-2-nitroaniline

N-(3-Aminopropyl)morpholine (1.04 ml) was added to a solution containing 2-chloronitrobenzene (1.005 g) in pyridine (0.78 ml), and stirred for 14 hours at 130° C. Toluene was added to the reaction mixture and concentrated. The residue, with ethyl acetate added thereto, was extracted with 1N hydrochloric acid aqueous solution. The extract was alkalified with 1N sodium hydroxide aqueous solution and extracted with ethyl acetate. The extract was washed with saturated brine, dried over sodium sulfate anhydride, and concentrated, thereby yielding the entitled compound (1.217 g) as orange oil.

$^1$H-NMR (CDCl$_3$) δ: 1.90 (2H, quintet, J=6.8 Hz), 2.48 (6H, m), 3.40 (2H, td, J=6.8, 5.4 Hz), 3.76 (4H, t, J=4.6 Hz), 6.63 (1H, ddd, J=8.8, 7.3, 1.5 Hz), 6.88 (1H, d, J=7.8 Hz), 7.43 (1H, m), 8.17 (1H, dd, J=8.8, 1.5 Hz), 8.29 (1H, brs).

(2) N-(3-Morpholinopropyl)-1,2-benzenediamine

10% of palladium-carbon (0.237 g) was added to a solution containing N-(3-morpholinopropyl)-2-nitroaniline (1.040 g) in ethanol (12 ml) and the mixture was stirred for 7 hours under a hydrogen gas atmosphere at room temperature. After the catalyst was removed out by filtration, the filtrate was concentrated, thereby yielding the entitled compound (0.667 g) as blackish brown solid.

$^1$H-NMR (CDCl$_3$) δ: 1.91 (2H, quintet, J=6.4 Hz), 2.50–2.62 (6H, m), 3.22 (2H, t, J=6.4 Hz), 3.79 (4H, t, J=4.6 Hz), 6.62–6.72 (3H, m), 6.80 (1H, m).

(3) 2-Heptadecyl-1-(3-morpholinopropyl)-1H-benzimidazole

Triethylamine (0.42 ml) was added to a solution containing N-(3-morpholinopropyl)-1,2-benzenediamine (0.640 g) in chloroform (3.5 ml), and then a solution containing stearoyl chloride (0.825 g) in chloroform (3.5 ml) was added thereto while being cooled with ice. After being stirred for 3 hours at room temperature, the reaction mixture was diluted with chloroform, washed with saturated sodium hydrogencarbonate aqueous solution and water successively, dried over sodium sulfate anhydride, and concentrated. Concentrated hydrochloric acid (2.25 ml) was added to a solution containing the residue (1.442 g) in ethanol (15 ml). After being stirred for 1.5 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (1.296 g) was purified by silica gel column chromatography (silica gel 40 g, ethyl acetate), thereby yielding the entitled compound (1.088 g) as yellow solid.

$^1$H-NMR (CDCl$_3$) δ: 0.88 (3H, t, J=6.8 Hz), 1.2–1.4 (26H, m), 1.45 (2H, m), 1.89 (2H, quintet, J=7.8 Hz), 1.97 (2H, quintet, J=6.8 Hz), 2.31 (2H, t, J=6.8 Hz), 2.40 (4H, m), 2.89 (2H, t, J=7.8 Hz), 3.72 (4H, t, J=4.6 Hz), 4.21 (2H, t, J=6.8 Hz), 7.18–7.24 (2H, m), 7.34 (1H, m), 7.72 (1H, m).

Example 15

3-(5-Chloro-2-heptadecyl-1H-benzimidazol-1-yl)-N,N-dimethyl-1-propanamine (Compound 15)

(1) $N^1$-(4-Chloro-2-nitrophenyl)-$N^3$,$N^3$-dimethyl-1,3-propanediamine

N,N-Dimethyl-1,3-propanediamine (2.92 ml) was added to 2,5-dichloronitrobenzene (2.23 g) and stirred for 14 hours at 125° C. The reaction mixture, with ethyl acetate added thereto, was washed with 1N sodium hydroxide aqueous solution, water and saturated brine successively, dried over sodium sulfate anhydride, and concentrated, thereby yielding the entitled compound (2.99 g) as brown oil.

$^1$H-NMR (CDCl$_3$) δ: 1.86 (2H, quintet, J=6.8 Hz), 2.26 (6H, s), 2.43 (2H, t, J=6.8 Hz), 3.37 (2H, td, J=6.8, 4.9 Hz), 6.83 (1H, d, J=9.3 Hz), 7.35 (1H, dd, J=9.3, 2.4 Hz), 8.14 (1H, d, J=2.4 Hz), 8.53 (1H, brs).

(2) 4-Chloro-N$^1$-[3-(dimethylamino)propyl]-1,2-benzenediamine

A solution containing tin(II) chloride dihydrate (7.85 g) in concentrated hydrochloric acid (10 ml) was added to a solution containing N$^1$-(4 chloro-2-nitrophenyl)-N$^3$,N$^3$-dimethyl-1,3-propanediamine (2.99 g) in concentrated hydrochloric acid (10 ml) while being cooled with ice. After being stirred for 15 hours at room temperature, the reaction mixture was neutralized with 10N sodium hydroxide aqueous solution while being cooled with ice and extracted with ethyl acetate. The extract was washed with water and saturated brine successively, dried over sodium sulfate anhydride, and concentrated, thereby yielding the entitled compound (2.60 g) as brown solid.

$^1$H-NMR (CDCl$_3$) δ: 1.81 (2H, m), 2.25 (6H, s), 2.41 (2H, t, J=6.8 Hz), 3.13 (2H, t, J=6.4 Hz), 3.40 (2H, brs), 3.5–4.3 (1H, brs), 6.51(1H, d, J=8.3 Hz), 6.65 (1H, d, J=2.5 Hz), 6.73 (1H, dd, J=8.3, 2.5 Hz).

(3) 3-(5-Chloro-2-heptadecyl-1H-benzimidazol-1-yl)-N,N-dimethyl-1-propanamine

Triethylamine (1.75 ml) was added to a solution containing 4-chloro-N$^1$-[3-(dimethylamino)propyl]-1,2-benzenediamine (2.60 g) in chloroform (25 ml), and then a solution containing stearoyl chloride (3.46 g) in chloroform (5 ml) was added thereto while being cooled with ice. After being stirred for 3 hours at room temperature, the reaction mixture was diluted with chloroform, washed with saturated sodium hydrogencarbonate aqueous solution and water successively, dried over sodium sulfate anhydride, and concentrated. Concentrated hydrochloric acid (9.00 ml) was added to a solution containing the residue (5.94 g) in ethanol (50 ml). After being stirred for 2 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (5.61 g) was purified by silica gel column chromatography (silica gel 50 g, chloroform:methanol=50:1–20:1), thereby yielding the entitled compound (4.90 g) as pale yellow solid.

$^1$H-NMR (CDCl$_3$) δ: 0.88 (3H, t, J=6.8 Hz), 1.2–1.4 (26H, m), 1.44 (2H, m), 1.83–1.95 (4H, m), 2.21 (6H, s), 2.24 (2H, t, J=6.6 Hz), 2.86 (2H, t, J=8.1 Hz), 4.16 (2H, t, J=7.1 Hz), 7.18 (1H, dd, J=8.3, 2.0 Hz), 7.26 (1H, d, J=8.3 Hz), 7.68 (1H, d, J=2.0 Hz).

Example 16

3-(5-Chloro-2-heptadecyl-1H-benzimidazol-1-yl)-N,N-dimethyl-1-propanamine monohydrochloride (Compound 16)

4N Hydrochloric acid/ethyl acetate solution (0.24 ml) was added to a solution containing 3-(5-Chloro-2-heptadecyl-1H-benzimidazol-1-yl)-N,N-dimethyl-1-propanamine (0.46 g) in ethyl acetate (5 ml). After being stirred for 10 minutes at room temperature, the reaction mixture was concentrated. The residue was recrystallized with the mixed solution of ethanol-ethyl acetate, thereby yielding the entitled compound (0.42 g) as white solid.

$^1$H-NMR (CDCl$_3$) δ: 0.88 (3H, t, J=6.8 Hz), 1.2–1.4 (26H, m), 1.44 (2H, m), 1.89 (2H, m), 2.42 (2H, m), 2.75 (6H, s), 2.86 (2H, t, J=7.3 Hz), 2.96 (2H, t, J=7.3 Hz), 4.37 (2H, t, J=6.8 Hz), 7.24 (1H, dd, J=8.8, 2.0 Hz), 7.36 (1H, d, J=8.8 Hz), 7.71 (1H, d, J=2.0 Hz).

Example 17

Ethyl 1-[3-(dimethylamino)propyl]-2-heptadecyl-1H-benzimidazole-5-carboxylate (Compound 17)

(1) Ethyl 4-chloro-3-nitrobenzoate

Concentrated sulfulic acid (5 ml) was added to a solution containing 4-chloro-3-nitrobenzoic acid (5.04 g) in ethanol (50 ml). After being stirred for 3 hours at 90° C., the reaction mixture was concentrated. The residue was diluted with ethyl acetate, and neutralized and washed with saturated hydrogencarbonate aqueous solution. The organic layer was washed with water and saturated brine successively, dried over sodium sulfate anhydride, and concentrated, thereby yielding the entitled compound (5.55 g) as pale yellow solid.

$^1$H-NMR (CDCl$_3$) δ: 1.43 (3H, t, J=7.3 Hz), 4.43 (2H, q, J=7.3 Hz), 7.65 (1H, d, J=8.3 Hz), 8.17 (1H, dd, J=8.3, 2.0 Hz), 8.50 (1H, d, J=2.0 Hz).

(2) Ethyl 4-{[3-(dimethylamino)propyl]amino}-3-nitrobenzoate

N,N-Dimethy-1,3-propanediamine (1.41 g) was added to ethyl 4-chloro-3-nitrobenzoate (1.59 g) and stirred for 12 hours at 125° C. The reaction mixture, with ethyl acetate added thereto, was washed with 1N sodium hydroxide aqueous solution, water, and saturated brine successively, dried over sodium sulfate anhydride, and concentrated, thereby yielding the entitled compound (2.07 g) as brown oil.

$^1$H-NMR (CDCl$_3$) δ: 1.39 (3H, t, J=7.3 Hz), 1.88 (2H, quintet, J=6.4 Hz), 2.27 (6H, s), 2.45 (2H, t, J=6.4 Hz), 3.44 (2H, td, J=6.4, 4.9 Hz), 4.36 (2H, q, J=7.3 Hz), 6.88 (1H, d, J=8.8 Hz), 8.04 (1H, dd, J=8.8, 2.0 Hz), 8.87 (1H, d, J=2.0 Hz), 8.98 (1H, brs).

(3) Ethyl 3-amino-4-{[3-(dimethylamino)propyl]amino}benzoate

10% of palladium-carbon (0.40 g) was added to a solution containing ethyl 4-{[3-(dimethylamino)propyl]amino}-3-nitrobenzoate (2.02 g) in ethanol (20 ml) and stirred for 5 hours under a hydrogen gas atmosphere at room temperature. After the catalyst was removed out by filtration, the filtrate was concentrated, thereby yielding the entitled compound (1.85 g) as dark red oil.

$^1$H-NMR (CDCl$_3$) δ: 1.36 (3H, t, J=7.3 Hz), 1.84 (2H, quintet, J=6.4 Hz), 2.27 (6H, s), 2.44 (2H, t, J=6.4 Hz), 3.26 (2H, t, J=6.4 Hz), 3.27 (2H, brs), 4.30 (2H, q, J=7.3 Hz), 4.7–5.4 (1H, brs), 6.56 (1H, d, J=8.8 Hz), 7.38 (1H, d, J=2.0 Hz), 7.57 (1H, dd, J=8.8, 2.0 Hz).

(4) Ethyl 1-[3-(dimethylamino)propyl]-2-heptadecyl-1H-benzimidazole-5-carboxylate Triethylamine (1.05 ml) was added to a solution containing ethyl 3-amino-4-{[3-(dimethylamino)propyl]amino}benzoate (1.83 g) in chloroform (20 ml), and then stearoyl chloride (2.07 g) was added thereto while being cooled with ice. After being stirred for 4 hours at room temperature, the reaction mixture was diluted with chloroform, washed with saturated sodium hydrogencarbonate aqueous solution and water successively, dried over sodium sulfate anhydride, and concentrated. Concentrated hydrochloric acid (5.00 ml) was added to a solution containing the residue (3.95 g) in ethanol (30 ml). After being stirred for 3 hours at 90° C., the reaction mixture was neutralized with 5N sodium hydroxide aqueous solution (12 ml) and concentrated. The residue, with ethyl acetate added thereto, was washed with water and saturated brine successively, dried over sodium sulfate anhydride, and concentrated. The residue (3.28 g) was purified by silica gel column chromatography (silica gel 50 g, chloroform:methanol=20:1–10:1), thereby yielding the entitled compound (2.99 g) as orange solid.

$^1$H-NMR (CDCl$_3$) δ: 0.88 (3H, t, J=6.8 Hz), 1.2–1.4 (26H, m), 1.40 (3H, t, J=7.3 Hz), 1.46 (2H, m), 1.87–1.98 (4H, m), 2.22 (6H, s), 2.26 (2H, t, J=6.6 Hz), 2.89 (2H, t, J=7.8 Hz), 4.21 (2H, t, J=7.3 Hz), 4.39 (2H, q, J=7.3 Hz), 7.36 (1H, d, J=8.3 Hz), 7.97 (1H, dd, J=8.3, 2.0 Hz), 8.44 (1H, d, J=2.0 Hz).

Example 18

Ethyl 1-[3-(dimethylamino)propyl]-2-heptadecyl-1H-benzimidazole-5-carboxylate monohydrochloride (Compound 18)

4N Hydrochloric acid/ethyl acetate solution (0.19 ml) was added to a solution containing ethyl 1-[3-(dimethylamino) propyl]-2-heptadecyl-1H-benzimidazole-5-carboxylate (0.38 g) in ethyl acetate (4 ml). After being stirred for 10 minutes at room temperature, the reaction mixture was concentrated. The residue was recrystallized with ethyl acetate, thereby yielding the entitled compound (0.29 g) as grayish yellow solid.

$^1$H-NMR (CDCl$_3$) 67 : 0.88 (3H, t, J=7.1 Hz), 1.2–1.4 (26H, m), 1.40 (3H, t, J=7.3 Hz), 1.46 (2H, m), 1.92 (2H, quintet, J=7.8 Hz), 2.44 (2H, m), 2.76 (6H, s), 2.89 (2H, t, J=7.8 Hz), 3.03 (2H, t, J=7.8 Hz), 4.39 (2H, q, J=7.3 Hz), 4.41 (2H, t, J=6.8 Hz), 7.46 (1H, d, J=8.3 Hz), 7.99 (1H, dd, J=8.3, 1.5 Hz), 8.45 (1H, d, J=1.5 Hz).

Example 19

1-[3-(Dimethylamino)propyl]-2-heptadecyl-N-methyl-1H-benzimidazole-5-carboxamide (Compound 19)

(1) 4-Chloro-N-methyl-3-nitrobenzamide

Thionyl chloride (0.65 ml) was added to a solution containing 4-chloro-3-nitrobenzoic acid (1.50 g) in N,N-dimethylformamide (15 ml) and stirred for 30 minutes at room temperature. Methylamine hydrochloride (1.21 g) and triethylamine (3.11 ml) were added to the reaction mixture. After being stirred for 1 hour at room temperature, the reaction mixture was concentrated. The residue, with ethyl acetate added thereto, was washed with water, 1N sodium hydroxide aqueous solution, 1N hydrochloric acid aqueous solution and saturated brine successively, dried over sodium sulfate anhydride, and concentrated. The yellow solid residue was purified by silica gel column chromatography (silica gel 10 g, chloroform:methanol=1:0–10:1), thereby yielding the entitled compound (0.97 g) as pale yellow solid.

$^1$H-NMR (CDCl$_3$) δ: 3.04 (3H, d, J=4.9 Hz), 6.61 (1H, brs), 7.63 (1H, d, J=8.8 Hz), 7.96 (1H, dd, J=8.8, 2.0 Hz), 8.28 (1H, d, J=2.0 Hz).

(2) 4-{[3-(Dimethylamino)propyl]amino}-N-methyl-3-nitrobenzamide

N,N-Dimethy-1,3-propanediamine (1.39 g) was added to 4-chloro-N-methyl-3-nitrobenzamide (1.46 g) and the mixture was stirred for 5 hours at 120° C. The reaction mixture, with ethyl acetate added thereto, was washed with 1N sodium hydroxide aqueous solution and saturated brine successively, dried over sodium sulfate anhydride, and concentrated, thereby yielding the entitled compound (1.88 g) as yellow solid.

$^1$H-NMR (CDCl$_3$) δ: 1.88 (2H, m), 2.26 (6H, s), 2.45 (2H, t, J=6.4 Hz), 3.01 (3H, d, J=4.9 Hz), 3.43 (2H, td, J=6.8, 5.4 Hz), 6.31 (1H, brs), 6.91 (1H, d, J=8.8 Hz), 7.95 (1H, dd, J=8.8, 2.0 Hz), 8.54 (1H, d, J=2.0 Hz), 8.88 (1H, brt).

(3) 3-Amino-4-{[3-(dimethylamino)propyl]amino}-N-methylbenzamide

10% of palladium-carbon (0.40 g) was added to a solution containing 4-{[3-(dimethylamino)propyl]amino}-N-methyl-3-nitrobenzamide (1.88 g) in ethanol (30 ml) and the mixture was stirred for 14 hours under a hydrogen gas atmosphere at room temperature. After the catalyst was removed out by filtration, the filtrate was concentrated, thereby yielding the entitled compound (1.63 g) as purple solid.

$^1$H-NMR (CDCl$_3$) δ: 1.86 (2H, quintet, J=6.4 Hz), 2.29 (6H, s), 2.48 (2H, t, J=6.4 Hz), 2.96 (3H, d, J=4.9 Hz), 3.24 (2H, t, J=6.4 Hz), 3.39 (2H, brs), 6.01 (1H, brs), 6.54 (1H, d, J=7.8 Hz), 7.17 (1H, dd, J=7.8, 2.0 Hz), 7.21 (1H, d, J=2.0 Hz).

(4) 1-[3-(Dimethylamino)propyl]-2-heptadecyl-N-methyl-1H-benzimidazole-5-carboxamide Triethylamine (0.77 ml) was added to a solution containing 3-amino-4-{[3-(dimethylamino)propyl]amino}-N-methylbenzamide (1.44 g) in chloroform (10 ml), and then a solution containing stearoyl chloride (1.51 g) in chloroform (5 ml) was added thereto while being cooled with ice. After being stirred for 1.5 hours at room temperature, the reaction mixture was diluted with chlorofonr, washed with saturated sodium hydrogencarbonate aqueous solution and water successively, dried over sodium sulfate anhydride, and concentrated. Concentrated hydrochloric acid (4.00 ml) was added to a solution containing the residue (2.78 g) in ethanol (25 ml). After being stirred for 1.5 hours at 90° C., the reaction mixture was concentrated. The residue, with ethyl acetate added thereto, was washed with 4N sodium hydroxide aqueous solution and saturated brine successively, dried over sodium sulfate anhydride, and concentrated. The residue (2.77 g) was purified by silica gel column chromatography (silica gel 50 g, chloroform:methanol=50:1–10:1), thereby yielding the entitled compound (2.11 g) as grayish yellow solid.

$^1$H-NMR (CDCl$_3$) δ: 0.88 (3H, t, J=6.8 Hz), 1.2–1.4 (26H, m), 1.45 (2H, m), 1.85–1.97 (4H, m), 2.22 (6H, s), 2.25 (2H, t, J=6.6 Hz), 2.89 (2H, t, J=7.8 Hz), 3.04 (3H, d, J=4.4 Hz), 4.20 (2H, t, J=7.1 Hz), 6.22 (1H, q, J=4.4 Hz), 7.38 (1H, d, J=8.3 Hz), 7.77 (1H, dd, J=8.3, 1.5 Hz), 8.02 (1H, d, J=1.5 Hz).

Example 20

1-[3-(Dimethylamino)propyl]-2-heptadecyl-N-methyl-1H-benzimidazole-5-carboxamide monohydrochloride (Compound 20)

4N Hydrochloric acid/ethyl acetate solution (0.45 ml) was added to a solution containing 1-[3-(dimethylamino)propyl]-2-heptadecyl-N-methyl-1H-benzimidazole-5-carboxamide (0.90 g) in ethyl acetate (10 ml). After being stirred for 10 minutes at room temperature, the reaction mixture was concentrated. The residue was recrystallized with ethyl acetate, thereby yielding the entitled compound (0.70 g) as grayish yellow solid.

$^1$H-NMR (CDCl$_3$) δ: 0.88 (3H, t, J=6.8 Hz), 1.2–1.4 (26H, m), 1.44 (2H, m), 1.87 (2H, quintet, J=7.8 Hz), 2.40 (2H, m), 2.76 (6H, s), 2.87 (2H, t, J=7.8 Hz), 3.02 (3H, d, J=4.9 Hz), 3.03 (2H, m), 4.36 (2H, t, J=7.1 Hz), 6.69 (1H, brs), 7.44 (1H, d, J=8.3 Hz), 7.74 (1H, dd, J=8.3, 1.5 Hz), 8.06 (1H, d, J=1.5 Hz).

Example 21

1-[3-(Dimethylamino)propyl]-2-heptadecyl-N,N-dimethyl-1H-benzimidazole-5-carboxamide (Compound 21)

(1) 4-Chloro-N,N-dimethyl-3-nitrobenzamide

Triethylamine (3.48 ml) was added to a solution containing 4-chloro-3-nitrobenzoic acid (5.04 g) in N,N-dimethylformamide (25 ml) while being cooled with ice, and then pivaloyl chloride (3.08 ml) was added thereto. The mixture was stirred for 15 minutes, and then dimethylamine hydrochloride (2.24 g) and triethylamine (3.83 ml) were added thereto. The reaction mixture was stirred for 15 minutes while being cooled with ice and futher stirred for 14 hours at room temperature, and then concentrated. The residue, with ethyl acetate added thereto, was washed with water, 1N sodium hydroxide aqueous solution and saturated brine successively, dried over sodium sulfate anhydride, and concentrated, thereby yielding the entitled compound (4.85 g) as yellow solid.

$^1$H-NMR (CDCl$_3$) δ: 3.02 (3H, s), 3.13 (3H, s), 7.61 (2H, m), 7.96 (1H, d, J=1.5 Hz).

(2) 4-{[3-(Dimethylamino)propyl]amino}-N,N-dimethyl-3-nitrobenzamide

N,N-Dimethy-1,3-propanediamine (1.95 g) was added to 4-chloro-N,N-dimethyl-3-nitrobenzamide (2.18 g) and stirred for 2 hours at 90° C. The reaction mixture, with ethyl acetate added thereto, was washed with 1N sodium hydroxide aqueous solution, water and saturated brine successively, dried over sodium sulfate anhydride, and concentrated, thereby yielding the entitled compound (2.83 g) as yellowish orange oil.

$^1$H-NMR (CDCl$_3$) δ: 1.88 (2H, m), 2.26 (6H, s), 2.44 (2H, t, J=6.3 Hz), 3.09 (6H, s), 3.42 (2H, td, J=6.8, 4.9 Hz), 6.90 (1H, d, J=9.3 Hz), 7.60 (1H, dd, J=9.3, 2.0 Hz), 8.32 (1H, d, J=2.0 Hz), 8.74 (1H, brt).

(3) 3-Amino-4-{[3-(dimethylamino)propyl]amino}-N,N-dimethylbenzamide

10% of palladium-carbon (0.56 g) was added to a solution containing 4-{[3-(dimethylamino)propyl]amino}-N,N-dimethyl-3-nitrobenzamide (2.82 g) in ethanol (20 ml) and the mixture was stirred for 13 hours under a hydrogen gas atmosphere at room temperature. After the catalyst was removed out by filtration, the filtrate was concentrated, thereby yielding the entitled compound (2.59 g) as dark red solid.

$^1$H-NMR (CDCl$_3$) δ: 1.84 (2H, quintet, J=6.4 Hz), 2.27 (6H, s), 2.44 (2H, t, J=6.4 Hz), 3.05 (6H, s), 3.21 (2H, t, J=6.4 Hz), 3.34 (2H, brs), 4.2–4.8 (1H, brs), 6.56 (1H, d, J=7.8 Hz), 6.85 (1H, d, J=2.0 Hz), 6.91 (1H, dd, J=7.8, 2.0 Hz).

(4) 1-[3-(Dimethylamino)propyl]-2-heptadecyl-N,N-dimethyl-1H-benzimidazole-5-carboxamide Triethylamine (1.46 ml) was added to a solution containing 3-amino-4-{[3-(dimethylamino)propyl]amino}-N,N-dimethylbenzamide (2.57 g) in chloroform (20 ml), and then stearoyl chloride (2.89 g) was added thereto while being cooled with ice. After being stirred for 2 hours at room temperature, the reaction mixture was diluted with chloroform, washed with saturated sodium hydrogencarbonate aqueous solution and water successively, dried over sodium sulfate anhydride, and concentrated. Concentrated hydrochloric acid (7.5 ml) was added to a solution containing the residue (5.53 g) in ethanol (30 ml). After being stirred for 3 hours at 90° C., the reaction mixture was neutralized with 5N sodium hydroxide aqueous solution (18 ml) and concentrated. The residue, with ethyl acetate added thereto, was washed with water and saturated brine successively, dried over sodium sulfate anhydride, and concentrated. The residue (4.33 g) was purified by silica gel column chromatography (silica gel 50 g, chloroform:methanol=10:1), thereby yielding the entitled compound (4.21 g) as pink wax.

$^1$H-NMR (CDCl$_3$) δ: 0.88 (3H, t, J=6.8 Hz), 1.2–1.4 (26H, m), 1.45 (2H, m), 1.88–1.97 (4H, m), 2.22 (6H, s), 2.25 (2H, t, J=6.6 Hz), 2.89 (2H, t, J=8.1 Hz), 3.08 (6H, brs), 4.20 (2H, t, J=7.1 Hz), 7.36 (2H, s), 7.75 (1H, s).

Example 22

1-[3-(Dimethylamino)propyl]-2-heptadecyl-N,N-dimethyl-1H-benzimidazole-5-carboxamide monohydrochloride (Compound 22)

4N Hydrochloric acid/ethyl acetate solution (0.20 ml) was added to a solution containing 1-[3-(dimethylamino) propyl]-2-heptadecyl-N,N-dimethyl-1H-benzimidazole-5-carboxamide (0.41 g) in ethyl acetate (4 ml). After being stirred for 10 minutes at room temperature, the reaction mixture was concentrated. The residue was recrystallized with a mixed solution of n-hexane-ethyl acetate, thereby yielding the entitled compound (0.32 g) as grayish yellow solid.

$^1$H-NMR (CDCl$_3$) δ: 0.88 (3H, t, J=6.8 Hz), 1.2–1.4 (26H, m), 1.46 (2H, m), 1.90 (2H, quintet, J=7.8 Hz), 2.39 (2H, m), 2.73 (6H, s), 2.87 (2H, t, J=7.8 Hz), 2.97 (2H, t, J=7.8 Hz), 3.04 (3H, brs), 3.13 (3H, brs), 4.38 (2H, t, J=7.1 Hz), 7.36 (1H, dd, J=8.3, 1.5 Hz), 7.44 (1H, d, J=8.3 Hz), 7.76 (1H, d, J=1.5 Hz).

Example 23

3-(2-Heptadecyl-5-methyl-1H-benzimidazol-1-yl)-N,N-dimethyl-1-propanamine (Compound 23)

(1) N$^1$,N$^1$-Dimethyl-N$^3$-(4-methyl-2-nitrophenyl)-1,3-propanediamine

N,N-Dimethyl-1,3-propanediamine (5.114 g) was added to 4-chloro-3-nitrotoluene (3.434 g) and the mixture was stirred for 14 hours at 125° C. The reaction mixture, with toluene added thereto, was washed with saturated sodium hydrogencarbonate aqueous solution and saturated brine successively, dried over sodium sulfate anhydride, and concentrated. The residue (4.93 g) was purified by silica gel column chromatography (silica gel 50 g, chloroform:methanol=1:0–10:1), thereby yielding the entitled compound (4.39 g) as reddish orange oil.

$^1$H-NMR (CDCl$_3$) δ: 1.68 (3H, s), 1.86 (2H, quintet, J=6.8 Hz), 2.25 (6H, s), 2.41 (2H, t, J=6.8 Hz), 3.36 (2H, m), 6.79 (1H, d, J=8.8 Hz), 7.25 (1H, d, J=8.8 Hz), 7.97 (1H, s), 8.25(1H, brs).

(2) N$^1$-[3-(Dimethylamino)propyl]-4-methyl-1,2-benzenediamine

10% of palladium-carbon (0.48 g) was added to a solution containing N$^1$,N$^1$-dimethyl-N$^3$-(4-methyl-2-nitrophenyl)-1,3-propanediamine (2.37 g) in ethanol (20 ml) and the mixture was stirred for 4 hours under a hydrogen gas atmosphere at room temperature. After the catalyst was removed out by filtration, the filtrate was concentrated, thereby yielding the entitled compound (2.054 g) as dark green solid.

$^1$H-NMR (CDCl$_3$) δ: 1.82 (2H, quintet, J=6.8 Hz), 2.21 (3H, s), 2.25 (6H, s), 2.42 (2H, t, J=6.8 Hz), 3.14 (2H, t, J=6.8 Hz), 3.34 (2H, brs), 6.53–6.61 (3H, m).

(3) 3-(2-Heptadecyl-5-methyl-1H-benzimidazol-1-yl)-N,N-dimethyl-1-propanamine

Triethylamine (0.557 g) was added to a solution containing N$^1$-[3-(dimethylamino)propyl]4-methyl-1,2-benzenediamine (1.037 g) in dichloromethane (5 ml), and then a solution containing stearoyl chloride (1.515 g) in dichloromethane (5 mnl) was added thereto while being cooled with ice. After being stirred for 4.5 hours at room temperature, the reaction mixture was diluted with dichloromethane, washed with saturated sodium hydrogencarbonate aqueous solution and saturated brine successively, dried over sodium sulfate anhydride, and concentrated. Concentrated hydrochloric acid (3.5 ml) was added to a solution containing the residue (1.97 g) in ethanol (20 ml). After being stiffed for 5.5 hours at 90° C., the reaction mixture was concentrated. The residue, with chloroform added thereto, was washed with 0.5N sodium hydroxide aqueous solution and saturated brine successively, dried over sodium sulfate anhydride, and concentrated. The residue (1.03 g) was purified by silica gel column chromatography (silica gel 30 g, chloroform:methanol=50:1–1:1), thereby yielding the entitled compound (0.714 g) as pale yellow solid.

$^1$H-NMR (CDCl$_3$) δ: 0.88 (3H, t, J=6.8 Hz), 1.2–1.4 (26H, m), 1.44 (2H, m), 1.85–1.94 (4H, m), 2.22 (6H, s), 2.26 (2H, t, J=6.6 Hz), 2.46 (3H, s), 2.85 (2H, t, J=7.8 Hz), 4.15 (2H, t, J=7.3 Hz), 7.03 (1H, d, J=8.3 Hz), 7.21 (1H, d, J=8.3 Hz), 7.50 (1H, s).

Example 24

3-(2-Heptadecyl-5-methyl-1H-benzimidazol-1-yl)-N,N-dimethyl-1-propanamine monohydrochloride (Compound 24)

4N Hydrochloric acid/ethyl acetate solution (0.28 ml) was added to a solution containing 3-(2-heptadecyl-5-methyl-1H-benzimidazol-1-yl)-N,N-dimethyl-1-propanamine (0.34 g) in ethyl acetate (5 ml). After being stirred for 10 minutes at room temperature, the reaction mixture was concentrated. The residue was recrystallized with a mixed solution of ethanol-ethyl acetate, thereby yielding the entitled compound (0.304 g) as white solid.

$^1$H-NMR (CDCl$_3$) δ: 0.88 (3H, t, J=6.6 Hz), 1.2–1.4 (26H, m), 1.42 (2H, m), 1.89 (2H, quintet, J=7.8 Hz), 2.45 (2H, m), 2.46 (3H, s), 2.74 (6H, s), 2.97–3.04 (4H, m), 4.42 (2H, t, J=7.1 Hz), 7.16 (1H, d, J=8.3 Hz), 7.41 (1H, d, J=8.3 Hz), 7.57 (1H, s).

Example 25

3-(7-Chloro-2-heptadecyl-1H-benzimidazol-1-yl)-N,N-dimethyl-1-propanamine (Compound 25)

(1) N$^1$-(2-Chloro-6-nitrophenyl)-N$^3$,N$^3$-dimethyl-1,3-propanediamine

N,N-Dimethyl-1,3-propanediamine (5.125 g) was added to 2,3-dichloronitrobenzene (3.841 g) and stirred for 13.5 hours at 125° C. The reaction mixture, with toluene added thereto, was washed with saturated sodium hydrogencarbonate aqueous solution and saturated brine successively, dried over sodium sulfate anhydride, and concentrated. The residue (4.881 g) was purified by silica gel column chromatography (silica gel 100 g, chloroform:methanol=1:0–50:1), thereby yielding the entitled compound (4.53 g) as reddish orange oil.

$^1$H-NMR (CDCl$_3$) δ: 1.75 (2H, m), 2.23 (6H, s), 2.40 (2H, m), 3.35 (2H, m), 6.67 (1H, m), 7.34 (1H, brs), 7.45 (1H, dd, J=7.8, 1.5 Hz), 7.82 (1H, dd, J=8.3, 1.5 Hz).

(2) 3-Chloro-N$^2$-[3-(dimethylamino)propyl]-1,2-benzenediamine

A solution containing tin(II) chloride dihydrate (4.040 g) in concentrated hydrochloric acid (5.85 ml) was added to a solution containing N$^1$-(2-chloro-6-nitrophenyl)-N$^3$,N$^3$-dimethyl-1,3-propanediamine (1.289 g) in concentrated hydrochloric acid (4.2 ml) and the mixture was stirred for 14 hours at room temperature. The reaction mixture was alkalified with 10% sodium hydroxide aqueous solution while being cooled with ice and extracted with diethyl ether. The extract was washed with saturated brine, dried over sodium sulfate anhydride, and concentrated, thereby yielding the entitled compound (1.130 g) as orange solid.

$^1$H-NMR (CDCl$_3$) δ: 1.74 (2H, m), 2.23 (6H, s), 2.44 (2H, t, J=6.8 Hz), 2.99 (2H, m), 3.2–3.7 (1H, brs), 4.26 (2H, brs), 6.57 (1H, dd, J=7.3, 1.5 Hz), 6.71–6.79 (2H, m).

(3) 3-(7-Chloro-2-heptadecyl-1H-benzimidazol-1-yl)-N,N-dimethyl-1-propanamine

Triethylamine (0.587 g) was added to a solution containing 3-chloro-N$^2$-[3-(dimethylamino)propyl]-1,2-benzenediamine (1.100 g) in dichloromethane (22 ml), and then stearoyl chloride (1.610 g) was added thereto while being cooled with ice. After being stirred for 4.5 hours at room temperature, the reaction mixture was diluted with dichloromethane, washed with saturated sodium hydrogencarbonate aqueous solution and saturated brine successively, dried over sodium sulfate anhydride, and concentrated. Concentrated hydrochloric acid (4.0 ml) was added to a solution containing the residue (3.451 g) in ethanol (24 ml). After being stirred for 4 hours at 90° C., the reaction mixture was concentrated. The residue, with ethyl acetate added thereto, was washed with saturated sodium hydrogencarbonate aqueous solution and saturated brine successively, dried over sodium sulfate anhydride, and concentrated. The residue (2.95 g) was purified by silica gel column chromatography (silica gel 92 g, chloroform:methanol=1:0–100:1), thereby yielding the entitled compound (1.271 g) as pale yellow solid.

$^1$H-NMR (CDCl$_3$) δ: 0.88 (3H, t, J=6.8 Hz), 1.2–1.4 (26H, m), 1.46 (2H, m), 1.89 (2H, quintet, J=7.8 Hz), 1.98 (2H, m), 2.24 (6H, s), 2.34 (2H, t, J=6.8 Hz), 2.88 (2H, t, J=7.8 Hz), 4.46 (2H, t, J=7.6 Hz), 7.11 (1H, t, J=7.8 Hz), 7.16 (1H, dd, J=7.8, 1.0 Hz), 7.60 (1H, dd, J=7.8, 1.0 Hz).

Example 26

3-(7-Chloro-2-heptadecyl-1H-benzimidazol-1-yl)-N,N-dimethyl-1-propanamine monohydrochloride (Compound 26)

4N Hydrochloric acid/ethyl acetate solution (0.19 ml) was added to a solution containing 3-(7-chloro-2-heptadecyl-1H-benzimidazol-1-yl)-N,N-dimethyl-1-propanamine (0.363 g) in ethyl acetate (3 ml). After being stirred for 10 minutes at room temperature, the reaction mixture was concentrated. The residue was recrystallized with a mixed solution of ethanol-ethyl acetate, thereby yielding the entitled compound (0.284 g) as white solid.

$^1$H-NMR (CDCl$_3$) δ: 0.88 (3H, t, J=6.8 Hz), 1.2–1.4 (26H, m), 1.47 (2H, m), 1.90 (2H, quintet, J=7.8 Hz), 2.44 (2H, m), 2.80 (6H, s), 2.89 (2H, t, J=7.8 Hz), 3.10 (2H, t, J=8.1 Hz), 4.61 (2H, t, J=7.8 Hz), 7.15 (1H, t, J=7.3 Hz), 7.19 (1H, d, J=7.3 Hz), 7.64 (1H, d, J=7.3 Hz).

Example 27

1-[3-(Dimethylamino)propyl]-2-heptadecyl-1H-benzimidazol-5-amine (Compound 27)

Acetic anhydride (2.042 g) was added to 4-chloro-3-nitroaniline (3.451 g) and the mixture was stirred for 20 hours at room temperature. Water was added to the reaction mixture and the resulting crystals were collected by filtration, thereby yielding yellow solid (4.219 g).

N,N-Dimethyl-1,3-propanediamine (2.447 g) was added to this solid (2.056 g) and the mixture was stiffed for 22 hours at 80° C. and further stirred for 2 hours at 120° C. The reaction mixture was concentrated and the residue (4.2 g) was purified by silica gel column chromatography (silica gel 80 g, chloroform:methanol=50:1–10:1), thereby yielding reddish brown oil (2.36 g) which contained N-{4-[[3-(dimethylamino)propyl]amino]-3-nitrophenyl}acetamide as a main component.

10% of palladium-carbon (0.46 g) was added to a solution containing this oil (2.300 g) in ethanol (20 mnl) and the mixture was stirred for 23 hours under a hydrogen gas atmosphere at room temperature. After the catalyst was removed out by filtration, the filtrate was concentrated, thereby yielding reddish brown solid (2.034 g) which contained N-{3-amino-4-[[3-(dimethylamino)propyl]amino]phenyl}acetamide as a main component.

Triethylamine (2.707 g) was added to a solution containing this solid (2.034 g) in chloroform (20 ml), and then stearoyl chloride (2.707 g) was added thereto while being cooled with ice. After being stirred for 6 hours at room temperature, the reaction mixture was diluted with dichloromethane, washed with saturated sodium hydrogencarbonate aqueous solution and saturated brine successively, dried over sodium sulfate anhydride, and concentrated. Concentrated hydrochloric acid (6.8 ml) was added to a solution containing the residue (4.34 g) in ethanol (40 ml). After being stirred for 5 hours at 90° C., the reaction mixture, with ethanol (10 ml) and ethyl acetate (100 ml) added thereto, was washed with 1N sodium hydroxide aqueous solution and saturated brine successively, dried over sodium sulfate anhydride, and concentrated. The residue (4.37 g) was purified by silica gel column chromatography (silica gel 100 g, chloroform:methanol=20:1), thereby yielding the entitled compound (1.513 g) as reddish orange solid.

$^1$H-NMR (CDCl$_3$) δ: 0.88 (3H, t, J=6.8 Hz), 1.2–1.4 (26H, m), 1.43 (2H, m), 1.85 (2H, m), 1.91 (2H, m), 2.21 (6H, s), 2.25 (2H, t, J=6.8 Hz), 2.81 (2H, t, J=7.8 Hz), 2.9–3.5 (2H, brs), 4.10 (2H, t, J=7.1 Hz), 6.64 (1H, dd, J=8.8, 2.0 Hz), 7.02 (1H, d, J=2.0 Hz), 7.10 (1H, d, J=8.8 Hz).

Example 28

N-[3-(Dimethylamino)propyl]-1-octadecyl-1H-benzimidazole-2-carboxamide (Compound 28)

(1) N-(2-Nitrophenyl)-1-octadecanamine

Octadecylamine (11.858 g) was added to 2-chloronitrobenzene (3.151 g) and the mixture was stirred for 17.5 hours at 125° C. After n-hexane was added to the reaction mixture, solid materials were crushed well and removed out by filtration. The filtrate was concentrated and the residue (9.13 g) was purified by silica gel column chromatography (silica gel 90 g, n-hexane:ethyl acetate=50:1), thereby yielding the entitled compound (7.642 g) as yellow solid.

$^1$H-NMR (CDCl$_3$) δ: 0.88 (3H, t, J=6.8 Hz), 1.2–1.4 (28H, m), 1.44 (2H, m), 1.73 (2H, quintet, J=7.3 Hz), 3.29 (2H, td, J=7.3, 4.9 Hz), 6.62 (1H, ddd, J=8.8, 6.8, 1.0 Hz), 6.84 (1H, d, J=8.8 Hz), 7.42 (1H, ddd, J=8.8, 6.8, 1.5 Hz), 8.05 (1H, brs), 8.17 (1H, dd, J=8.8, 1.5 Hz).

(2) N-Octadecyl-1,2-benzenediamine

10% of palladium-carbon (1.52 g) was added to a solution containing N-(2-nitrophenyl)-1-octadecanamine (7.600 g) in ethyl acetate (76 ml) and the mixture was stirred for 18 hours under a hydrogen gas atmosphere at room temperature. After the catalyst was removed out by filtration, the filtrate was concentrated, thereby yielding the entitled compound (6.95 g) as pink solid.

$^1$H-NMR (CDCl$_3$) δ: 0.88 (3H, t, J=6.6 Hz), 1.2–1.4 (28H, m), 1.42 (2H, m), 1.66 (2H, quintet, J=7.3 Hz), 3.09 (2H, t, J=7.3 Hz), 3.27 (3H, brs), 6.63–6.72 (3H, m), 6.82 (1H, dd, J=6.8, 1.5 Hz).

(3) Ethyl 1-octadecyl-1H-benzimidazole-2-carboxylate

Ethyl glyoxylate (7.861 g) and iodide (4.886 g) were added to a solution containing N-octadecyl-1,2-benzenediamine (6.940 g) in ethanol (100 ml) and the mixture was stirred for 2 hours at room temperature. A solution containing sodium thiosulfate pentahydrate (4.813 g) in water (60 ml) was added dropwise to the reaction mixture while being stirred. The reaction mixture, with ethyl acetate added thereto, was washed with saturated brine, dried over sodium sulfate anhydride, and concentrated. The residue (10.06 g) was purified by silica gel column chromatography (silica gel 255 g, chloroform), thereby yielding the entitled compound (6.442 g) as pale yellow solid.

$^1$H-NMR (CDCl$_3$) δ: 0.88 (3H, t, J=6.8 Hz), 1.2–1.4 (30H, m), 1.50 (3H, t, J=7.1 Hz), 1.86 (2H, m), 4.53 (2H, q, J=7.1 Hz), 4.63 (2H, t, J=7.6 Hz), 7.33–7.44 (2H, m), 7.45 (1H, d, J=8.3 Hz), 7.93 (1H, d, J=7.8 Hz).

(4) N-[3-(Dimethylamino)propyl]-1-octadecyl-1H-benzimidazole-2-carboxamide

N,N-Dimethyl-1,3-propanediamine (0.818 g) was added to ethyl 1-octadecyl-1H-benzimidazole-2-carboxylate (1.771 g) and the mixture was stirred for 15 hours at 125° C. The reaction mixture was purified by silica gel column chromatography (silica gel 60 g, chloroform:methanol=30:1), thereby yielding the entitled compound (1.746 g) as pale yellow oil.

$^1$H-NMR (CDCl$_3$) δ: 0.88 (3H, t, J=6.8 Hz), 1.2–1.4 (30H, m), 1.77–1.91 (4H, m), 2.25 (6H, s), 2.41 (2H, t, J=6.8 Hz), 3.52 (2H, m), 4.70 (2H, t, J=7.3 Hz), 7.29–7.38 (2H, m), 7.43 (1H, d, J=7.8 Hz), 7.76 (1H, d, J=7.3 Hz), 8.25 (1H, brt).

Example 29

N-[3-(Dimethylamino)propyl]-1-octadecyl-1H-benzimidazole-2-carboxamide monohydrochloride (Compound 29)

4N Hydrochloric acid/ethyl acetate solution (0.25 ml) was added to a solution containing N-[3-(dimethylamino)propyl]-1-octadecyl-1H-benzimidazole-2-carboxamide (0.499 g) in ethyl acetate (5 ml) and stirred for 10 minutes at room temperature. The reaction mixture, with ethanol (0.3 ml) and ethyl acetate (1 ml) added thereto, was dissolved by heating and then cooled naturally. The depositing crystals were collected by filtration, thereby yielding the entitled compound (0.419 g) as white solid.

$^1$H-NMR (CDCl$_3$) δ: 0.88 (3H, t, J=6.8 Hz), 1.2–1.4 (30H, m), 1.85 (2H, m), 2.26 (2H, m), 2.85 (6H, s), 3.19 (2H, t, J=8.1 Hz), 3.64 (2H, m), 4.65 (2H, t, J=7.3 Hz), 7.32 (1H, m), 7.37 (1H, m), 7.43 (1H, d, J=7.8 Hz), 7.75 (1H, d, J=8.3 Hz), 8.25 (1H, t, J=6.4 Hz).

Example 30

2-[(4-Methylpiperazinyl)carbonyl]-1-octadecyl-1H-benzimidazole (Compound 30)

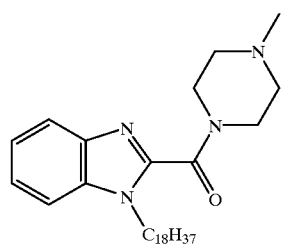

1-Methylpiperazine (1.811 g) was added to ethyl 1-octadecyl-1H-benzimidazole-2-carboxylate (1.601 g) and the mixture was stirred for 48 hours at 75° C. The reaction mixture was purified by silica gel column chromatography (silica gel 60 g, chloroform:methanol=1:0–50:1), thereby yielding the entitled compound (1.070 g) as pale yellow solid.

¹H-NMR (CDCl₃) δ: 0.88 (3H, t, J=6.8 Hz), 1.2–1.4 (30H, m), 1.84 (2H, m), 2.34 (3H, s), 2.47 (2H, m), 2.54 (2H, m), 3.8–4.0 (4H, m), 4.38 (2H, t, J=7.3 Hz), 7.31 (1H, brt, J=7.6 Hz), 7.36 (1H, brt, J=7.6 Hz), 7.41 (1H, d, J=7.3 Hz), 7.80 (1H, d, J=7.8 Hz).

Example 31

2-[(4-Methylpiperazinyl)carbonyl]-1-octadecyl-1H-benzimidazole monohydrochloride (Compound 31)

4N Hydrochloric acid/ethyl acetate solution (0.18 ml) was added to a solution containing 2-[(4-methylpiperazinyl)carbonyl]-1-octadecyl-1H-benzimidazole (0.348 g) in ethyl acetate (4 ml) and the mixture was stirred for 15 minutes at room temperature. The reaction mixture, with ethanol (1 ml) and ethyl acetate (4 ml) added thereto, was dissolved by heating, and then cooled with ice. The depositing crystals were collected by filtration, thereby yielding the entitled compound (0.318 g) as white solid.

¹H-NMR (CDCl₃) δ: 0.88 (3H, t, J=6.8 Hz), 1.2–1.4 (30H, m), 1.83 (2H, m), 2.87 (3H, s), 3.43 (4H, brs), 4.37 (4H, brs), 4.81 (2H, brs), 7.33 (1H, brt, J=7.6 Hz), 7.39 (1H, brt, J=7.6 Hz), 7.44 (1H, d, J=7.8 Hz), 7.75 (1H, d, J=8.3 Hz).

Example 32

2-(2-Henicosyl-1H-benzimidazol-1-yl)-N,N-dimethyl-1-ethanamine (Compound 32)

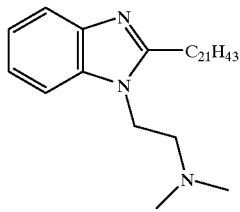

Triethylamine (2.25 ml) was added to a suspension containing n-docosanoic acid (4.930 g) in chloroform (50 ml), and then ethyl chlorocarbonate (1.52 ml) was added thereto while being cooled with ice. After being stirred for 1.5 hours, a solution containing N-[2-(dimethylamino)ethyl]-1,2-benzenediamine (2.593 g) in chloroform (13 ml). After being stirred for 2.5 hours while being cooled with ice, the reaction mixture was diluted with chloroform, washed with saturated sodium hydrogencarbonate aqueous solution and saturated brine successively, dried over sodium sulfate anhydride, and concentrated. Concentrated hydrochloric acid (12.1 ml) was added to a solution containing the residue (8.644 g) in ethanol (87 ml). After being stirred for 2.5 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (6.90 g) was purified by silica gel column chromatography (silica gel 150 g, chloroform:methanol=60:1–30:1), thereby yielding the entitled compound (4.604 g) as pale yellow solid.

¹H-NMR (CDCl₃) δ: 0.88 (3H, t, J=6.8 Hz), 1.2–1.4 (34H, m), 1.45 (2H, m), 1.90 (2H, quintet, J=7.8 Hz), 2.33 (6H, s), 2.63 (2H, t, J=7.8 Hz), 2.87 (2H, t, J=7.8 Hz), 4.21 (2H, t, J=7.8 Hz), 7.20–7.25 (2H, m), 7.30 (1H, m), 7.72 (1H, m).

Example 33

2-(2-Henicosyl-1H-benzimidazol-1-yl)-N,N-dimethyl-1-ethanamine monohydrochloride (Compound 33)

4N Hydrochloric acid/ethyl acetate solution (1.44 ml) was added to a solution containing 2-(2-henicosyl-1H-benzimidazol-1-yl)-N,N-dimethyl-1-ethanamine (2.580 g) in ethyl acetate (26 ml). After being stirred for 30 minutes at room temperature, the reaction mixture was concentrated. The residue was recrystallized with the mixed solution of ethyl acetate-ethanol, thereby yielding the entitled compound (2.269 g) as white crystals.

¹H-NMR (CDCl₃) δ: 0.88 (3H, t, J=6.8 Hz), 1.1–1.4 (34H, m), 1.45 (2H, m), 1.92 (2H, quintet, J=7.8 Hz), 2.73 (6H, s), 3.06 (2H, t, J=7.8 Hz), 3.20 (2H, brt), 4.71 (2H, brt), 7.30–7.36 (2H, m), 7.58 (1H, m), 7.78 (1H, m).

Example 34

1-[3-(Dimethylamino)propyl]-2-henicosyl-N,N-dimethyl-1H-benzimidazole-5-carboxamide Compound 34

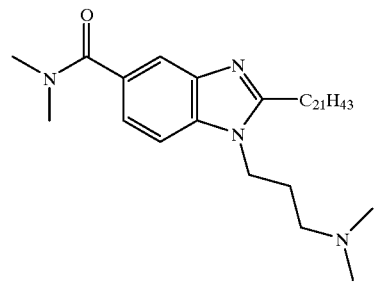

Triethylamine (2.25 ml) was added to a suspension containing n-docosanoic acid (4.918 g) in chloroform (50 ml), and then ethyl chlorocarbonate (1.52 ml) was added thereto while being cooled with ice. The mixture was stirred for 1.5 hours and then a solution containing 3-amino-4-{[3-(dimethylamino)propyl]amino}-N,N-dimethylbenzamide (3.818 g) in chloroform (15 ml) was added thereto. After being stirred for 3 hours while being cooled with ice, the reaction mixture was diluted with chloroform, washed with saturated sodium hydrogencarbonate aqueous solution and saturated brine successively, dried over sodium sulfate anhydride, and concentrated. Concentrated hydrochloric acid (12.1 ml) was added to a solution containing the residue (8.98 g) in ethanol (90 ml). After being stirred for 2 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (7.408 g) was purified by silica gel column chromatography (silica gel 150 g, chloroform:methanol=30:1–10:1), thereby yielding the entitled compound (4.606 g) as white solid.

¹²H-NMR (CDCl₃) δ: 0.88 (3H, t, J=6.8 Hz), 1.2–1.4 (34H, m), 1.45 (2H, m), 1.86–1.97 (4H, m), 2.22 (6H, s), 2.25 (2H, t, J=6.6 Hz), 2.89 (2H, t, J=8.1 Hz), 3.09 (6H, brs), 4.20 (2H, t, J=7.1 Hz), 7.37 (2H, m), 7.75 (1H, s).

Example 35

1-[3-(Dimethylamino)propyl]-2-henicosyl-N,N-dimethyl-1H-benzimidazole-5-carboxamide monohydrochloride (Compound 35)

4 N Hydrochloric acid/ethyl acetate solution (1.20 ml) was added to a solution containing 1-[3-(dimethylamino)propyl]-2-henicosyl-N,N-dimethyl-1H-benzimidazole-5-carboxanmide (2.500 g) in ethyl acetate (25 ml). After being stirred for 30 minutes at room temperature, the reaction mixture was concentrated. The residue was recrystallized with the mixed solution of ethyl acetate-ethanol, thereby yielding the entitled compound (2.193 g) as white crystals.

$^1$H-NMR (CDCl$_3$) δ: 0.88 (3H, t, J=6.8 Hz), 1.2–1.4 (34H, m), 1.46 (2H, m), 1.91 (2H, quintet, J=7.7 Hz), 2.40 (2H, m), 2.73 (6H, s), 2.87 (2H, t, J=7.7 Hz), 2.95 (2H, m), 3.04 (3H, brs), 3.13 (3H, brs), 4.38 (2H, t, J=6.8 Hz), 7.36 (1H, dd, J=8.3, 1.5 Hz), 7.44 (1H, d, J=8.3 Hz), 7.76 (1H, d, J=1.5 Hz).

Example 36

1-[3-(Dimethylamino)propyl]-2-henicosyl-N-methyl-1H-benzimidazole-5-carboxamide

Compound 36

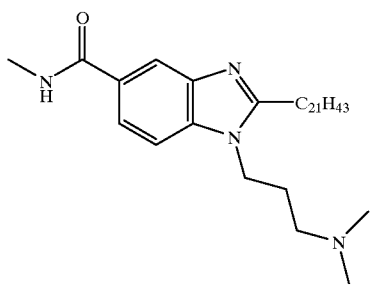

Triethylamine (1.02 ml) was added to a suspension containing n-docosanoic acid (2.265 g) in chloroform (23 ml), and then ethyl chlorocarbonate (0.70 ml) was added thereto while being cooled with ice. The mixture was stirred for 1.5 hours and then a solution containing 3-amino-4-{[3-(dimethylamino)propyl]amnino}-N-methylbenzamide (1.653 g) in chloroform (9 ml) was added thereto. After being stirred for 2.5 hours while being cooled with ice, the reaction mixture was diluted with chloroform, washed with saturated sodium hydrogencarbonate aqueous solution and saturated brine successively, dried over sodium sulfate anhydride, and concentrated. Concentrated hydrochloric acid (5.5 ml) was added to a solution containing the residue (3.506 g) in ethanol (35 ml). After being stirred for 2 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (3.06 g) was purified by silica gel column chromatography (silica gel 75 g, chloroform:methanol=30:1–10:1), thereby yielding the entitled compound (1.829 g) as white solid.

$^1$H-NMR (CDCl$_3$) δ: 0.88 (3H, t, J=6.6 Hz), 1.2–1.4 (34H, m), 1.45 (2H, m), 1.86–1.97 (4H, m), 2.22 (6H, s), 2.25 (2H, t, J=6.6 Hz), 2.89 (2H, t, J=7.8 Hz), 3.04 (3H, d, J=4.9 Hz), 4.20 (2H, t, J=7.1 Hz), 6.16 (1H, m), 7.38 (1H, d, J=8.3 Hz), 7.77 (1H, dd, J=8.3, 1.0 Hz), 8.02 (1H, d, J=1.0 Hz).

Example 37

1-[3-(Dimethylamino)propyl]-2-henicosyl-N-methyl-1H-benzimidazole-5-carboxamide monohydrochloride (Compound 37)

4N Hydrochloric acid/ethyl acetate solution (0.89 ml) was added to a solution containing 1-[3-(dimethylamino)propyl]-2-henicosyl-N-methyl-1H-benzimidazole-5-carboxamide (1.818 g) in a mixture of ethyl acetate (18 ml) and ethanol (1.8 ml). After being stirred for 30 minutes at room temperature, the reaction mixture was concentrated. The residue was recrystallized with the mixed solution of ethyl acetate-ethanol, thereby yielding the entitled compound (1.611 g) as white crystals.

$^1$H-NMR (CDCl$_3$) δ: 0.88 (3H, t, J=6.8 Hz), 1.2–1.4 (34H, m), 1.44 (2H, m), 1.88 (2H, quintet, J=7.8 Hz), 2.40 (2H, m), 2.75 (6H, s), 2.87 (2H, t, J=7.8 Hz), 3.00 (2H, m), 3.03 (3H, d, J=4.9 Hz), 4.37 (2H, t, J=6.8 Hz), 6.56 (1H, m), 7.43 (1H, d, J=8.3 Hz), 7.75 (1H, d, J=8.3 Hz), 8.05 (1H, s).

Example 38

1-[2-(Dimethylamino)ethyl]-2-heptadecyl-N-methyl-1H-benzimidazole-5-carboxamide

Compound 38

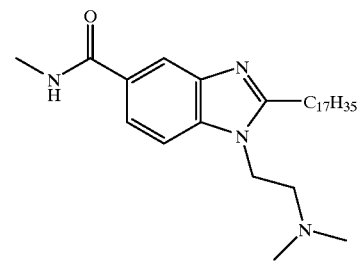

(1) 4-{[2-(Dimethylamino)ethyl]amino}-N-methyl-3-nitrobenzamide

N,N-Dimethylethylenediamine (3.30 ml) was added to 4-chloro-N-methyl-3-nitrobenzamide (3.220 g) and the mixture was stirred for 14 hours at 100° C. The reaction mixture, with ethyl acetate added thereto, was washed with 1N sodium hydroxide aqueous solution and saturated brine successively, dried over sodium sulfate anhydride, and concentrated, thereby yielding the entitled compound (3.687 g) as yellowish orange solid.

$^1$H-NMR (CDCl$_3$) δ: 2.31 (6H, s), 2.64 (2H, t, J=6.1 Hz), 3.01 (3H, d, J=4.9 Hz), 3.38 (2H, td, J=6.1, 4.9 Hz), 6.16 (1H, m), 6.87 (1H, d, J=9.3 Hz), 7.97 (1H, dd, J=9.3, 2.0 Hz), 8.53 (1H, d, J=2.0 Hz), 8.60 (1H, brt).

(2) 3-Amino-4-{[2-(dimethylamino)ethyl]amino}-N-methylbenzamide

10% of palladium-carbon (0.738 g) was added to a solution containing 4-{[2-(dimethylamino)ethyl]amino}-N-methyl-3-nitrobenzamide (3.679 g) in a mixture of ethyl acetate (40 ml) and ethanol (37 ml), and the mixture was stirred for 4.5 hours under a hydrogen gas atmosphere at room temperature. After the catalyst was removed out by filtration, the filtrate was concentrated. The residue, with ethyl acetate added thereto, was washed with 1N sodium hydroxide aqueous solution and saturated brine successively, dried over sodium sulfate anhydride, and concentrated, thereby yielding the entitled compound (2.862 g) as brown solid.

$^1$H-NMR (CDCl$_3$) δ: 2.26 (6H, s), 2.60 (2H, t, J=5.9 Hz), 2.97 (3H, d, J=4.9 Hz), 3.18 (2H, m), 3.39 (2H, brs), 4.34 (1H, brs), 5.98 (1H, m), 6.57 (1H, d, J=8.3 Hz), 7.18 (1H, dd, J=8.3, 2.0 Hz), 7.22 (1H, d, J=2.0 Hz).

(3) 1-[2-(Dimethylamino)ethyl]-2-heptadecyl-N-methyl-1H-benzimidazole-5-carboxamide Triethylamine (1.00 ml) was added to a solution containing 3-amino-4-{[2-(dimethylamino)ethyl]amino}-N-methylbenzamide (1.500 g) in chloroform (15 ml), and then stearoyl chloride (2.20 mnl) was added thereto while being cooled with ice. After being stirred for 2.5 hours, the reaction mixture was diluted with chloroform, washed with saturated sodium hydrogencarbonate aqueous solution and saturated brine successively, dried over sodium sulfate anhydride, and concentrated. Concentrated hydrochloric acid (5.3 ml) was added to a solution containing the residue (3.030 g) in ethanol (30 ml). After being stirred for 1.5 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (3.737 g) was purified by silica gel column chromatography (silica gel 75 g, chloroform:methanol=50:1–30:1), thereby yielding the entitled compound (2.225 g) as pale yellow solid.

$^1$H-NMR (CDCl$_3$) δ: 0.88 (3H, t, J=6.8 Hz), 1.2–1.4 (26H, m), 1.46 (2H, m), 1.90 (2H, quintet, J=7.7 Hz), 2.31 (6H, s), 2.63 (2H, t, J=7.2 Hz), 2.88 (2H, t, J=7.7 Hz), 3.04 (3H, d, J=4.9 Hz), 4.21 (2H, t, J=7.2 Hz), 6.15 (1H, m), 7.33 (1H, d, J=8.3 Hz), 7.79 (1H, dd, J=8.3, 1.5 Hz), 8.02 (1H, d, J=1.5 Hz).

Example 39

1-[2-(Dimethylamino)ethyl]-2-heptadecyl-N-methyl-1H-benzimidazole-5-carboxamide monohydrochloride (Compound 39)

4N Hydrochloric acid/ethyl acetate solution (1.24 ml) was added to a solution containing 1-[2-(dimethylamino)ethyl]-2-heptadecyl-N-methyl-1H-benzimidazole-5-carboxamide (2.207 g) in a mixture of ethyl acetate (22 ml) and ethanol (2 ml). After being stirred for 30 minutes while being cooled with ice, the reaction mixture was concentrated. The residue was recrystallized with the mixed solution of ethyl acetate-ethanol, thereby yielding the entitled compound (1.751 g) as white crystals.

$^1$H-NMR (CDCl$_3$) δ: 0.88 (3H, t, J=6.8 Hz), 1.2–1.4 (26H, m), 1.44 (2H, m), 1.86 (2H, quintet, J=7.8 Hz), 2.85 (6H, s), 2.95 (2H, t, J=7.8 Hz), 3.01 (3H, d, J=4.4 Hz), 3.31 (2H, brt), 4.73 (2H, brt), 6.87 (1H, m), 7.54 (1H, d, J=8.3 Hz), 7.69 (1H, d, J=8.3 Hz), 8.03 (1H, s).

Example 40

1-[2-(Dimethylamino)ethyl]-2-henicosyl-N-methyl-1H-benzimidazole-5-carboxamide

Compound 40

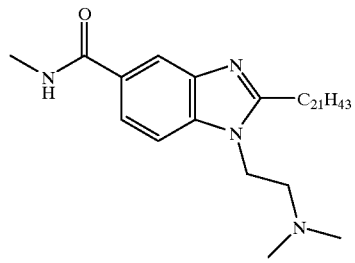

Triethylamine (0.88 ml) was added to a suspension containing n-docosanoic acid (1.950 g) in chloroform (20 ml), and then ethyl chlorocarbonate (0.60 ml) was added thereto while being cooled with ice. The mixture was stirred for 1.5 hours and then a solution containing 3-amino-4-{[2-(dimethylamino)ethyl]amino}-N-methylbenzamide (1.345 g) in chloroform (8 ml) was added thereto. After being stirred for 3 hours while being cooled with ice and further stirred for 1.5 hours at room temperature, the reaction mixture was diluted with chloroform, washed with saturated sodium hydrogencarbonate aqueous solution and saturated brine successively, dried over sodium sulfate anhydride, and concentrated. Concentrated hydrochloric acid (4.8 ml) was added to a suspension containing the residue (3.079 g) in ethanol (31 ml). After being stirred for 1.5 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (3.238 g) was purified by silica gel column chromatography (silica gel 75 g, chloroform:methanol=50:1–30:1–10:1), thereby yielding the entitled compound (1.372 g) as pale brown solid.

$^1$H-NMR (CDCl$_3$) δ: 0.88 (3H, t, J=6.8 Hz), 1.2–1.4 (34H, m), 1.46 (2H, m), 1.90 (2H, quintet, J=7.8 Hz), 2.31 (6H, s), 2.63 (2H, t, J=7.3 Hz), 2.88 (2H, t, J=7.8 Hz), 3.04 (3H, d, J=4.9 Hz), 4.21 (2H, t, J=7.3 Hz), 6.16 (1H, m), 7.33 (1H, d, J=8.8 Hz), 7.78 (1H, dd, J=8.8, 1.5 Hz), 8.02 (1H, d, J=1.5 Hz).

Example 41

1-[2-(Dimethylamino)ethyl]-2-henicosyl-N-methyl-1H-benzimidazole-5-carboxamide monohydrochloride (Compound 41)

4N Hydrochloric acid/ethyl acetate solution (0.68 ml) was added to a solution containing 1-[2-(dimethylamino)ethyl]-2-henicosyl-N-methyl-1H-benzimidazole-5-carboxamide (1.345 g) in a mixture of ethyl acetate (14 ml) and ethanol (1.5 ml). After being stirred for 30 minutes while being cooled with ice, the reaction mixture was concentrated. The residue was recrystallized with the mixed solution of ethyl acetate-ethanol, thereby yielding the entitled compound (1.254 g) as white crystals.

$^1$H-NMR (CDCl$_3$) δ: 0.88 (3H, t, J=6.8 Hz), 1.2–1.4 (34H, m), 1.45 (2H, m), 1.87 (2H, quintet, J=7.6 Hz), 2.85 (6H, s), 2.95 (2H, t, J=7.6 Hz), 3.02 (3H, d, J=4.9 Hz), 3.30 (2H, brt), 4.74 (2H, brt), 6.80 (1H, m), 7.54 (1H, d, J=8.8 Hz), 7.70 (1H, d, J=8.8 Hz), 8.03 (1H, s).

Example 42

1-[2-(Dimethylamino)ethyl]-2-henicosyl-N,N-dimethyl-1H-benzimidazole-5-carboxanmide Compound 42

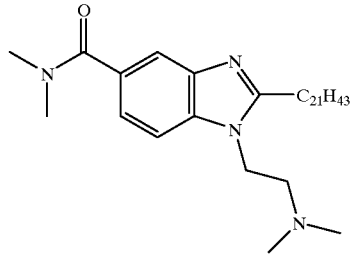

(1) 4-{[2-(Dimethylamino)ethyl]amino}-N,N-dimethyl-3-nitrobenzamide

N,N-Dimethylethylenediamine (2.10 ml) was added to 4-chloro-N,N-dimethyl-3-nitrobenzamide (2.140 g) and the mixture was stirred for 16.5 hours at 100° C. The reaction mixture, with ethyl acetate added thereto, was washed with 1N sodium hydroxide aqueous solution and saturated brine successively, dried over sodium sulfate anhydride, and concentrated, thereby yielding the entitled compound (2.638 g) as orange solid.

$^1$H-NMR (CDCl$_3$) δ: 2.31 (6H, s), 2.64 (2H, t, J=6.1 Hz), 3.09 (6H, s), 3.37 (2H, td, J=6.1, 4.9 Hz), 6.86 (1H, d, J=9.3 Hz), 7.62 (1H, dd, J=9.3, 2.0 Hz), 8.32 (1H, d, J=2.0 Hz), 8.50 (1H, brt).

(2) 3-Amino-4-{[2-(dimethylamino)ethyl]amino}-N,N-dimethylbenzamide

10% of palladium-carbon (0.535 g) was added to a solution containing 4-{[2-(dimethylamino)ethyl]amino}-N,N-dimethyl-3-nitrobenzamide (2.672 g) in ethanol (27 ml) and the mixture was stirred for 5.5 hours under a hydrogen gas atmosphere at room temperature. After the catalyst was removed out by filtration, the filtrate was concentrated, thereby yielding the entitled compound (2.464 g) as blackish brown oil.

$^1$H-NMR (CDCl$_3$) δ: 2.26 (6H, s), 2.59 (2H, t, J=5.9 Hz), 3.05 (6H, s), 3.17 (2H, td, J=5.9, 4.9 Hz), 3.42 (2H, brs), 4.19 (1H, brt), 6.57 (1H, d, J=8.3 Hz), 6.85 (1H, d, J=2.0 Hz), 6.91 (1H, dd, J=8.3, 2.0 Hz).

(3) 1-[2-(Dimethylamino)ethyl]-2-henicosyl-N,N-dimethyl-1H-benzimidazole-5-carboxamide Triethylamine (1.52 ml) was added to a suspension containing n-docosanoic acid (3.339 g) in chloroform (34 ml), and then ethyl chlorocarbonate (1.04 ml) was added thereto while being cooled with ice. The reaction mixture was stirred for 1.5 hours, and then a solution containing 3-amino-4-{[2-(dimethylarnino)ethyl]amino}-N,N-dimethylbenzamide (2.454 g) in chloroform (12 ml) was added thereto. After being stirred for 3 hours while being cooled with ice, the reaction mixture was diluted with chloroform, washed with saturated sodium hydrogencarbonate aqueous solution and saturated brine successively, dried over sodium sulfate anhydride, and concentrated. Concentrated hydrochloric acid (8.2 ml) was added to a suspension containing the residue (6.094 g) in ethanol (61 ml). After being stirred for 1.5 hours at 90° C., the reaction mixture was concentrated. The residue, with ethyl acetate added thereto, was washed with 1N sodium hydroxide aqueous solution and saturated brine successively, dried over sodium sulfate anhydride, and concentrated. The residue (5.119 g) was purified by silica gel column chromatography (silica gel 100 g, chloroform:methanol=50:1–30:1), thereby yielding the entitled compound (3.320 g) as white solid.

$^1$H-NMR (CDCl$_3$) δ: 0.88 (3H, t, J=6.8 Hz), 1.2–1.4 (34H, m), 1.46 (2H, m), 1.91 (2H, quintet, J=7.7 Hz), 2.31 (6H, s), 2.63 (2H, t, J=7.3 Hz), 2.87 (2H, t, J=7.7 Hz), 3.09 (6H, brs), 4.21 (2H, t, J=7.3 Hz), 7.32 (1H, d, J=8.3 Hz), 7.38 (1H, dd, J=8.3, 1.5 Hz), 7.76 (1H, d, J=1.5 Hz).

Example 43

1-[2-(Dimethylamino)ethyl]-2-henicosyl-N,N-dimethyl-1H-benzimidazole-5-carboxamide monohydrochloride (Compound 43)

4N Hydrochloric acid/ethyl acetate solution (1.22 ml) was added to a solution containing 1-[2-(dimethylamino)ethyl]-2-henicosyl-N,N-dimethyl-1H-benzimidazole-5-carboxamide (2.500 g) in ethyl acetate (25 ml). After being stirred for 30 minutes at room temperature, the reaction mixture was concentrated. The residue was recrystallized with a mixed solution of ethyl acetate-ethanol, thereby yielding the entitled compound (2.175 g) as white crystals.

$^1$H-NMR (CDCl$_3$) δ: 0.88 (3H, t, J=6.8 Hz), 1.2–1.4 (34H, m), 1.46 (2H, m), 1.90 (2H, quintet, J=7.8 Hz), 2.84 (6H, s), 2.97 (2H, t, J=7.8 Hz), 3.01 (3H, brs), 3.13 (3H, brs), 3.27 (2H, brs), 4.78 (2H, brs), 7.34 (1H, dd, J=8.3, 1.5 Hz), 7.59 (1H, d, J=8.3 Hz), 7.75 (1H, d, J=1.5 Hz).

| Preparetion Example 1 Hair growth tonic | |
| --- | --- |
| Compound 7 | 0.5 wt % |
| Pyridoxine dioctanoate | 0.1 |
| Pantothenyl ethyl ether | 0.2 |
| Hinokitiol | 0.05 |
| Polyoxyethylene (12) polyoxypropylene (6) decyl tetradecyl | 1.0 |
| 1-Menthol | 0.1 |
| Disinfectants | Q.S. |
| 1,3-Butylene glycol | 3.0 |
| Ethanol | 70.0 |
| Purified water | Balance |
| <Preparation Method> | |

Ethanol-soluble ingredients were dissolved into ethanol at room temperature while being stirred. Water-soluble ingredients were dissolved in purified water. The aqueous solution was added to the ethanol solution. After being uniformly mixed, the mixture was filtrated.

| Preparetion Example 2 Hair regrowth promoting liquid lotion | |
| --- | --- |
| Compound 28 | 0.2 wt % |
| Carpronium chloride | 1.0 |
| Pantothenyl ethyl ether | 0.5 |
| Diphenhydramine hydrochloride | 0.1 |
| Hinokitiol | 0.1 |
| dl-α-Tocopheryl acetate | 0.1 |
| Salicylic acid | 0.2 |
| 1-Menthol | 0.2 |
| Glycyrrhizinic acid | 0.1 |
| Sodium dl-pyrrolidonecarboxylate solution | 1.0 |
| Ethanol | 70.0 |
| Purified water | Balance |
| <Preparation Method> | |

Ethanol-soluble ingredients were dissolved into ethanol at room temperature while being stirred. Water-soluble ingredients were dissolved in purified water. The aqueous solution was added to the ethanol solution. After being uniformly mixed, the mixture was filtrated.

| Preparetion Example 3 Hair tonic | |
| --- | --- |
| Compound 5 | 0.1 wt % |
| Paeony root extract (1,3-butylene glycol extract) | 0.01 |
| Hinokitiol | 1.0 |
| Vitamin B6 | 0.2 |
| Vitamin E acetate | 0.02 |
| Menthol | 0.2 |
| Swertia herb extract | 1.0 |
| Salicylic acid | 0.1 |
| Rosae rugosae flos extract (ethanol extract) | 0.5 |
| Propylene glycol | 2.0 |
| Sodium hyaluronate | 0.01 |
| Polyoxyethylene (10) monostearate | 2.0 |
| 75% Ethanol | Balance |
| <Preparation Method> | |

Each of the above ingredients was successively added and dissolved into 75% ethanol with stirring to obtain a hair tonic.

| Preparation Example 4 Hair tonic | |
|---|---|
| Paeonia extract (ethanol extract) | 5.0 wt % |
| Compound 11 | 0.05 |
| Compound 15 | 0.05 |
| Hinokitiol | 1.0 |
| Vitamin B6 | 0.2 |
| Vitamin E acetate | 0.02 |
| Menthol | 0.2 |
| Salicylic acid | 0.1 |
| Pueraria root extract (ethanol extract) | 0.5 |
| Propylene glycol | 2.0 |
| Sodium hyaluronate | 0.01 |
| Polyoxyethylene (10) monostearate | 2.0 |
| 75% Ethanol | Balance |
| <Preparation Method> | |

Each of the above ingredients was successively added and dissolved into 75% ethanol with stirring to obtain a hair tonic.

| Preparation Example 5 Hair tonic | |
|---|---|
| Compound 31 | 0.05 wt % |
| 95% Ethanol | 50.0 |
| Monoammonium glycyrrhizinate | 0.05 |
| Paeonia extract (ethanol extract) | 0.05 |
| Paeony root extract (1,3-butylene glycol extract) | 0.02 |
| Saffron extract (ethanol extract) | 0.02 |
| Rosemary extract (ethanol extract) | 0.02 |
| Peppermint extract (ethanol extract) | 0.02 |
| Japanese angelica root extract (ethanol extract) | 0.02 |
| Althea extract (ethanol extract) | 0.02 |
| Rehmannia root extract (ethanol extract) | 0.02 |
| Coix extract (ethanol extract) | 0.02 |
| Sodium lauryl sulfate | 0.1 |
| N,N-Dimethyl-2-decyltetradecylamineoxide | 0.5 |
| Polyoxyethylene (40) hydrogenated castor oil | 0.5 |
| Succinic acid | Q.S. |
| Perfume and coloring agent | Q.S. |
| Purified water | Balance |
| <Preparation Method> | |

A hair tonic was prepared according to Preparation Example 1.

| Preparation Example 6 Hair lotion | |
|---|---|
| 95% Ethanol | 90.0 wt % |
| Vitamin E acetate | 0.05 |
| Compound 27 | 0.01 |
| Sodium lauryl sulfate | 0.06 |
| Propylene glycol | 0.1 |
| Polyoxyethylene (40) hydrogenated castor oil | 0.5 |
| Lactic acid | Q.S. |
| Sodium lactate | Q.S. |
| Perfume and coloring agent | Q.S. |
| Purified water | Balance |
| <Preparation Method> | |

Polyoxyethylene (40) hydrogenated castor oil and perfume were dissolved in 95% ethanol. Then, purified water and the other ingredients were successively added and dissolved into the mixture with stirring to obtain a transparent liquid lotion.

| Preparation Example 7 Hair tonic | |
|---|---|
| Compound 25 | 0.1 wt % |
| Hinokitiol | 1.0 |
| Vitamin B6 | 0.2 |
| Vitamin E acetate | 0.02 |
| Menthol | 0.2 |
| Swertia herb extract | 1.0 |
| Salicylic acid | 0.1 |
| Propylene glycol | 2.0 |
| Polyoxyethylene (10) monostearate | 2.0 |
| 75% Ethanol | Balance |
| <Preparation Method> | |

Each of the above ingredients was successively added and dissolved into 75% ethanol with stirring to obtain a hair tonic.

| Preparation Example 8 Hair tonic | |
|---|---|
| Compound 19 | 0.5 wt % |
| Compound 21 | 0.1 |
| Hinokitiol | 1.0 |
| Vitamin $B_6$ | 0.2 |
| Vitamin E | 0.02 |
| Menthol | 0.2 |
| Salicylic acid | 0.1 |
| Propylene glycol | 2.0 |
| Sodium hyaluronate | 0.01 |
| Polyoxyethylene (10 mol) monostearate | 2.0 |
| 70% Ethanol | Balance |
| <Preparation Method> | |

Each of the above ingredients was successively added and dissolved into 70% ethanol with stirring to obtain a hair tonic.

| Preparation Example 9 O/W milky lotion | |
|---|---|
| (Phase A) | |
| Polyoxyethylene (60) hydrogenated castor oil | 2.0 wt % |
| Glycerin | 10.0 |
| Dipropylene glycol | 10.0 |
| 1,3-Butylene glycol | 4.0 |
| Compound 6 | 0.1 |
| Polyethylene glycol 1500 | 5.0 |
| (Phase B) | |
| Isocetyl octanoate | 10.0 |
| Squalane | 5.0 |
| Vaseline | 2.0 |
| Propyl paraben | 2.0 |
| (Phase C) | |
| 1% Carboxyvinyl polymer aqueous solution | 30.0 |
| Sodium hexametaphosphate | 0.03 |
| Ion-exchanged water | 8.35 |
| (Phase D) | |
| Ion-exchanged water | 4.5 |
| (Phase E) | |
| Potassium hydroxide | 0.12 |
| Ion-exchanged water | Balance |
| <Preparation Method> | |

Phases A and B were heated and dissolved, separately. Both were mixed and treated with a homomixer, thereby obtaining a gel. Phase D was then gradually added to this gel and dispersed by the homomixer. Then, Phases C and E, which were mixed and dissolved in advance separately, were added to this gel dispersion successively. The mixture was emulsified by the homomixer to obtain an O/W milky lotion.

| Preparetion Example 10 Cream | |
|---|---|
| (Phase A) | |
| N,N-Dimethyl-2-tetradecylamineoxide | 2.5 wt % |
| Liquid paraffin | 5.0 |
| Cetostearyl alcohol | 5.5 |
| Glyceryl monostealate | 3.0 |
| Polyoxyethylene (20) 2-octyldodecyl ether | 3.0 |
| Propyl paraben | 0.3 |
| Perfume | 0.1 |
| (Phase B) | |
| Compound 8 | 1.0 |
| Glycerin | 8.0 |
| Dipropylene glycol | 20.0 |
| Polyethylene glycol 4000 | 5.0 |
| Sodium hexametaphosphate | 0.005 |
| Ion-exchanged water | Balance |
| <Preparation Method> | |

Phases A and B were heated and dissolved, separately. Both were mixed and emulsified by a homomixer to obtain a cream.

| Preparetion Example 11 Aerosol spray | |
|---|---|
| (Stock solution) | |
| 95% Ethanol | 50.0 wt % |
| Glycyrrhizic acid | 0.1 |
| Compound 23 | 0.5 |
| Swertia herb extract | 0.1 |
| Sodium lauryl sulfate | 0.1 |
| Polyoxyethylene (40) hydrogenated castor oil | 0.5 |
| Lactic acid | Q.S. |
| Sodium lactate | Q.S. |
| Perfume | Q.S. |
| Ion-exchanged water | Balance |
| (Filling formulation) | |
| Stock solution | 50.0 |
| Liquefied petroleum gas | 50.0 |
| <Preparation Method> | |

A stock solution was prepared by mixing and dissolving the ingredients of stock solution. This stock solution was filled into a can and a valve was fit thereto. Liquefied petroleum gas was filled into the can to obtain an aerosol spray.

| Preparetion Example 12 Shampoo | |
|---|---|
| (1) Sodium cocoylmethyltaurate | 2.0 wt % |
| (2) Polyoxyethylene (8) oleyl ether | 2.0 |
| (3) Lauric acid diethanolamide | 4.0 |
| (4) Ethylene glycol fatty acid ester | 1.0 |
| (5) Glycerine | 0.2 |
| (6) Menthol | 0.1 |
| (7) Compound 17 | 0.1 |
| (8) Disodium edetate | 0.1 |
| (9) Perfume | Q.S. |
| (10) Purified water | Balance |
| <Preparation Method> | |

The ingredient (10) was heated up to 70° C. The ingredients (1)–(9) were added to the heated ingredient (10) successively, and the mixture was mixed and dissolved with stirring. The mixture was cooled to obtain a shampoo.

| Preparetion Example 13 Rinse | |
|---|---|
| (1) Stearyl trimethyl ammonium chloride | 1.5 wt % |
| (2) Dimethyl polysiloxane (20 cs) | 3.0 |
| (3) Polyoxyethylene (10) oleyl ether | 1.0 |
| (4) Glycerine | 5.0 |
| (5) Compound 6 | 0.5 |
| (6) 4-tert-Butyl-4'-methoxydibenzoylmethane | Q.S. |
| (7) Ultraviolet absorber | Q.S. |
| (8) Purified water | Balance |
| <Preparation Method> | |

The water phase was prepared by adding the ingredients (1), (3) and (4) to the ingredient (8) and heating up to 70° C. The oil phase was prepared by heating and dissolving the other ingredients up to 70° C. The oil phase was added to the water phase and the mixture was mixed with stirring by an emulsifier. The mixture was cooled to obtain a rinse.

| Preparation Example 14 Scalp treatment | |
|---|---|
| (Stock solution) | |
| (1) Liquid paraffin | 27.0 wt % |
| (2) Stearic acid | 5.0 |
| (3) Cetanol | 5.0 |
| (4) Sorbitan monooleate | 2.0 |
| (5) Polyoxyethylene sorbitan monooleate | 3.0 |
| (6) Compound 7 | 0.1 |
| (7) 1,3-Butylene glycol | 5.0 |
| (8) Antiseptic | Q.S. |
| (9) Purified water | Balance |
| (Filling formulation) | |
| Stock solution | 50.0 |
| Liquefied petroleum gas | 50.0 |
| <Preparation Method> | |

The ingredients (5) and (6) were dissolved into ingredients (1) to (4). After being uniformly dissolved with heating up to 80° C., the mixture was cooled down to 30° C. This mixture was added to the mixed solution of the ingredients (7) to (9), which was maintained at 30° C., and mixed with stirring to obtain a stock solution. This stock solution was filled into a can together with the liquefied petroleum gas to obtain a scalp treatment.

| Preparation Example 15 Scalp treatment | |
|---|---|
| (Stock solution) | |
| (1) Hinokitiol | 0.1 wt % |
| (2) Swertia herb extract | 1.0 |
| (3) Vitamin $B_6$ | 0.1 |
| (4) Vitamin E | 0.01 |
| (5) Menthol | 0.1 |
| (6) Salicylic acid | 0.001 |
| (7) Compound 29 | 0.1 |
| (8) Polyoxyethylene sorbitan monooleate | 0.1 |
| (9) Propylene glycol | 2.0 |

-continued

| Preparetion Example 15 Scalp treatment | |
|---|---|
| (10) 75% Ethanol (Filling formulation) | Balance |
| Stock solution | 50.0 |
| Dimethyl ether | 50.0 |

<Preparation Method>

A scalp treatment was prepared according to Preparation Example 14.

In the following, the compounds and manufacturing processes thereof in accordance with the present invention are exemplified.

Compound 44

N-(2-Aminoethyl)-1-octadecyl-1H-benzimidazole-2-carboxamide

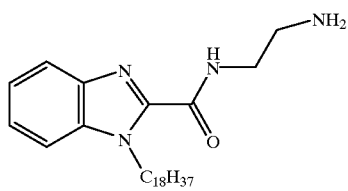

In Example 28 (4), ethylenediamine is used in place of N,N-dimethyl-1,3-propanediamine to give the entitled compound.

Compound 45

N-{3-[Bis(2-hydroxyethyl)amino]propyl}-1-octadecyl-1H-benzimidazole-2-carboxamide

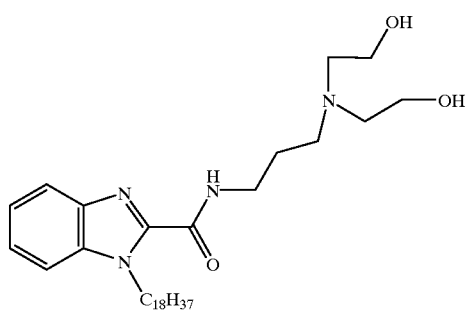

In Example 28 (4), N-(3-aminopropyl)diethanolamine is used in place of N,N-dimethyl-1,3-propanediamine to give the entitled compound.

Compound 46

N-[3-(Dibenzylamino)propyl]-1-octadecyl-1H-benzimidazole-2-carboxamide

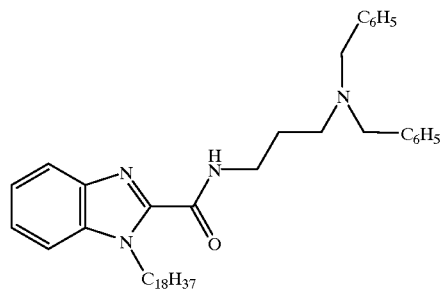

In Example 28 (4), N,N-dibenzyl-1,3-propanediamine is used in place of N,N-dimethyl-1,3-propanediamine to give the entitled compound.

Compound 47

3-(2-heptadecyl-1H-benzimidazol-1-yl)-N-methyl-N-phenyl-1-propanamine

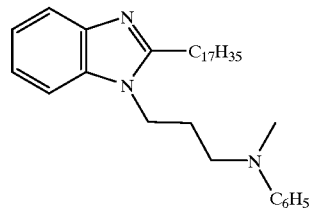

In Example 1, N-(3-aminopropyl)-N-methylaniline is used in place of N,N-dimethyl-1,3-propanediamine to give the entitled compound.

Compound 48

N,N-Dimethyl-1-octadecyl-1H-benzimidazole-2-carbohydrazide

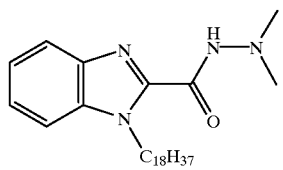

In Example 28 (4), N,N-dimethylhydrazine is used in place of N,N-dimethyl-1,3-propanediamine to give the entitled compound.

Compound 49

1-Octadecyl-N-(5-pyrrolidinopentyl)-1H-benzimidazole-2-carboxamide

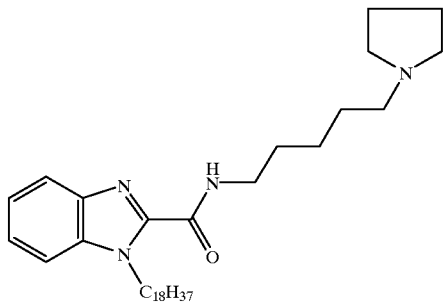

In Example 28 (4), N-(5-aminopentyl)pyrrolidine is used in place of N,N-dimethyl-1,3-propanediamine to give the entitled compound.

Compound 50

3-(5-Cyano-2-heptadecyl-1H-benzimidazol-1-yl)-N,N-dimethyl-1-propanamine

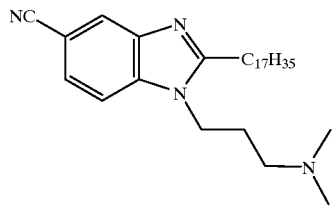

In Example 1, 4-chloro-3-nitrobenzonitrile is used in place of 2-chloronitrobenzene to give the entitled compound.

Compound 51

3-[2-Heptadecyl-5-(trifluoromethyl)-1H-benzimidazol-1-yl]-N,N-dimethyl-1-propanamine

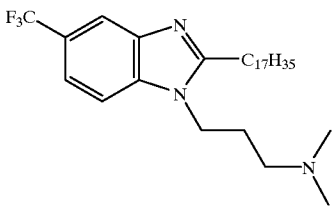

In Example 1, 2-chloro-5-trifluoromethylnitrobenzene and stearoyl chloride are used in place of 2-chloronitrobenzene and dodecanoyl chloride respectively, to give the entitled compound.

Compound 52

3-(5-Acetyl-2-heptadecyl-1H-benzimidazol-1-yl)-N,N-dimethyl-1-propanamine

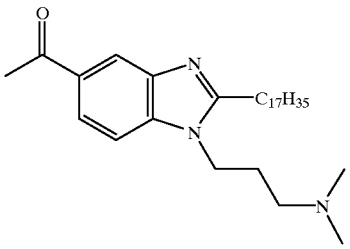

In Example 1, 5-acetyl-2-chloronitrobenzene and stearoyl chloride are used in place of 2-chloronitrobenzene and dodecanoyl chloride respectively, to give the entitled compound.

Compound 53

1-[3-(Dimethylamino)propyl]-2-heptadecyl-1H-benzimidazole-5-carboxilic acid

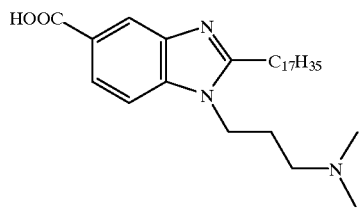

Compound 50 is hydrolyzed by heating in an acidic or basic condition to give the entitled compound.

Compound 54

1-[3-(Dimethylamino)propyl]-2-heptadecyl-1H-benzimidazole-5-carboxamide

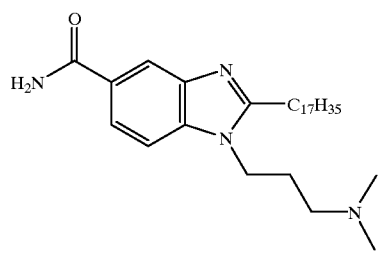

After thionyl chloride is added in a solution containing Compound 53 in dimethylformamide and stirred, ammonium chloride and triethylamine are further added thereto and reacted to give the entitled compound.

Compound 55

3-[5-(Dimethylamino)-2-heptadecyl-1H-benzimidazol-1-yl]-N,N-dimethyl-1-propanamine

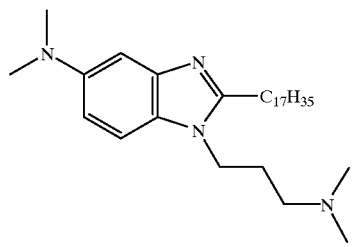

In Example 1, 5-dimethylamino-2-chloronitrobenzene and stearoyl chloride are used in place of 2-chloronitrobenzene and dodecanoyl chloride respectively, to give the entitled compound.

Compound 56

N-{1-[3-(Dimethylamino)propyl]-2-heptadecyl-1H-benzimidazole-5-yl}benzamide

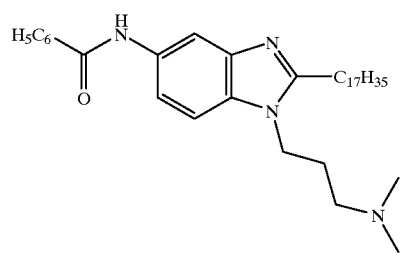

Triethylamine is added to a solution containing Compound 27 in chloroform, and then benzoyl chloride is added thereto while being cooled with ice. The mixture is stirred at room temperature to give the entitled compound.

Compound 57

3-[2-Heptadecyl-5-hydroxy-1H-benzimidazol-1-yl]-N,N-dimethyl-1-propanamine

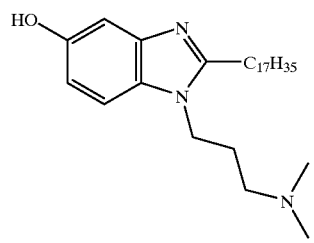

In Example 27, 4-chloro-3-nitrophenol is used as a starting material in place of 4-chloro-3-nitroaniline to give the entitled compound.

Compound 58

3-(2-Heptadecyl-5-methoxy-1H-benzimidazol-1-yl)-N,N-dimethyl-1-propanamine

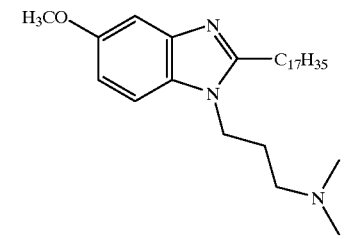

In Example 1, 5-methoxy-2-chloronitrobenzene and stearoyl chloride are used in place of 2-chloronitrobenzene and dodecanoyl chloride respectively, to give the entitled compound.

Compound 59

1-[3-(Dimethylamino)propyl]-2-heptadecyl-1H-benzimidazole-5-yl acetate

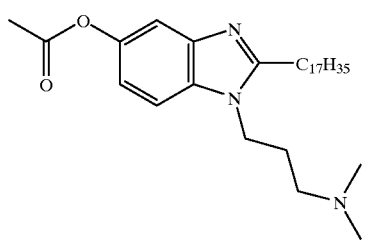

Acetic anhydrate is reacted with Compound 57 to give the entitled compound

Compound 60

N-[3-(Dimethylamino)propyl]-N-methyl-2-octadecyl-1H-benzimidazole-2-carboxamide

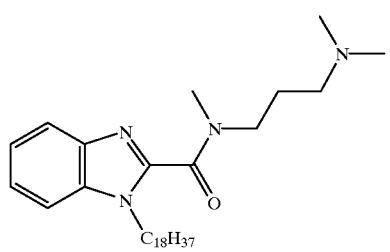

In Example 28, N,N,N'-trimethylamino-1,3-propanediamine is used in place of N,N-dimethyl-1,3-propanediamine to give the entitled compound.

Compound 61

N-Acetyl-N-[3-(dimethylamino)propyl]-1-octadecyl-1H-benzimidazole-2-carboxamide

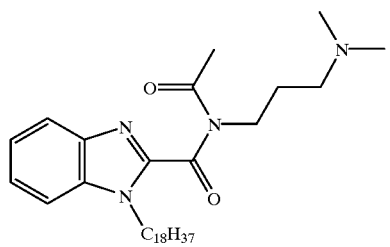

Compound 28 is acetylated by using a known method to give the entitled compound.

Compound 62

N-[3-(Dimethylamino)propyl]-N-(methylcarbamoyl)-1-octadecyl-1H-benzimnidazole-2-carboxamide

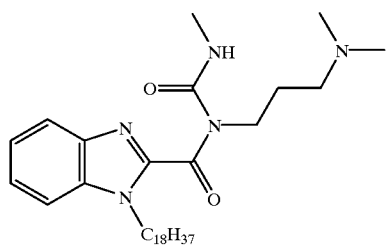

Compound 28 is methylcarbamoylated by using a known method to give the entitled compound.

Compound 63

N,N-Dimethyl-2-(1-octadecyl-1H-benzimidazole-2-yl)-1-ethanamine

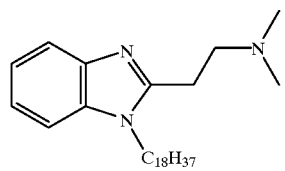

In Example 1 (1), octadecylamine is used in place of N,N-dimethyl-1,3-propanediamine. The resulting compound is subjected to catalytic reduction in a similar manner to Example 1 (2) to give N-octadecyl-1,2-benzenediamine.

Concentrated hydrochloric acid is added to a ethanol solution containing an amide, which is obtained from N-octadecyl-1,2-benzenediamine and 3-(dimethylamino) propionic acid by using a known method, and heated to give the entitled compound.

Compound 64

1-[3-(Dimethylamino)propyl]-N-octadecyl-1H-benzimidazole-2-carboxamide

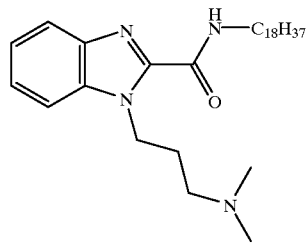

What is claimed is:

1. A benzimidazole compound or a salt thereof expressed by the following Formula (I):

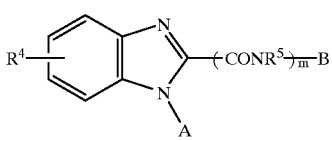

(I)

wherein each of A and B is $R^1$ or $-(CH_2)_n-NR^2R^3$, wherein when A is $R^1$, B is $-(CH_2)_n-NR^2R^3$ and when A is $-(CH_2)_n-NR^2R^3$, B is $R^1$;

$R^1$ is a hydrocarbon group having 10 to 30 carbon atoms;

$R^2$ and $R^3$ individually represent a hydrogen atom, a lower alkyl group, a phenyl group or a benzyl group, or $-NR^2R^3$ may be a heterocycle having 3–7 members; wherein when B is $-(CH_2)_n-NR^2R^3$ and m=1, $-(CONR^5)_m-B$ may be the following Group (W):

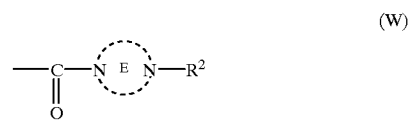

(W)

wherein $R^2$ is a hydrogen atom, a lower alkyl group, a phenyl group or a benzyl group and ring E is a heterocycle of 6 or 7 members;

$R^4$ is selected from the group consisting of a hydrogen atom, a halogen atom, a cyano group, a trifluoromethyl group, a lower alkyl group, a lower acyl group, a carboxyl group, a lower alkoxycarbonyl group, a carbamoyl group, a lower alkylcarbamoyl group, an amino group, a lower alkylamino group, a lower acylamino group, a hydroxy group, a lower alkoxy group and a lower acyloxy group;

$R^5$ is a hydrogen atom, a lower alkyl group, a lower acyl group or a lower alkylcarbamoyl group; wherein when B is $-(CH_2)_n-NR^2R^3$ and m=1, $-(CONR^5)_m-B$ may be Group (W);

m is 0 or 1;

n is an integer of 0–5; and wherein when m is 0 then A is $-(CH_2)_n-NR^2R^3$ and B is an alkyl group having at least 10 carbon atoms.

2. A benzimidazole compound or a salt thereof according to claim 1, wherein A is $-(CH_2)_n-NR^2R^3$ and B is $R^1$.

3. A benzimidazole compound or a salt thereof expressed by the following Formula (I):

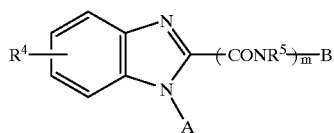

(I)

wherein m=0; A is —$(CH_2)_n$—$NR^2R^3$, and B is an alkyl group having at least 10 carbon atoms; n is an integer of 0–5; $R^2$ and $R^3$ individually represent a hydrogen atom, a lower alkyl group, a phenyl group or a benzyl group, or —$NR^2R^3$ may be a heterocycle having 3–7 members; and $R^4$ is selected from the group consisting of a hydrogen atom, a halogen atom, a cyano group, a trifluoromethyl group, a lower alkyl group, a lower acyl group, a carboxyl group, a lower alkoxycarbonyl group, a carbamoyl group, a lower alkylcarbamoyl group, an amino group, a lower alkylamino group, a lower acylamino group, a hydroxy group, a lower alkoxy group and a lower acyloxy group.

4. A benzimidazole compound or a salt thereof according to claim 1, wherein A is $R^1$ and B is —$(CH_2)_n$—$N^2R^3$.

5. A benzimidazole compound or a salt thereof expressed by the following Formula (I):

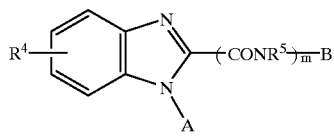

(I)

wherein A is $R^1$ and B is —$(CH_2)_n$—$NR^2R^3$;
$R^1$ is a hydrocarbon group of having 10 to 30 carbon atoms;
$R^2$ and $R^3$ individually represent a hydrogen atom, a lower alkyl group, a phenyl group or a benzyl group, or —$NR^2R^3$ may be a heterocycle having 3–7 members;
$R^4$ is selected from the group consisting of a hydrogen atom, a halogen atom, a cyano group, a trifluoromethyl group, a lower alkyl group, a lower acyl group, a carboxyl group, a lower alkoxycarbonyl group, a carbamoyl group, a lower alkylcarbamoyl group, an amino group, a lower alkylamino group, a lower acylamino group, a hydroxy group, a lower alkoxy group and a lower acyloxy group;
$R^5$ is a hydrogen atom, a lower alkyl group, a lower acyl group or a lower alkylcarbamoyl group;
m is 1;
n is an integer of 0–5; and
wherein —$(CONR^5)_m$—B may be expressed by the following Group (W):

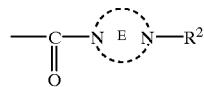

(W)

wherein $R^2$ is a hydrogen atom, a lower alkyl group, a phenyl group or a benzyl group and ring E is a heterocycle of 6 or 7 members.

6. A benzimidazole compound or a salt thereof according to claim 5, wherein $R^5$ is a hydrogen atom.

7. A benzimidazole compound or a salt thereof according to claim 5, wherein —$CONR^5$—$(CH_2)_n$—$NR^2R^3$ is expressed by the following Group (a) or (b):

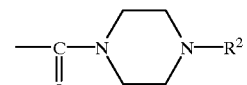

(a)

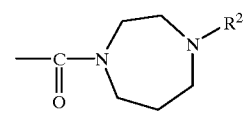

(b)

wherein $R^2$ is a hydrogen atom, a lower alkyl group, a phenyl group or a benzyl group.

8. A benzimidazole compound or a salt thereof according to claim 1, wherein n is an integer of 2–5.

9. A benzimidazole compound or a salt thereof according to claim 1, wherein $R^1$ is an alkyl group having 10 to 30 carbon atoms.

10. A hair growth promoting composition comprising an effective amount of the benzimidazole compound or the pharmacologically acceptable salt thereof according to claim 1 in admixture with one or more of cosmetically or pharmaceutically acceptable additives, carriers, excipients or diluents therefor.

11. An external preparation for skin comprising the benzimidazole compound or the pharmacologically acceptable salt thereof according to claim 1 in admixture with one or more of cosmetically or pharmaceutically acceptable additives, carriers, excipients or diluents therefor.

12. A method for promoting hair growth, which comprises applying an effective amount of the benzimidazole compound or the pharmacologically acceptable salt thereof expressed by the following Formula (I):

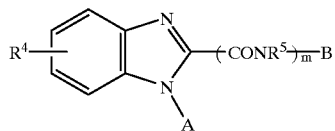

(I)

wherein each of A and B is $R^1$ or —$(CH_2)_n$—$NR^2R^3$, wherein when A is $R^1$, B is —$(CH_2)_n$—$NR^2R^3$ and when A is —$(CH_2)_n$—$NR^2R^3$, B is $R^1$;
$R^1$ is a hydrocarbon group having 10 to 30 carbon atoms;
$R^2$ and $R^3$ individually represent a hydrogen atom, a lower alkyl group, a phenyl croup or a benzyl group, or —$NR^2R^3$ may be a heterocycle having 3–7 members; wherein when B is —$(CH_2)_n$—$NR^2R^3$ and m=1, —$(CONR^5)_m$—B may be the following Group (W):

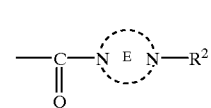

(W)

wherein $R^2$ is a hydrogen atom, a lower alkyl group, a phenyl group or a benzyl group and ring E is a heterocycle of 6 or 7 members;
$R^4$ is selected from the group consisting of a hydrogen atom, a halogen atom, a cyano group, a trifluoromethyl group, a lower alkyl group, a lower acyl group, a carboxyl group, a lower alkoxycarbonyl group, a carbamoyl group, a lower alkylcarbamoyl ground an amino group, a lower alkylamino group, a lower acylamino group, a hydroxy group, a lower alkoxy group and a lower acyloxy group;

$R^5$ is a hydrogen atom, a lower alkyl group, a lower acyl group or a lower alkylcarbamoyl group; wherein when B is —$(CH_2)_n$—$NR^2R^3$ and m=1, —$(CONR^5)_m$—B may be Group (W);

m is 0 or 1;

n is an integer of 0–5; and wherein when m is 0 then A is —$(CH_2)_n$—$NR^2R^3$ and B is an alkyl group having at least 10 carbon atoms in admixture with one or more of cosmetically or pharmaceutically acceptable additives, carriers, excipients or diluents therefor on the skin of a mammalian subject in need of such treatment.

13. A method for promoting hair growth according to claim 12 wherein the skin of said mammalian subject is the scalp of a human subject.

14. The external preparation for skin of claim 11, wherein said benzimidazole compound or the pharmacologically acceptable salt thereof comprises 0.01–20.0% by weight of said preparation and wherein said preparation is in the form of a nonionic vesicle dispersion, emulsion, cream, milk, gel, cream gel, ointment, suspension, dispersion, powder, anhydrous or aqueous solid or paste, rinse, shampoo, lotion, foam or spray.

15. An external preparation for skin which comprises a therapeutically effective amount of the benzimidazole compound or the pharmacologically acceptable salt thereof as claimed in claim 3 in admixture with one or more of cosmetically or pharmaceutically acceptable additives, carriers, excipients or diluents therefor.

16. An external preparation for skin which comprises a therapeutically effective amount of the benzimidazole compound or the pharmacologically acceptable salt thereof as claimed in claim 5 in admixture with one or more of cosmetically or pharmaceutically acceptable additives, carriers, excipients or diluents therefor.

* * * * *

UNITED STATES PATENT AND TRADEMARK OFFICE
CERTIFICATE OF CORRECTION

PATENT NO. : 6,204,264 B1  
DATED : March 20, 2001  
INVENTOR(S) : Koji Kobayashi, Hirotada Fukunishi, Kenichi Umishio, Masahiro Tajima It is certified that error appears in the above-identified patent and that said Letters Patent is hereby corrected as shown below:

Column 62, claim 12,
Line 51, delete "croup" and substitute therefore -- group --.

Column 63, claim 12,
Line 2, delete "ground" and substitute therefore -- group --.

Signed and Sealed this

First Day of January, 2002

*Attest:*

JAMES E. ROGAN
*Attesting Officer*     *Director of the United States Patent and Trademark Office*